US012564642B2

(12) United States Patent
Authelin et al.

(10) Patent No.: US 12,564,642 B2
(45) Date of Patent: Mar. 3, 2026

(54) CEACAM5 ANTIBODY-DRUG CONJUGATE FORMULATION

(71) Applicant: SANOFI, Paris (FR)

(72) Inventors: Jean-René Authelin, Paris (FR); Fethi Bensaid, Paris (FR); Audrey Bonestebe, Paris (FR); Sylvain Huille, Paris (FR); Marie Leman, Paris (FR); Lucie Manache-Alberici, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 17/522,443

(22) Filed: Nov. 9, 2021

(65) Prior Publication Data

US 2022/0202946 A1 Jun. 30, 2022

(30) Foreign Application Priority Data

Nov. 10, 2020 (EP) .................................... 20315449

(51) Int. Cl.

| | |
|---|---|
| ***A61K 47/68*** | (2017.01) |
| ***A61K 39/00*** | (2006.01) |
| ***A61P 35/00*** | (2006.01) |
| ***C07K 16/28*** | (2006.01) |
| ***C07K 16/30*** | (2006.01) |

(52) U.S. Cl.

CPC .... *A61K 47/6849* (2017.08); *A61K 47/68033* (2023.08); *A61K 47/6853* (2017.08); *A61P 35/00* (2018.01); *C07K 16/2818* (2013.01); *C07K 16/2827* (2013.01); *C07K 16/3023* (2013.01); *A61K 2039/505* (2013.01); *A61K 2039/545* (2013.01)

(58) Field of Classification Search

CPC ............ A61K 47/6803; A61K 47/6853; A61K 2039/505; A61K 2039/545; A61K 9/0019; A61K 9/19; A61K 47/12; A61K 47/183; A61K 47/26; A61K 47/6849; A61K 47/6857; A61P 35/00; C07K 16/2818; C07K 16/2827; C07K 16/3023

See application file for complete search history.

(56) References Cited

U.S. PATENT DOCUMENTS

| | | | |
|---|---|---|---|
| 1,045,773 | A | 11/1912 | Cole |
| 4,179,337 | A | 12/1979 | Davis et al. |

(Continued)

FOREIGN PATENT DOCUMENTS

| | | | |
|---|---|---|---|
| CN | 101802012 | A | 8/2010 |
| CN | 108341876 | A | 7/2018 |

(Continued)

OTHER PUBLICATIONS

Beck, A., et al.(2017) Strategies and challenges for the next generation of antibody-drug conjugates Nature Reviews I Drug Discovery 16; 315-337 (Year: 2017).*

(Continued)

*Primary Examiner* — Scarlett Y Goon
*Assistant Examiner* — Audrey L Buttice
(74) *Attorney, Agent, or Firm* — MH2 Technology Law Group, LLP

(57) ABSTRACT

Provided are stabilized formulations of the human carcinoembryonic antigen-related cell adhesion molecule 5 (hCEACAM5)-targeted antibody-drug conjugate huMAb2-3-SPDB-DM4, as well as methods for making and using same.

9 Claims, 31 Drawing Sheets

Specification includes a Sequence Listing.

General representation

Structure of the chemical portion n is about 3.8 drug linked per antibody molecule huMAb2-3-SPDB-DM4

(56) References Cited

U.S. PATENT DOCUMENTS

| | | | |
|---|---|---|---|
| 4,256,746 | A | 3/1981 | Miyashita et al. |
| 4,294,757 | A | 10/1981 | Asai |
| 4,301,144 | A | 11/1981 | Iwashita et al. |
| 4,307,016 | A | 12/1981 | Asai et al. |
| 4,313,946 | A | 2/1982 | Powell et al. |
| 4,315,929 | A | 2/1982 | Freedman et al. |
| 4,322,348 | A | 3/1982 | Asai et al. |
| 4,331,598 | A | 5/1982 | Hasegawa et al. |
| 4,361,650 | A | 11/1982 | Asai et al. |
| 4,362,663 | A | 12/1982 | Kida et al. |
| 4,364,866 | A | 12/1982 | Asai et al. |
| 4,371,533 | A | 2/1983 | Akimoto et al. |
| 4,424,219 | A | 1/1984 | Hashimoto et al. |
| 4,450,254 | A | 5/1984 | Isley et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 4,816,567 | A | 3/1989 | Cabilly et al. |
| 4,861,719 | A | 8/1989 | Miller |
| 4,975,278 | A | 12/1990 | Senter et al. |
| 5,202,238 | A | 4/1993 | Fell, Jr. et al. |
| 5,204,244 | A | 4/1993 | Fell et al. |
| 5,208,020 | A | 5/1993 | Chari et al. |
| 5,215,534 | A | 6/1993 | De Harde et al. |
| 5,225,539 | A | 7/1993 | Winter |
| 5,278,056 | A | 1/1994 | Bank et al. |
| 5,475,092 | A | 12/1995 | Chari et al. |
| 5,500,362 | A | 3/1996 | Robinson et al. |
| 5,530,101 | A | 6/1996 | Queen et al. |
| 5,565,332 | A | 10/1996 | Hoogenboom et al. |
| 5,585,089 | A | 12/1996 | Queen et al. |
| 5,585,499 | A | 12/1996 | Chari et al. |
| 5,821,337 | A | 10/1998 | Carter et al. |
| 5,846,545 | A | 12/1998 | Chari et al. |
| 5,859,205 | A | 1/1999 | Adair et al. |
| 5,882,877 | A | 3/1999 | Gregory et al. |
| 5,994,524 | A | 11/1999 | Matsushima et al. |
| 6,013,516 | A | 1/2000 | Verma et al. |
| 6,018,032 | A | 1/2000 | Koike et al. |
| 6,127,175 | A | 10/2000 | Vigne et al. |
| 6,333,410 | B1 | 12/2001 | Chari et al. |
| 6,464,998 | B1 | 10/2002 | Beuzard et al. |
| 6,629,949 | B1 | 10/2003 | Douglas et al. |
| 6,659,982 | B2 | 12/2003 | Douglas et al. |
| 8,668,910 | B2 | 3/2014 | Bouchard et al. |
| 9,248,242 | B2 | 2/2016 | Verespej et al. |
| 9,427,531 | B2 | 8/2016 | Hourmand et al. |
| 9,566,395 | B2 | 2/2017 | Denny et al. |
| 9,617,345 | B2 | 4/2017 | Berne et al. |
| RE47,123 | E | 11/2018 | Blanc et al. |
| 10,457,739 | B2 | 10/2019 | Berne et al. |
| 11,332,542 | B2 | 5/2022 | Berne et al. |
| 2005/0003403 | A1 | 1/2005 | Rossi et al. |
| 2009/0226444 | A1 | 9/2009 | Rau et al. |
| 2011/0123530 | A1 | 5/2011 | Arron et al. |
| 2012/0225089 | A1 | 9/2012 | Bouchard et al. |
| 2015/0125386 | A1 | 5/2015 | Hansen et al. |
| 2016/0032004 | A1 | 2/2016 | Govindan et al. |
| 2016/0108131 | A1 | 4/2016 | Berne et al. |
| 2016/0159905 | A1 | 6/2016 | Abdiche et al. |
| 2016/0361360 | A1 | 12/2016 | Chang et al. |
| 2017/0166637 | A1 | 6/2017 | Ben-Moshe et al. |
| 2018/0022817 | A1 | 1/2018 | Berne et al. |
| 2020/0069799 | A1* | 3/2020 | Jezek .................. A61K 47/183 |
| 2020/0069814 | A1 | 3/2020 | Zhao et al. |
| 2020/0102401 | A1 | 4/2020 | Berne et al. |
| 2020/0262922 | A1* | 8/2020 | Bhattacharya .......... A61P 35/00 |
| 2021/0261649 | A1 | 8/2021 | Parry |
| 2022/0080053 | A1 | 3/2022 | Allard et al. |
| 2022/0202946 | A1 | 6/2022 | Authelin et al. |
| 2022/0340682 | A1 | 10/2022 | Berne et al. |
| 2023/0087871 | A1 | 3/2023 | Nicolazzi et al. |
| 2023/0149557 | A1 | 5/2023 | Nicolazzi et al. |
| 2023/0151088 | A1 | 5/2023 | Nicolazzi et al. |
| 2023/0181755 | A1 | 6/2023 | Nicolazzi et al. |
| 2024/0226313 | A1 | 7/2024 | Baudat et al. |
| 2024/0424126 | A1 | 12/2024 | Baudat et al. |
| 2025/0041434 | A1 | 2/2025 | Chadjaa et al. |
| 2025/0154250 | A1 | 5/2025 | Chadjaa et al. |

FOREIGN PATENT DOCUMENTS

| | | | | |
|---|---|---|---|---|
| CN | 104918958 | B | 12/2019 | |
| EP | 0125023 | A1 | 11/1984 | |
| EP | 0173494 | A2 | 3/1986 | |
| EP | 0519596 | A1 | 12/1992 | |
| EP | 0592106 | A1 | 4/1994 | |
| EP | 0239400 | B1 | 8/1994 | |
| EP | 2050764 | A1 | 4/2009 | |
| EP | 2979700 | A1 | 2/2016 | |
| EP | 2922875 | B1 | 3/2017 | |
| EP | 3199552 | A1 | 8/2017 | |
| EP | 3243527 | B1 | 6/2019 | |
| EP | 3594243 | A1 | 1/2020 | |
| EP | 3693023 | A1 | 8/2020 | |
| JP | 2016506370 | A | 3/2016 | |
| JP | 2018520140 | A | 7/2016 | |
| JP | 2018520148 | A | 7/2016 | |
| RU | 2607569 | C2 | 1/2017 | |
| RU | 2697522 | C1 | 8/2019 | |
| WO | WO 1981/001145 | A1 | 4/1981 | |
| WO | WO 1987/002671 | A1 | 5/1987 | |
| WO | WO 1987/005330 | A1 | 9/1987 | |
| WO | 88007378 | A1 | 10/1988 | |
| WO | WO 1991/009967 | A1 | 7/1991 | |
| WO | WO 1994/011026 | A2 | 5/1994 | |
| WO | WO 1994/019478 | A1 | 9/1994 | |
| WO | WO 1995/014785 | A1 | 6/1995 | |
| WO | WO 1996/002576 | A1 | 2/1996 | |
| WO | WO 1996/022378 | A1 | 7/1996 | |
| WO | WO 1997/010354 | A1 | 3/1997 | |
| WO | WO 1998/045322 | A2 | 10/1998 | |
| WO | 2004016801 | A2 | 2/2004 | |
| WO | WO 2004/091668 | A1 | 10/2004 | |
| WO | 2005077090 | A2 | 8/2005 | |
| WO | WO 2007/071426 | A1 | 6/2007 | |
| WO | WO 2008/010101 | A2 | 1/2008 | |
| WO | WO 2009/012268 | A1 | 1/2009 | |
| WO | WO 2009/032661 | A1 | 3/2009 | |
| WO | WO 2009/134977 | A1 | 11/2009 | |
| WO | 2011001052 | A1 | 1/2011 | |
| WO | 2011039724 | A1 | 4/2011 | |
| WO | WO 2012/117002 | A1 | 9/2012 | |
| WO | 2014004809 | A2 | 1/2014 | |
| WO | WO 2014/079886 | A1 | 5/2014 | |
| WO | 2014092804 | A1 | 6/2014 | |
| WO | 2014157444 | A1 | 10/2014 | |
| WO | 2015012904 | A2 | 1/2015 | |
| WO | 2015069430 | A2 | 5/2015 | |
| WO | WO 2015/075201 | A1 | 5/2015 | |
| WO | WO 2015/168607 | A2 | 11/2015 | |
| WO | WO 2016/180941 | A1 | 11/2016 | |
| WO | 2016210108 | A1 | 12/2016 | |
| WO | WO-2018204368 | A1 * | 11/2018 | ......... A61K 39/3955 |
| WO | 2018227023 | A1 | 12/2018 | |
| WO | 2020056008 | A1 | 3/2020 | |
| WO | WO 2020/053301 | A1 | 3/2020 | |
| WO | 2020079209 | A1 | 4/2020 | |
| WO | WO 2020/161214 | A1 | 8/2020 | |
| WO | 2020190725 | A1 | 9/2020 | |
| WO | 2020190731 | A1 | 9/2020 | |
| WO | 2020190734 | A1 | 9/2020 | |
| WO | 2020190760 | A1 | 9/2020 | |
| WO | 2020190762 | A1 | 9/2020 | |
| WO | WO 2021/214221 | A1 | 10/2021 | |
| WO | WO 2021/214222 | A1 | 10/2021 | |
| WO | WO 2021/214223 | A1 | 10/2021 | |
| WO | WO 2021/214227 | A1 | 10/2021 | |
| WO | 2024180192 | A1 | 9/2024 | |

(56) References Cited

OTHER PUBLICATIONS

U.S. Appl. No. 14/716,377 2016/0108131 U.S. Pat. No. 9,617,345, filed May 19, 2015 Apr. 21, 2016 Apr. 11, 2017, Pierre-Francois Berne.
U.S. Appl. No. 15/446,465 2018/0022817 U.S. Pat. No. 10,457,739, filed Mar. 1, 2017 Jan. 25, 2018 Oct. 29, 2019, Pierre-Francois Berne.
U.S. Appl. No. 16/558,939 2020/0102401, filed Sep. 3, 2019 Apr. 2, 2020, Pierre-Francois Berne.
U.S. Appl. No. 17/425,603, filed Jul. 23, 2021, Aurore Allard.
Almagro et al. (Jan. 1, 2008) "Humanization of Antibodies", Frontiers in Bioscience, vol. 13, pp. 1619-1633.
Angal, et al., "A Single Amino Acid Substitution Abolishes the Heterogeneity of Chimeric Mouse/Human (IgG4) Antibody", Molecular Immunology, vol. 30, No. 1, pp. 105-108, 1993.
Beers et al. (2010) "Cd20 as a Target for Therapeutic Type I and II Monoclonal Antibodies", Seminars in Hematology, vol. 47, No. 2, pp. 107-114.
Berman et al. (Jan. 1, 2000) "The Protein Data Bank", Nucleic Acids Research, vol. 28, No. 1, pp. 235-242.
Blumenthal et al. (2005) "Inhibition of Adhesion, Invasion, and Metastasis by Antibodies Targeting CEACA", Cancer Research, vol. 65, No. 19, XP055022386, pp. 8809-8817.
Brady et al. (Feb. 1984) "New Cosmid Vectors Developed for Eukaryotic DNA Cloning", Gene vol. 27, Issue 2, pp. 223-232.
Caron et al. (1992) "Biological and Immunological Features of Humanized M195 (Anti-CD33) Monoclonal", Cancer Research, vol. 52, pp. 6761-6767.
Caron et al. (Oct. 1992) "Engineered Humanized Dimeric Forms of IgG Are More Effective Antibodies", Journal of Experimental Medicine, The Rockefeller University Press, vol. 176, pp. 1191-1195.
Cromwell et al. (2006) "Protein Aggregation and Bioprocessing", The AAPS Journal, vol. 8, No. 3, pp. E572-E579.
Decary et al. (Aug. 1, 2015) "Abstract 1688: A Novel Anti-CEACAM5 Maytansinoid-Antibody-Drug Conjugate for the Treatment of Colorectal, Lung and Gastric Tumors", AACR 106th Annual Meeting, Apr. 18-22, 2015, vol. 75, Issue 15, Supplement.
Dimitrov, "Therapeutic Antibodies Methods and Protocols", Methods in Molecular Biology™ book series (MIMB), 2009, vol. 525, 445 Pages, 2009.
Doern et al. (2009) "Characterization of Inhibitory Anti-Insulin-Like Growth Factor Receptor Antibodies with Different Epitope Specificity and Ligand-Blocking Properties: Implications for Mechanism of Action in Vivo", The Journal of Biological Chemistry, vol. 284, No. 15, pp. 10254-10267.
Ebrahimnejad et al. (2000) "Cell Adhesion Molecule CEACAM1 Associates with Paxillin in Granulocytes and Epithelial and Endothelial Cells", Experimental Cell Research, vol. 260, No. 1, pp. 365-373.
Edge et al. (Nov. 15, 1981) "Deglycosylation of glycoproteins by trifluoromethanesulfonic acid", Analytical Biochemistry, vol. 118, No. 1, pp. 131-137.
Extended European Search Report received for European Patent Application No. 17157890.9, mailed on May 24, 2017, 9 Pages.
Extended European Search Report received for European Patent Application No. 20315449.7, mailed on Apr. 29, 2021.
Foote et al. (Mar. 20, 1992) "Antibody Framework Residues Affecting the Conformation of the Hypervariable Loops", Journal of Molecular Biology, vol. 224, No. 2, pp. 487-499.
Gazzano-Santoro et al. (1997) "A Non-Radioactive Complement-Dependent Cytotoxicity Assay for Anti-Cd20 Monoclonal Antibody", Journal of Immunological Methods, vol. 202, No. 2, pp. 163-171.
GE Healthcare (Apr. 2010) "Resolving a Bottleneck in Screening and Characterization of Recombinant Antibody Fragments using Biacore 4000", Application note 28-9777-72 AA, Biacore™ label-free interaction analysis, 6 Pages.
Genbank (Nov. 1, 1994) "Carcinoembryonic Antigen [*Homo sapiens*]", UniProtKB-P06731 (CEAM5_HUMAN), Accession No. AAA51967.1.
Genbank "Carcinoembryonic Antigen-Related Cell Adhesion Molecule 1 Isoform 1 Precursor [*Homo sapiens* ]", Accession No. NP_001703.2.
Genbank "Carcinoembryonic Antigen-Related Cell Adhesion Molecule 6 Precursor [*Homo sapiens*]", Accession No. NP_002474.3.
Genbank "Carcinoembryonic Antigen-Related Cell Adhesion Molecule 7 Precursor [*Homo sapiens*]", Accession No. NP_008821.1.
Genbank "Carcinoembryonic Antigen-Related Cell Adhesion Molecule 8 Precursor [*Homo sapiens*]", Accession No. NP_001807.2.
Gillies et al. (Jul. 1983) "A Tissue-Specific Transcription Enhancer Element is Located in the Major Intron of a Rearranged Immunoglobulin Heavy Chain Gene", Cell, vol. 33, No. 3, pp. 717-728.
Gold et al. (1965) "Demonstration of Tumor-Specific Antigens in Human Colonic Carcinomata by Immunological Tolerance and Absorption Techniques", The Journal of Experimental Medicine, vol. 121, pp. 439-462.
Hammarström et al., "Gastric Cancer—Chapter 31", Tumor Markers: Physiology, Pathobiology, Technology, and Clinical Applications, vol. 382, 2002, pp. 375-382.
Harmsen et al. (2007) "Properties, Production, and Applications of Camelid Single-Domain Antibody Fragments", Application Microbial Biotechnology, vol. 77, No. 1, pp. 13-22.
Henry et al. (Dec. 2015) "Abstract B145: Pk/Pd Evaluation of an Anti-CEACAM5 Antibody Drug Conjugate, in a Colon Patient-Derived-Xenografted Mice Model", AACR-NCI-EORTC International Conference: Molecular Targets and Cancer Therapeutics; Nov. 5-9, 2015; Boston, MA, vol. 14, Issue 12, Supplement 2.
International Search Report and Written Opinion received for PCT Patent Application No. PCT/EP2013/074291, mailed on Feb. 24, 2014, 14 Pages.
International Search Report and Written Opinion received for PCT Patent Application No. PCT/EP2020/052932, mailed Apr. 30, 2020.
Jespers et al. (1994) "Guiding the Selection of Human Antibodies from Phage Display Repertoires to a Single Epitope of An Antigen", Bio/Technology (Nature Publishing Company), vol. 12, No. 9, pp. 899-903.
Julien et al. (2012) "Characterization of a Large Panel of Patient-Derived Tumor Xenografts Representing the Clinical Heterogeneity of Human Colorectal Cancer", Clinical Cancer Research, vol. 18, No. 19, pp. 5314-5328.
Kammerer et al. (2010) "Coevolution of Activating and Inhibitory Receptors Within Mammalian Carcinoembryonic Antigen Families", BMC Biology, vol. 8, No. 12, 21 Pages.
Kilpatrick et al. (Aug. 1997) "Rapid Development of Affinity Matured Monoclonal Antibodies Using RIMMS", Hybridoma, vol. 16, No. 4, pp. 381-389.
Kim, et al., "Immunohistochemistry for Pathologists: Protocols, Pitfalls, and Tips", Journal of Pathology and Translational Medicine, vol. 50, No. 6, pp. 411-418, 2016.
Kranz, et al., "Factors Influencing Polysorbate's Sensitivity Against Enzymatic Hydrolysis and Oxidative Degradation", Journal of Pharmaceutical Sciences, vol. 108, Issue 6, pp. 2022-2032, Jun. 2019.
Kuwana et al. (Dec. 31, 1987) "Expression of Chimeric Receptor Composed of Immunoglobulin-Derived V Regions and T-Cell Receptor-Derived C Regions", Biochemical and Biophysical Research Communications, vol. 149, pp. 960-968.
Langer, "New Methods of Drug Delivery", Science, vol. 249, Issue 4976, pp. 1527-1533, Sep. 28, 1990.
Lefranc et al. (2003) "IMGT Unique Numbering for Immunoglobulin and T Cell Receptor Variable Domains and Ig Superfamily V-like Domains", Developmental & Comparative Immunology, vol. 27, No. 1, pp. 55-77.
Lefranc et al. (2005) "IMGT, The International Immunogenetics information system", Nucleic Acids Research, 2005, pp. D593-D597.
Litzen et al. (1993) "Separation and Quantitation of Monoclonal Antibody Aggregates by Asymmetrical Flow Field-Flow Fractionation and Comparison to Gel Permeation Chromatography", Analytical Biochemistry, vol. 212, No. 2, pp. 469-480.

(56) References Cited

OTHER PUBLICATIONS

Mason et al. (Jun. 1985) "Transcription Cell Type Specificity is Conferred by an Immunoglobulin VH Gene Promoter That Includes a Functional Consensus Sequence", Cell, vol. 41, No. 2, pp. 479-487.
Meehan, et al., "A Microinfusor Device for the Delivery of Therapeutic Levels of Peptides and Macromolecules", Journal of Controlled Release, vol. 46, Issues 1- 2, pp. 107-116, May 5, 1997.
Miyaji et al. (Mar. 1990) "Expression of Human Beta-Interferon in Namalwa KJM-1 Which Was Adapted to Serum-Free Medium", Cytotechnology, vol. 3, No. 2, pp. 133-140.
Mizukami et al. (May 1987) "A New SV40-Based Vector Developed for cDNA Expression in Animal Cells", Journal of Biochemistry vol. 101, No. 5, pp. 1307-1310.
Mohsin et al. (Jul. 23, 2004) "Progesterone Receptor by Immunohistochemistry and Clinical Outcome in Breast Cancer: A Validation Study", Modern Pathology: An Official Journal of the United States and Canadian Academy of Pathology, Inc., pp. 1545-1554.
Monsellier et al. (2006) "Improving the Stability of an Antibody Variable Fragment by a Combination of Knowledge-based Approaches: Validation and Mechanisms", Journal of Molecular Biology, vol. 362, pp. 580-593.
Morrison et al. (1984) "Transfer and Expression of Immunoglobulin Genes", Annual Review of immunology, vol. 2, pp. 239-256.
NCBI (Jun. 20, 2016) "CEACAM5 Carcinoembryonic Antigen Related Cell Adhesion Molecule 5 [ *Homo Sapiens* (Human)", Gene ID: 1048.
Needleman et al. (Mar. 1970) "A General Method Applicable to the Search for Similarities in the Amino Acid Sequence of Two Proteins", Journal of Molecular Biology, vol. 48, No. 3, pp. 443-453.
Neuberger et al. (1985) "A Hapten-Specific Chimaeric IgE Antibody with Human Physiological Effector Function", Nature, 1985, vol. 314, No. 6008, pp. 268-270.
Oberst et al. (2009) "In Vitro Pharmacological Comparison of a Carcinoembryonic Antigen (CEA)/CD3 Bispecific Cynomolgus-Reactive Biosimilar Bite Antibody (Cys111) Biosimilar with The Clinical Candidate Medi-565 (Mt111)", Abstract# 3247: In Proceedings of the 100th American Association for Cancer Research, vol. 50, XP008167243, p. 786.
O'Hare et al. (Mar. 1, 1981) "Transformation of Mouse Fibroblasts to Methotrexate Resistance by a Recombinant Plasmid Expressing a Prokaryotic Dihydrofolate Reductase", Proceedings of National Academy of Sciences, vol. 78, No. 3, pp. 1527-1531.
Padlan, Eduardo A. (Apr.-May 1991) "A Possible Procedure for Reducing the Immunogenicity of Antibody Variable Domains While Preserving Their Ligand Binding Properties", Molecular Immunology, vol. 28, No. 4-5, pp. 489-498.
Peng et al. (2012) "The CEA/CD3-Bispecific Antibody Medi-565 (MT111) Binds a Nonlinear Epitope in the Full-Length But", PloS One, vol. 7, No. 5, XP002719867, pp. e36412.
Peters et al. (Mar. 2005) "The Immune Epitope Database and Analysis Resource: From Vision to Blueprint", Plos Biology, vol. 3, No. 3, e91, pp. 0379-0381.
Plowman et al. (1997) "Human Tumor Xenograft Models in NCI Drug Development", Anticancer Drug Development Guide, pp. 101-125.
Powell, et al., "Compendium of Excipients For Parenteral Formulations", PDA Journal of Pharmaceutical Science and Technology, vol. 52, No. 5, pp. 238-311, Sep. 1, 1998.
Remington et al. "Remington's Pharmaceutical Sciences", 15th Edition, pp. 1035-1038.
Remington et al. "Remington's Pharmaceutical Sciences", 15th Edition, pp. 1570-1580.
Riechmann et al. (1988) "Expression of an Antibody Fv Fragment in Myeloma Cells", Journal of Molecular Biology, vol. 203, No. 3, pp. 825-828.
Riechmann et al. (Mar. 24, 1988) "Reshaping Human Antibodies for Therapy", Nature, vol. 332, No. 6162, pp. 323-327.
Roguska et al. (Feb. 1, 1994) "Humanization of Murine Monoclonal Antibodies Through Variable Domain Resurfacing", Proceedings of the National Academy of Sciences, vol. 91, No. 3, pp. 969-973.
Sanofi, "Evaluation of SAR408701 in Patients With Advanced Solid Tumors", ClinicalTrials.gov Identifier: NCT02187848, Retrieved from:<<https://clinicaltrials.gov/ct2/show/NCT02187848>>, 9 Pages, Jul. 11, 2014.
Sanofi, "SAR408701 Versus Docetaxel in Previously Treated, Carcinoembryonic Antigen-related Cell Adhesion Molecule 5 (CEACAM5) Positive Metastatic Non-squamous Non-small Cell Lung Cancer Patients (CARMEN-LC03)", ClinicalTrials.gov Identifier: NCT04154956, Retrieved from: <<https://clinicaltrials.gov/ct2/show/NCT04154956>>, 9 Pages, Nov. 7, 2019.
Schmidt et al. (2008) "Kinetics of Anti-Carcinoembryonic Antigen Antibody Internalization: Effects of Affinity. Bivalency and Stability", Cancer Immunology Immunotherapy, vol. 57, XP019654564, pp. 1879-1890.
Sharkey et al. (1990) "Murine Monoclonal Antibodies against Carcinoembryonic Antigen: Immunological", Cancer Research, vol. 50, No. 9, pp. 2823-2831.
Sharkey et al. (1995) "Evaluation of a Complementarity-Determining Region-Grafted (Humanized) Anti-Carcinoembryonic Antigen Monoclonal Antibody in Preclinical and Clinical Studies", Cancer Research, vol. 55, pp. 5935s-5945s.
Shirasu, et al. (Jun. 2016) "CEACAM5 (carcinoembryonic antigen-related cell adhesion molecule 5 (carcinoembryonic antigen", Atlas of Genetics and Cytogenetics in Oncology and Haematology, vol. 20, No. 5, pp. 243-249.
Shitara et al. (Jan. 3, 1994) "A New Vector for the High Level Expression of Chimeric Antibodies in Myeloma Cells", Journal of Immunological Methods, vol. 167, No. 1-2, pp. 271-278.
Shopes, (May 1, 1992) "A Genetically Engineered Human IgG Mutant with Enhanced Cytolytic Activity", Journal of Immunology, vol. 148, No. 9, pp. 2918-2922.
Sojar et al. (Nov. 15, 1987) "A Chemical Method for the Deglycosylation of Proteins", Archives of Biochemistry and Biophysics, vol. 259, No. 1, pp. 52-57.
Steipe et al. (Jul. 15, 1994) "Sequence Statistics Reliably Predict Stabilizing Mutations in a Protein Domain", Journal of Molecular Biology, vol. 240, No. 3, pp. 188-192.
Strickland et al. (2009) "Preclinical Evaluation of Carcinoembryonic Cell Adhesion Molecule (CEACAM) 6 as Potential Therapy Target for Pancreatic Adenocarcinoma", The Journal of Pathology, vol. 218, No. 3, pp. 380-390.
Studnicka et al. (Jun. 1, 1994) "Human-Engineered Monoclonal Antibodies Retain Full Specific Binding Activity by Preserving Non-CDR Complementarity-Modulating Residues", Protein Engineering, vol. 7, No. 6, pp. 805-814.
Taylor, et al., "A Transgenic Mouse That Expresses a Diversity of Human Sequence Heavy and Light Chain Immunoglobulins", Nucleic Acids Research, vol. 20, No. 23, pp. 6287-6295, Dec. 11, 1992.
Thotakura et al. (1987) "[28] Enzymatic Deglycosylation of Glycoproteins" Methods in Enzymology. vol. 138, Academic Press, pp. 350-359.
Urlaub et al. (Jul. 1980) "Isolation of Chinese Hamster Cell Mutants Deficient in Dihydrofolate Reductase Activity", Proceedings of the National Academy of Sciences of the United States of America, vol. 77, No. 7, pp. 4216-4220.
Vitetta et al. (1987) "Interaction and Activation of Antigen-Specific T and B Cells", Immunological Reviews, vol. 99, Issue 1, pp. 193-239.
Vitetta et al. (1987) "Redesigning Nature's Poisons to Create Anti-Tumor Reagents", Science, vol. 238, No. 4830, pp. 1098-1104.
Wang et al. (2008) "Fractionation of Monoclonal Antibody Aggregates Using Membrane Chromatography", Journal of Membrane Science, vol. 318, No. 1-2, pp. 311-316.
Wennerberg et al. (1993) "Hepatocyte Paraffin 1: A Monoclonal Antibody That Reacts with Hepatocytes and Can Be Used for Differential Diagnosis of Hepatic Tumors", The American Journal of Pathology, vol. 143, No. 4, pp. 1050-1054.
Wu, et al., "Receptor-mediated in Vitro Gene Transformation by a Soluble DNA Carrier System", The Journal of Biological Chemistry, vol. 262, No. 10, pp. 4429-4432, Apr. 1987.

(56) References Cited

OTHER PUBLICATIONS

Zhang et al. (Aug. 23, 2011) "Epitope Mapping of A 95 kDa Antigen in Complex with Antibody by Solution-Phase Amide Backbone Hydrogen/Deuterium Exchange Monitored by Fourier Transform Ion Cyclotron Resonance Mass Spectrometry", Analytical Chemistry, vol. 83, No. 18, pp. 7129-7136.
Zhao et al. (2004) "An Enzyme-Linked Immunosorbent Assay for Human Carcinoembryonic Antigen-Related Cell Adhesion Molecule 8, A Biological Marker of Granulocyte Activities In Vivo", Journal of Immunological Methods, vol. 293, Issues 1-2, pp. 207-214.
U.S. Appl. No. 17/916,737, filed Oct. 3, 2022, Céline Nicolazzi, Antitumor Combinations Containing Anti-CEACAM5 Antibody Conjugates, Trifluridine and Tipiracil.
U.S. Appl. No. 17/916,877, filed Oct. 4, 2022, Céline Nicolazzi, Antitumor Combinations Containing Anti-Ceacam5 Antibody Conjugates and Folfiri.
U.S. Appl. No. 17/917,064, filed Oct. 5, 2022, Céline Nicolazzi, Antitumor Combinations Containing Anti-Ceacam5 Antibody Conjugates and Cetuximab.
U.S. Appl. No. 17/917,375, filed Apr. 22, 2021, Céline Nicolazzi, Antitumor Combinations Containing Anti-Ceacam5 Antibody Conjugates and Folfox.
Blumenthal et al., "Carcinoembryonic antigen antibody inhibits lung metastasis and augments chemotherapy in a human colonic carcinoma xenograft", Cancer Immunol. Immunother., Apr. 2005, 54(4): 315-327.
Clinicaltrials.gov, "History of Changes for Study: NCT03324113 Evaluation of SAR408701 in Combination With Other Anti-tumor Drug in Japanese Patients With Advanced Malignant Solid Tumors", Jan. 15, 2019.
Decary et al., "Abstract 1688: A novel anti-CEACAM5 maytansinoid-antibody-drug conjugate for the treatment of colorectal, lung and gastric tumors", Cancer Research, Aug. 1, 2015, 75(15 Suppl.): 1688.
European Search Report for European Patent Applicaton No. 2020031521.8, dated Oct. 8, 2020.
Govindan et al., "Improving the Therapeutic Index in Cancer Therapy by Using Antibody-Drug Conjugates Designed with a Moderately Cytotoxic Drug", Molecular Pharmaceutics, Jun. 1, 2015, 12(6): 1836-1847.
International Search Report and Written Opinion received for PCT Patent Application No. PCT/EP2021/060535, dated Jul. 26, 2021.
International Search Report and Written Opinion received for PCT Patent Application No. PCT/EP2021/060537, dated Jul. 26, 2021.
International Search Report and Written Opinion received for PCT Patent Application No. PCT/EP2021/060542, dated Jul. 26, 2021.
International Search Report and Written Opinion received for PCT Patent Application No. PCT/EP2021/060, dated.
Iveson et al., "Review of metastatic colorectal cancer treatment pathways and early clinical experience of trifluridine/tipiracil in the UK named patient programme", BMC Cancer, Feb. 3, 2020, 20(91): 1-8.
Liersch, "Safety and efficacy of repeated anJournal of Oncologyti-CEA radioimmunotherapy (RAIT) with 131I-labetuzumab post salvage resection of colorectal liver metastases", Journal of Oncology, 25(18 suppl), Meeting Abstract, Jun. 20, 2007, ASCO Annual Meeting, Tumor Biology and Human Genetics.
Magge, "Antibody drug conjugate shows promise for metastatic colorectal cancer", Oct. 10, 2017, Retrieved from the Internet: URL: https://www.healio.com/news/hematology-oncology/20171010/antibody-drug-conjugate-shows-pr.omise-for-metastatic-colorectal-cancer.
Wilson, "Novel Therapeutic Developments Other Than EGFR and VEGF Inhibition in Colorectal Cancer", Oncologist, Oct. 1, 2006, 11(9): 1018-1024.
Zheng et al., "A Novel Anti-CEACAM5 Monoclonal Antibody, CC4, Suppresses Colorectal Tumor Growth and Enhances NK Cells-Mediated Tumor Immunity", PLOS One, Jun. 2011, 6(6): e21146.
U.S. Appl. No. 15/446,465 2018/0022817 U.S. Pat. No. 10,457,739, filed Mar. 1, 2017 Jan. 25, 2018 Ocy. 29, 2019, Pierre-Francois Berne.
U.S. Appl. No. 16/558,939 2020/0102401 U.S. Pat. No. 11,332,542, filed Sep. 3, 2019 Apr. 2, 2020 May 17, 2022, Pierre-Francois Berne.
U.S. Appl. No. 17/705,016, filed Mar. 25, 2022, Pierre-Francois Berne.
U.S. Appl. No. 17/425,603 2022/0080053, filed Jul. 23, 2021 Mar. 17, 2022, Aurore Allard.
U.S. Appl. No. 17/916,737, filed Oct. 3, 2022, Céline Nicolazzi.
U.S. Appl. No. 17/916,877, filed Oct. 4, 2022, Céline Nicolazzi.
U.S. Appl. No. 17/917,064, filed Oct. 5, 2022, Céline Nicolazzi.
Clinicaltrials.gov, "SAR408701 in Combination With Ramucirumab in Pre-treated Patients With Non Squamous Non-small Cell Lung Cancer (NSQ NSCLC) (CARMEN-LC04)", May 19, 2020.
International Search Report and Written Opinion received for PCT Patent Application No. PCT/EP2021/081038, dated Feb. 8, 2022.
Sanofi, "Clinical Trials Appendices", Jul. 29, 2020, Retrieved from url: https://www.sanofi.com/dam/jcr:5aa069ad-47d7-43db-a46b-fdc22b1dc7a3/2020_07_29_Q2_2020_RD_Appendix.pdf, p. 59, SAR408701.
U.S. Appl. No. 14/716,377 2016/0108131, U.S. Pat. No. 9,617,345, filed May 19, 2015 Apr. 21, 2016 Apr. 11, 2017, Pierre-Francois Berne, Anti-CEACAM5 Antibodies and Uses Thereof.
U.S. Appl. No. 15/446,465 2018/0022817 U.S. Pat. No. 10,457,739, filed Mar. 1, 2017 Jan. 25, 2018 Oct. 29, 2019, Pierre-Francois Berne, Anti-CEACAM5 Antibodies and Uses Thereof.
U.S. Appl. No. 16/558,939 2020/0102401 U.S. Pat. No. 11,332,542, filed Sep. 3, 2019 Apr. 2, 2020 May 17, 2022, Pierre-Francois Berne, Anti-CEACAM5 Antibodies and Uses Thereof.
U.S. Appl. No. 17/705,016 2022/0340682, filed Mar. 25, 2022 Oct. 27, 2022, Pierre-Francois, Berne, Anti-CEACAM5 Antibodies and Uses Thereof.
U.S. Appl. No. 17/425,603 2022/0080053, filed Jul. 23, 2021 Mar. 17, 2022, Aurore Allard, Use of Anti-CEACAM5 Immunoconjugates for Treating Lung Cancer.
U.S. Appl. No. 17/916,737 2023/0181755, filed Oct. 3, 2022 Jun. 15, 2023, Céline Nicolazzi, Antitumor Combinations Containing Anti-CEACAM5 Antibody Conjugates, Trifluridine and Tipiracil.
U.S. Appl. No. 17/916,877 2023/0087871, filed Oct. 4, 2022 Mar. 23, 2023, Céline Nicolazzi, Antitumor Combinations Containing Anti-CEACAM5 Antibody Conjugates and Folfiri.
U.S. Appl. No. 17/917,064 2023/0149557, filed Oct. 5, 2022 May 18, 2023, Céline Nicolazzi, Antitumor Combinations Containing Anti-CEACAM5 Antibody Conjugates and Cetuximab.
U.S. Appl. No. 17/917,375 2023/0151088, filed Apr. 22, 2021 May 18, 2023, Céline Nicolazzi, Antitumor Combinations Containing Anti-CEACAM5 Antibody Conjugates and Folfox.
Adumeau et al., "Thiol-reactive bifunctional chelators for the creation of site-selectively modified radioimmunoconjugates with improved stability," Bioconjugate Chemistry, vol. 29, No. 4., Apr. 18, 2018, pp. 1364-1372.
Agarwal et al., "Hydrazino-Pictet-Spengler ligation as a biocompatible method for the generation of stable protein conjugates," Bioconjugate Chem, vol. 24, No. 6, May 28, 2013, pp. 846-851.
Agarwal et al., "Site-Specific Antibody-Drug Conjugates: The Nexus of Bioorthogonal Chemistry, Protein Engineering, and Drug Development," Bioconjugate Chem., vol. 26, 2015 (Published Dec. 12, 2014), pp. 176-192.
Author Unknown, structure for CAS number [352439-36-2] —azido-PEG8-OH, Chemical Book Product Catalog, 2016; retrieved from https://www.chemicalbook.com/ProductCatalog_EN/201271.htm; Jun. 12, 2024, 8 pages.
Author Unknown, structure for CAS number [642473-95-8] —3M-012, GLPBio Technology Product Catalog, 2017, retrieved from https://www.glpbio.com/tlr7-8-agonist-3.html Jun. 12, 2024, 5 pages.
Axup et al., "Synthesis of site-specific antibody-drug conjugates using unnatural amino acids," PNAS, vol. 109, No. 40, Oct. 2, 2012, pp. 16101-16106.
Burema, Shiri (PCT Authorized Officer), International Search Report and Written Opinion for International Application No. PCT/EP2021/060535 dated Jul. 26, 2021, 15 pages.

(56) References Cited

OTHER PUBLICATIONS

Behrens et al., "Antibody-Drug Conjugates (ADCs) Derived from Interchain Cysteine Cross-Linking Demonstrate Improved Homogeneity and Other Pharmacological Properties over Conventional Heterogeneous ADCs," Molecular Pharmaceutics, vol. 12, No. 11, Nov. 2, 2015, pp. 3986-3998.
Berillon, Laurent (EP Examiner), Extended European Search Report dated Mar. 9, 2022 for European Application No. 21306412.4, 8 pages.
Berillon, Laurent (PCT Authorized Officer), International Search Report and Written Opinion of the International Searching Authority dated Jan. 31, 2023 for International Application No. PCT/EP2022/077804, 13 pages.
Bryant et al., "In Vitro and In Vivo Evaluation of Cysteine Rebridged Trastuzumab-MMAE Antibody Drug Conjugates with Defined Drug-to-Antibody Ratios," Molecular Pharmaceutics, vol. 12, No. 6, 2015 (Published Apr. 20, 2015), pp. 1872-1879.
Author Unknown, Cas Registry No. 2254086-60-5, USAN (JK-225): Tusamitamab Ravtansine, Sponsor: Sanofi, Code Designations: SAR408701, UNII: DSS3BE2ZXN, Nov. 24, 2021, 2 pages.
Chang, C.-H., et al., "Combination Therapy with Bispecific Antibodies and PD-1 Blockade Enhances the Antitumor Potency of T Cells," Cancer Research, vol. 77, No. 19, Aug. 17, 2017, pp. 5384-5394, XP055542212, US ISSN: 0008-5472, DOI: 10.1158/0008-5472.CAN-16-3431.
Chapman, Rob (PCT Authorized Officer), International Search Report for International Application No. PCT/EP2022/084105, dated Feb. 14, 2023, 8 pages.
Chapman, Rob (PCT Authorized Officer), International Search Report for International Application No. PCT/EP2022/080776, dated Feb. 13, 2023, 6 pages.
Criscitiello et al., "Antibody-drug conjugates in solid tumors: a look into novel targets," Journal of Hematology & Oncology, vol. 14, No. 1, Jan. 28, 2021, doi: 10.1186/s13045-021-01035-z, 18 pages.
Edelman et al., "The Covalent Structure of an Entire yG Immunoglobulin Molecule," Proc. Natl. Acad. USA, vol. 63, May 1969, pp. 78-85.
Eisenhauer, E.A., et al., "New response evaluation criteria in solid tumours: Revised RECIST guideline (Version 1.1)," Eur. J. Cancer, vol. 45, No. 2, Jan. 2009, pp. 228-247.
Gandhi, L., et al., "Pembrolizumab plus Chemotherapy in Metastatic Non-Small-Cell Lung Cancer," New England Journal of Medicine, vol. 378, No. 22, May 31, 2018 (Published Apr. 16, 2018), pp. 2078-2092.
Garnett, "Targeted drug conjugates: principles and progress," Advanced Drug Delivery Reviews, vol. 53, Issue 2, Dec. 17, 2001, pp. 171-216.
Author Unknown, Genbank Accession No. AAK62676 for murine TLR7 polypeptide; Jul. 15, 2002, 3 pages.
Author Unknown, Genbank Accession No. AAK62677 for murine TLR8 polypeptide; Jul. 15, 2002, 3 pages.
Author Unknown, Genbank Accession No. AAZ95441 for human TLR8 polypeptide; Nov. 25, 2009, 3 pages.
Author Unknown, Genbank Accession No. AAZ99026 for human TLR7 polypeptide; Nov. 25, 2009, 3 pages.
Gold, P., et al., "Specific carcinoembryonic antigens of the human digestive system," Journal of Experimental Medicine, vol. 122, No. 3, Sep. 1, 1965, pp. 467-481.
Hammarström, S., "The carcinoembryonic antigen (CEA) family: structures, suggested functions and expression in normal and malignant tissues," Seminars in Cancer Biology, vol. 9, Issue 2, Apr. 1999, pp. 67-81.
Hermanson, G.T. (2008) Bioconjugate Techniques. 2nd Edition, Academic Press, London, 1323.
Hudak et al., "Synthesis of Heterobifunctional Protein Fusions Using Copper-Free Click Chemistry and the Aldehyde Tag," Angewandte Chemie, International Edition, vol. 51, 2012 (Published online Mar. 12, 2012), pp. 4161-4165.
Jeger et al., "Site-Specific and Stoichiometric Modification of Antibodies by Bacterial Transglutaminase," Angewandte Chemie, International Edition, vol. 10, 2010 (Published online Nov. 25, 2010), pp. 9995-9997.
Junutula et al., "Site-specific conjugation of a cytotoxic drug to an antibody improves the therapeutic index," Nature Biotechnology, vol. 26, No. 8, Aug. 2008 (Published online Jul. 20, 2008), pp. 925-932 (9 pages total).
Kabat et al., Sequences of proteins of immunological interest. 5th Edition—US Department of Health and Human Services, NIH Publication No. 91-3242, 1991, pp. 662, 680 and 689.
Lunter, Pim (PCT Authorized Officer), International Search Report and Written Opinion of the International Searching Authority dated Mar. 14, 2023 for International Application No. PCT/EP2022/084107.
Johnson, et al., "Phase III trial comparing antibody-drug conjugate (ADC) SAR408701 with docetaxel in patients with metastatic non-squamous non-small cell lung cancer (NSQ NSCLC) failing chemotherapy and immunotherapy," Journal of Clinical Oncology, vol. 38, No. 15., 2020 , ASCO Meeting Abstract, 4 pages.
Mok, Tony S.K., et al., "Pembrolizumab versus chemotherapy for previously untreated, PD-L1-expressing, locally advanced or metastatic non-small-cell lung cancer (KEYNOTE-042): a randomised, open-label, controlled, phase 3 trial," The Lancet, vol. 393, Issue 10183, 4 May , 2019, pp. 1819-1830, epub Apr. 4, 2019.
Author Unknown, National Center for Biotechnology Information (2024). PubChem Compound Summary for CID 4614742, 2-[2-[2-(2-Azidoethoxy)ethoxy]ethoxy]ethanol (CAS No. 86770-67-4). Retrieved Jun. 12, 2024 from https://pubchem.ncbi.nlm.nih.gov/compound/Azido-PEG4-alcohol; created Sep. 16, 2005, 15 pages.
Author Unknown, NCBI—National Center for Biotechnology Information (2024), PubChem Compound Summary for CID 10940805, Azide-PEG12-alcohol (CAS number [1821464-55-4), retrieved Jun. 12, 2024 from https://pubchem.ncbi.nlm.nih.gov/compound/Azide-PEG12-alcohol; created Oct. 26, 2006, 11 pages.
Author Unknown, NCBI—National Center for Biotechnology Information (2024), PubChem Compound Summary for CID 135403648, 5-Formyltetrahydrofolic acid (CAS No. 58-05-9, Leucovorin (Folinic acid) —C20H23N2O7), retrieved Aug. 1, 2024 from https://pubchem.ncbi.nlm.nih.gov/compound/135403648, created Jan. 15, 2019, 71 pages.
Author Unknown, NCBI—National Center for Biotechnology Information (2024), PubChem Compound Summary for CID 159603, Resiquimod (CAS No. 144875-48-9), retrieved Jun. 12, 2024 from https://pubchem.ncbi.nlm.nih.gov/compound/Resiquimod, created Aug. 1, 2005, 33 pages.
Author Unknown, NCBI—National Center for Biotechnology Information (2024), PubChem Compound Summary for CID 3385, 5-Fluorouracil (CAS No. 51-21-8, Fluorouracil —C4H3FN2O2), retrieved Aug. 1, 2024 from https://pubchem.ncbi.nlm.nih.gov/compound/3385, created Mar. 25, 2005, 121 pages.
Author Unknown, NCBI—National Center for Biotechnology Information (2024), PubChem Compound Summary for CID 60838, (+)-Irinotecan (CAS No. 97682-44-5, Irinotecan—C33H38N406), retrieved Aug. 1, 2024 from https://pubchem.ncbi.nlm.nih.gov/compound/60838, created Jun. 24, 2005, 79 pages.
Author Unknown, NCBI—National Center for Biotechnology Information (2024), PubChem Compound Summary for CID 6256, 5-Trifluorothymidine (CAS No. 70-00-8, Trifluridine—C10H1F3N2O5), retrieved Aug. 1, 2024 from https://pubchem.ncbi.nlm.nih.gov/compound/6256, created Jun. 24, 2005, 75 pages.
Author Unknown, NCBI—National Center for Biotechnology Information (2024), PubChem Compound Summary for CID 6323366, 5-chloro-6-[(2-iminopyrrolidin-1-yl)methyl]-1H-pyrimidine-2,4-dione (CAS No. 183204-71-2, Tipiracil—C9H1ClN402), retrieved Aug. 1, 2024 from https://pubchem.ncbi.nlm.nih.gov/compound/6323266, created Nov. 29, 2005, 35 pages.
Author Unknown, NCBI—National Center for Biotechnology Information (2024), PubChem Compound Summary for CID 78798 (CAS No. 5117-19-1) 3,6,9, 12, 15, 18,21-Heptaoxatricosane-1,23-diol, retrieved Jun. 12, 2024 from https://pubchem.ncbi.nlm.nih.gov/compound/Octaethylene-glycol, created Mar. 27, 2005, 33 pages.

(56) References Cited

OTHER PUBLICATIONS

Author Unknown, NCBI—National Center for Biotechnology Information (2024), PubChem Compound Summary for CID 8200, Tetraethylene glycol, (CAS No. 112-60-7), retrieved Jun. 12, 2024 from https://pubchem.ncbi.nlm.nih.gov/compound/Tetraethylene-glycol, created Mar. 26, 2005, 80 pages.
Author Unknown, NCBI—National Center for Biotechnology Information (2024), PubChem Substance Record for SID 17397410, Trastuzumab (USAN/INN), Source: KEGG, retrieved Jun. 12, 2024 from https://pubchem.ncbi.nlm.nih.gov/substance/17397410, deposited Nov. 22, 2006; structure for SID 17397410 (CAS No. 180288-69-1—Herceptin®), deposited Nov. 22, 2006, retrieved from https://www.genome.jp/entry/D03257 Jun. 12, 2024, 8 pages.
Author Unknown, NCBI—National Center for Biotechnology Information (2024), PubChem Substance Record for SID 17397595, Cetuximab (USAN/INN), Source: KEGG; retrieved Jun. 12, 2024 from https://pubchem.ncbi.nlm.nih.gov/substance/17397595, deposited Nov. 22, 2006; structure for SID 17397595 (CAS No. 205923-56-4—Erbitux®) retrieved from https://www.genome.jp/entry/D03455 Jun. 12, 2024, 7 pages.
Author Unknown, NCBI—National Center for Biotechnology Information (2024), PubChem Substance Record for SID 405226618, Enoblituzumab (USAN/INN), Source: KEGG; retrieved Jun. 12, 2024 from https://pubchem.ncbi.nlm. nih.gov/substance/405226618, deposited May 18, 2020; structure for SID 405226618 (CAS No. 1353485-38-7-Enoblituzumab) retrieved from https://www.genome.jp/entry/D11752 Jun. 12, 2024, 5 pages.
Author Unknown, NCBI—National Center for Biotechnology Information (2024), PubChem Substance Record for SID 481155577, Tusamitamab, Source: BOC Sciences, retrieved Jun. 12, 2024 from https://pubchem.ncbi.nlm.nih.gov/substance/481155577, May 11, deposited 2023, structure for SID 481155577 (CAS No. 2349294-95-5—Tusamitamab) retrieved from https://www.genome.jp/entry/D12309, Jun. 12, 2024, 5 pages.
Genbank "Carcinoembryonic Antigen-Related Cell Adhesion Molecule 7 Preproprotein [*Homo sapiens*]," Accession No. NP 008821. 1, Feb. 26, 2014, 4 pages.
Burema, Shiri (PCT Authorized Officer), International Search Report and Written Opinion for International Application No. PCT/EP2020/052932 dated Apr. 30, 2020, 13 pages.
Patel et al., "BDB001, an intravenously administered toll-like receptor 7 and 8 (TLR7/8) agonist, in combination with pembrolizumab in advanced solid tumors: Phase 1 safety and efficacy results," Journal of Clinical Oncology, vol. 39, Issue 15, Suppl. 2512, May 28, 2021, Abstract and Poster provided, https://doi.org/10.1200/JCO.2021.39.15_suppl.2512.
Patel et al., "BDB001, an intravenously administered toll-like receptor 7 and 8 (TLR7/8) agonist, in combination with pembrolizumab in advanced solid tumors: Phase 1 safety and efficacy results," presented at the ASCO Annual Meeting, 2021, poster retrieved from https://meetings.asco.org/abstracts-presentations/196042 Jun. 25, 2024.
Swinyard E.A. "Analgesics and Antipyretics". In: Remington's Pharmaceutical Sciences, 15th Edition, Hoover, J. E. (ed.). Easton, PA: Mack Publishing Co., 1975, 9 pages.
King, R.E., "Tablet's Capsules and Pills (pp. 1576-1580)" and Author not listed, "Chapter 88: Powders (pp. 1570-1575)" In: Remington's Pharmaceutical Sciences, 15th Edition, Hoover, J. E. (ed.) Easton, PA: Mack Publishing Co., 1975.
Sahlmann, Md, C.-O., et al., "Repeated Adjuvant Anti-CEA Radioimmunotherapy After Resection of Colorectal Liver Metastases: Safety, Feasibility, and Long-Term Efficacy Results of a Prospective Phase 2 Study," Cancer, vol. 123, Feb. 15, 2017 (Published online Oct. 20, 2016), pp. 638-649.
Author Unknown, SANOFI, "Tusamitamab Ravtansine (SAR408701) in Combination With Pembrolizumab and Tusamitamab Ravtansine (SAR408701) in Combination with Pembrolizumab and Platinum-based Chemotherapy With or Without Pemetrexed in Patients With NSQ NSCLC (CARMEN-LC05) (CARMEN-LC05)," NCTO4524689, Updated May 18, 2022, Retrieved from the Internet: URL: https://clinicaltrials.gov/ct2/show/NCT04524689 on May 19, 2022.
Schofield, D.J., et al., "Activity of murine surrogate antibodies for durvalumab and tremelimumab lacking effector function and the ability to deplete regulatory T cells in mouse models of cancer," MABS, vol. 13, Issue 1, 2021 e1857100, 18 pages.
Segal, N.H., et al., "Abstract LB-159: A Phase I study of IMMU-130 (labetuzumab-SN38) anti-CEACAM5 antibody- drug conjugate (ADC) in patients with metastatic colorectal cancer (mCRC)," Cancer Research, vol. 73, LB-159, Apr. 15, 2013, 2 pages.
Singh et al., "Antibody-Cytotoxic Agent Conjugates: Preparation and Characterization," In: Therapeutic Antibodies: Methods and Protocols . (A. Dimitrov (Ed.). New York, NY: Humana Press, 2009, 28 pages.
Strop et al., "Location Matters: Site of Conjugation Modulates Stability and Pharmacokinetics of Antibody Drug Conjugates, " Chemistry & Biology, vol. 20, No. 2, Feb. 21, 2013, pp. 161-167.
Thompson, J.A., "Molecular Cloning and Expression of Carcinoembryonic Antigen Gene Family Members," Tumor Biology, vol. 16, No. 1, 1995, pp. 10-16.
Verma, S., et al., "Trastuzumab Emtansine for HER2-Positive Advanced Breast Cancer," The New England Journal of Medicine, vol. 367, No. 19, Nov. 8, 2012, pp. 1783-1791.
Wittmann-Regis, Agnes (PCT Authorized Officer), International Preliminary Report on Patentability and Written Opinion of the International Searching Authority for International Application No. PCT/EP2013/074291 dated May 26, 2015, 9 pages.
Wittmann-Regis, Agnes (PCT Authorized Officer), International Preliminary Report on Patentability and Written Opinion of the International Searching Authority for International Application No. PCT/EP2022/080776, dated May 2, 2024, 7 pages.
Younes, A., et al., "Results of a Pivotal Phase II Study of Brentuximab Vedotin for Patients With Relapsed or Refractory Hodgkin's Lymphoma," Journal of Clinical Oncology, vol. 30, No. 18, Jun. 20, 2012, pp. 2183-2189.
Zarogoulidis, K., et al., "Treatment of non-small cell lung cancer (NSCLC)," Journal of Thoracic Disease, vol. 5, Suppl. 4, Sep. 2013, pages S389-S396.
Zhou et al., "Site-Specific Antibody-Drug Conjugation through Glycoengineering," Bioconjugate Chem., vol. 25, No. 3, Feb. 17, 2014, pp. 510-520.
Burema, Shiri (EP Examiner), European Search Report for European Patent Applicaton No. 20315218, dated Oct. 8, 2020, 5 pages.
Colucci, G. et al., "Phase III Randomized Trial of FOLFIRI Versus FOLFOX4 in the Treatment of Advanced Colorectal Cancer: A Multicenter Study of the Gruppo Oncologico Dell'italia Meridionale," Journal of Clinical Oncology, Aug. 1, 2005, pp. 4866-4875, vol. 23, No. 22.
Daugherty, A. L. et al., "Formulation and delivery issues for monoclonal antibody therapeutics," Advanced Drug Delivery Reviews, 2006, pp. 686-706, vol. 58, Nos. 5-6.
Pertsev I.M. Pharmaceutical and biomedical aspects of drugs: in 2 volumes. T. 1.—Kharkov: UkrFA. 1999. p. 253-255 of 464 (see English translation of Office Action dated Sep. 27, 2024 from Russian Application No. 2022130335 for a concise explanation of relevance).
Russian Search Report dated Sep. 27, 2024 issued in corresponding Russian Patent Application No. 2022130335, 3 pages (English translation).
Author Unknown (RU Examiner), Russian Search Report dated Aug. 29, 2024 for Russian Application No. 2022127325, 2 pages (English translation).
Trail P. A. "Antibody drug conjugates as cancer therapeutics," Antibodies, 2013, pp. 113-129, vol. 2, No. 1, obtained Dec. 18, 2024 at URL: https://www.mdpi.com/2073-4468/2/1/113.
Author Unknown (CN Examiner), Chinese Search Report for Chinese Patent Application No. 202180030342.6 dated Aug. 29, 2024, 3 pages (English translation only provided).
Author Unknown (RU Examiner), Russian Office Action and Search Report for Russian Application No. 2023115205 dated Feb. 14, 2025, 18 pages (English Translation only provided).
Author Unknown (RU Examiner), Russian Office Action and Search Report dated Sep. 27, 2024 for Russian Application No. 2022130335, 13 pages (English translation only provided).

(56) References Cited

OTHER PUBLICATIONS

Author Unknown (TW Examiner), Taiwan Search Report for Taiwan Patent Application No. 110114496 dated Nov. 26, 2024, 1 page (English translation only provided).
Author Unknown, "OFS. 1.1.0001.18—Rules for the use of pharmacopoeial articles," State Pharmacopoeia of the Russian Federation, XIV Ed., vol. 1, 2018, pp. 122-127 (p. 125 only provided) [see the English Translation of the Russian Office Action dated Feb. 14, 2025 for Russian Application No. 2023115205 for a concise explanation of relevance].
Burema, Shiri (PCT Authorized Officer), International Search Report and Written Opinion for International Application No. PCT/EP2021/060536 dated Jul. 26, 2021, 11 pages.
Chen, Chengwei, et al., "Drugs and Toxic Liver Diseases," 2nd Edition, Shanghai Science and Technology Press, Jan. 31, 2013, pp. 777-779 (4 pages provided) [See Cuilian Peng (CN Examiner), Supplementary Search Report issued Feb. 14, 2025 for Chinese Patent Application No. 202180030566.7 for explanation of relevance].
Chen, Zhiwu, et al., Pharmacology Henan Science and Technology Press , Jan. 31, 2013, pp. 294-295 (3 pages provided) [See Cuilian Peng (CN Examiner), Supplementary Search Report issued Feb. 14, 2025 for Chinese Patent Application No. 202180030566.7 for explanation of relevance].
Govindan et al., "CEACAM5-Targeted Therapy of Human Colonic and Pancreatic Cancer Xenografts with Potent Labetuzumab-SN-38 Immunoconjugates," Clinical Cancer Research, vol. 15, No. 19, Oct. 1, 2009, pp. 6052-6061.
Hoffmann et al., "Antibody structure and engineering considerations for the design and function of Antibody Drug Conjugates (ADCs)," Oncoimmunology, vol. 7, No. 3, 2018 (Published online Nov. 20, 2017), pp. e1395127-1-e1395127-11.
Jiang, Yuan, Pharmaceutical Biotechnology, People's Health Publishing House, Dec. 31, 1996, p. 164 (2 pages provided) [See Cuilian Peng (CN Examiner), Supplementary Search Report issued Feb. 14, 2025 for Chinese Patent Application No. 202180030566.7 for explanation of relevance].
Jorgensen et al., "Recent trends in stabilizing peptides and proteins in pharmaceutical formulation—considerations in the choice of excipients," Expert Opinion on Drug Delivery, vol. 6, Issue 11, 2009 (Published online Aug. 13, 2009), pp. 1219-1230 [See Author Unknown (Ru Examiner), Russian Office Action and Search for Russian Application No. 2023115205 dated Feb. 14, 2025 for explanation of relevance].
Kahl, K., "Antibody drug conjugate shows promise for metastatic colorectal cancer," and Magge, D.R., "Perspective" Oct. 10, 2017, 3 pages, Retrieved from the Internet on Jun. 15, 2025 from https://www.healio.com/news/hematology-oncology/20171010/antibody-drug-conjugate-shows-promise-for-metastatic-colorectal-cancer.
Livesey, Geoffrey, "Health potential of polyols as sugar replacers, with emphasis on low glycaemic properties," Nutrition Research Reviews, vol. 16, 2003, pp. 163-191.
Mohan, Chandra, "Buffers. A Guide for the Preparation and Use of Buffers in Biological Systems," Calbiochem® Biochemicals, Emd CB0052-2006 Usd Buffers Booklet, Aug. 2006, 39 pages.
Mohelnikova-Duchonova et al., "FOLFOX/FOLFIRI Pharmacogenetics: The call for a personalized approach in colorectal cancer therapy," World Journal of Gastroenterology, vol. 20, No. 30, Aug. 14, 2014, pp. 10316-10330.
Nair et al., "A simple practice guide for dose conversion between animals and human," Journal of Basic and Clinical Pharmacy, vol. 7, Issue 2, March-May 2016, pp. 27-31.
NCBI—National Center for Biotechnology Information (2024). PubChem Compound Summary for CID 4620597, NSuccinimidyl 3-maleimidopropionate (CAS No. 55750-62-4). Retrieved Jun. 12, 2024 from https://pubchem.ncbi.nlm.nih.gov/compound/N-Succinimidyl-3-maleimidopropionate; created Sep. 16, 2005, 21 pages.
NCBI—National Center for Biotechnology Information (2024). PubChem Compound Summary for CID 77078258, DBCO-amine (CAS No. 1255942-06-3). Retrieved Jun. 12, 2024 from https://pubchem.ncbi.nlm.nih.gov/compound/DBCO-amine; created Sep. 5, 2014, 18 pages.
Peng, Cuilian (CN Examiner), Supplementary Search Report issued Feb. 14, 2025 for Chinese Patent Application No. 202180030566.7 (English translation only provided).
Peng, Cuilian (CN Examiner), Supplementary Search Report issued Feb. 17, 2025 for Chinese Patent Application No. 202180029921.9 (English translation only provided).
Pertsev, I.M., Pharmaceutical and biomedical aspects of drugs: in 2 volumes. T. 1.—Kharkov: UkrFA, 1999, pp. 253-255 of 464 [see English translation of Office Action dated Sep. 27, 2024 from Russian Application No. 2022130335 for a concise explanation of relevance and Author Unknown (Ru Examiner), Russian Office Action and Search Report for Russian Application No. 2023115205 dated Feb. 14, 2025 for explanation of relevance].
Peters, Godefridus J., "Therapeutic potential of TAS-102 in the treatment of gastrointestinal malignancies," Therapeutic Advances in Medical Oncology, vol. 7, No. 6, Nov. 2015, pp. 340-356.
Reckamp et al., "Phase II Randomized Study of Ramucirumab and Pembrolizumab Versus Standard of Care in Advanced Non-Small-Cell Lung Cancer Previously Treated With Immunotherapy-Lung-MAP S1800A," Journal of Clinical Oncology, vol. 40, Issue 21, 2022 (Available online Jun. 3, 2022), pp. 2295-2307 (18 pages total).
Rowe et al. (Editors), "Handbook of Pharmaceutical Excipients," Sixth Edition, Pharmaceutical Press and American Pharmacists Association, 2009, pp. 242-243 and 247-248 (6 pages total).
Sanofi, "Evaluation of SAR408701 in Japanese Patients With Advanced Malignant Solid Tumors," (Official Title: "A Phase I/Ib Study to Evaluate Safety and Pharmacokinetics of SAR408701 Administered Intravenously as Monotherapy and in Combination With Other Anti-tumor Drug in Japanese Patients With Advanced Malignant Solid Tumors"), History of Changes for Study, Protocol ID: TCD15054, ClinicalTrials.gov Identifier: NCT03324113, Jan. 15, 2019, 15 pages.
Vladimirova et al., "The Role of Histological and Molecular Analysis in the Choice of Treatment for Advanced Non- Small Cell Lung Cancer," Pharmateca, Journal Archive, No. 8, 2012, 11 pages.
Wang et al., "Antibody Structure, Instability, and Formulation," Journal of Pharmaceutical Sciences, vol. 96, No. 1, Jan. 2007, pp. 1-26.
Wang, Xinxin (CN Examiner), Chinese Search Report for Chinese Application No. 202180030342.6 dated Aug. 29, 2024, 3 pages (English translation only provided).
Zhang et al., Clinical Glycobiology, Nov. 30, 2017, Science and Technology Literature Publishing House, 3 pages [See Cuilian Peng (Cn Examiner), Supplementary Search Report issued Feb. 17, 2025 for Chinese Patent Application No. 202180029921.9 for explanation of relevance].
Bristol, Lynn Anne (US Examiner), US Final Office Action for U.S. Appl. No. 17/705,016 dated Jan. 13, 2025, 26 pages.
Bristol, Lynn Anne (US Examiner), US Non-Final Office Action for U.S. Appl. No. 14/716,377 dated Jun. 28, 2016, 32 pages.
Bristol, Lynn Anne (US Examiner), US Non-Final Office Action for U.S. Appl. No. 15/446,465 dated Dec. 20, 2018, 38 pages.
Bristol, Lynn Anne (US Examiner), US Non-Final Office Action for U.S. Appl. No. 16/558,939 dated Aug. 16, 2021, 144 pages.
Bristol, Lynn Anne (US Examiner), US Non-Final Office Action for U.S. Appl. No. 17/705,016 dated May 1, 2025, 20 pages.
Bristol, Lynn Anne (US Examiner), US Non-Final Office Action for U.S. Appl. No. 17/705,016 dated Aug. 26, 2024, 32 pages.
Bristol, Lynn Anne (US Examiner), US Notice of Allowance and Fee(s) Due for U.S. Appl. No. 14/716,377 dated Nov. 30, 2016, 17 pages.
Bristol, Lynn Anne (US Examiner), US Notice of Allowance and Fee(s) Due for U.S. Appl. No. 15/446,465 dated Jun. 5, 2019, 22 pages.
Bristol, Lynn Anne (US Examiner), US Notice of Allowance and Fee(s) Due for U.S. Appl. No. 16/558,939 dated Jan. 7, 2022, 230 pages.

(56) References Cited

OTHER PUBLICATIONS

Swartwout, Brianna Kendall (US Examiner), US Non-Final Office Action for U.S. Appl. No. 17/425,603 dated Mar. 20, 2025, 167 pages.

Center for Drug Evaluation and Research (CDER) et al., "Guidance for Industry, Estimating the Maximum Safe Starting Dose in Initial Clinical Trials for Therapeutics in Adult Healthy Volunteers," Food and Drug Administration (FDA), Office of New Drugs in the CDER, Jul. 2005, pp. 1-27 (30 pages total), (Sep. 9, 2025).

Dotan et al., "Phase I/II Trial of Labetuzumab Govitecan (Anti-CEACAM5/SN-38 Antibody-Drug Conjugate) in Patients With Refractory or Relapsing Metastatic Colorectal Cancer," Journal of Clinical Oncology, vol. 35, No. 29, Oct. 10, 2017 (Published at jco.org on Aug. 17, 2017), pp. 3338-3346 (17 pages total), (Sep. 9, 2025).

Tabernero et al., "Administration of Cetuximab Every 2 Weeks in the Treatment of Metastatic Colorectal Cancer: An Effective, More Convenient Alternative to Weekly Administration?", The Oncologist, vol. 13, 2008, pp. 113-119, (Sep. 9, 2025).

Vassileva et al., "Administration of Cetuximab Every 2 Weeks in the Treatment of Metastic Colorectal Cancer: An Effective, More Covenient Alternative to Weekly Administration?", The Oncologist, vol. 13, 2008, pp. 113-119, Sep. 9, 2025).

Skoko III, John Joseph (US Examiner), US Non-Final Office Action for U.S. Appl. No. 17/917,064 dated Aug. 5, 2025, 95 pages, (Sep. 9, 2025) .

Jeon et al., "Adjuvant Chemotherapy Using the FOLFOX Regimen in Colon Cancer," Journal of the Korean Society of Coloproctology, vol. 27, No. 3, 2011, pp. 140-146.

Sanofi, "Evaluation of SAR408701 in Japanese Patients With Advanced Malignant Solid Tumors," (Official Title: "A Phase I/Ib Study to Evaluate Safety and Pharmacokinetics of SAR408701 Administered Intravenously as Monotherapy and in Combination With Other Anti-tumor Drug in Japanese Patients With Advanced Malignant Solid Tumors"), History of Changes for Study, Protocol ID: TCD15054, ClinicalTrials. gov Identifier: NCT03324113, Version 10, Mar. 25, 2019, 18 pages (Mar. 9, 2025).

Skoko III, John Joseph (US Examiner), US Non-Final Office Action for U.S. Appl. No. 17/917,375 dated Aug. 26, 2025, 78 pages, (Sep. 9, 2025).

* cited by examiner huMAb2-3-SPDB-DM4

CEACAM5 ANTIBODY-DRUG CONJUGATE FORMULATION

RELATED APPLICATION

This application claims the benefit of European Patent Application No. 20315449.7, filed Nov. 10, 2020, the entire content of which is incorporated herein by reference.

SEQUENCE LISTING

The instant application contains a Sequence Listing which has been submitted electronically in ASCII format and is hereby incorporated by reference in its entirety. Said ASCII copy, created on Nov. 8, 2021, is named 722960_SA9-297_ST25.txt and is 8,901 bytes in size.

FIELD

The present disclosure relates to the field of therapeutic treatment of cancers, such as non-squamous non-small cell lung cancer, which express CEACAM5. Certain aspects of the invention relate to the formulation and use of CEACAM5 antagonists, such as anti-CEACAM5 immunoconjugates, to treat cancer.

BACKGROUND

Carcinoembryonic antigen (CEA) is a glycoprotein involved in cell adhesion. CEA was first identified in 1965 (Gold and Freedman, *J Exp Med,* 121, 439, 1965) as a protein normally expressed by fetal gut during the first six months of gestation, and found in cancers of the pancreas, liver and colon. CEA is part of a family that belongs to the immunoglobulin superfamily. The CEA family, which consists of 18 genes, is sub-divided into two subgroups of proteins: the carcinoembryonic antigen-related cell adhesion molecule (CEACAM) subgroup and the pregnancy-specific glycoprotein subgroup (Kammerer & Zimmermann, *BMC Biology* 2010, 8:12).

Numerous studies have shown that CEACAM5, one of the CEACAM subgroup and identical to the originally identified CEA, is highly expressed on the surface of colorectal, gastric, lung, breast, prostate, ovary, cervix, and bladder tumor cells and weakly expressed in few normal epithelial tissues such as columnar epithelial and goblet cells in colon, mucous neck cells in the stomach, and squamous epithelial cells in esophagus and cervix (Hammarstrom et al., 2002, in "Tumor Markers, Physiology, Pathobiology, Technology and Clinical Applications" Eds. Diamandis E. P. et al., AACC Press, Washington pp 375 ff). Thus, CEACAM5 constitutes a therapeutic target suitable for tumor-specific targeting approaches, such as immunoconjugates.

huMAb2-3-SPDB-DM4 is an immunoconjugate (antibody-drug conjugate, ADC) comprising a humanized anti-CEACAM5 antibody linked to maytansinoid derivative 4 (DM4), a potent antimitotic agent that inhibits microtubule assembly. DM4 is covalently bound to the antibody through an optimized linker SPDB [N-succinimidyl-4-(2-pyridyldithio)butanoic acid] that is stable in plasma and cleavable inside cells. After binding and internalization in targeted cancer cells, huMAb2-3-SPDB-DM4 is degraded, releasing cytotoxic DM4 metabolites.

Currently huMAb2-3-SPDB-DM4 is in a number of clinical trials and is expected to be useful in the treatment of any of various types of CEACAM5-expressing cancers. For example, a recent clinical study has shown that huMAb2-3-SPDB-DM4 is effective in treating non-squamous, non-small cell lung cancer (NSQ NSCLC), a subtype that represents approximately 60% of lung cancers (see WO 2020/161214). However, ADCs such as huMAb2-3-SPDB-DM4 are difficult to formulate for long-term stability and shelf life. Thus, new formulations of huMAb2-3-SPDB-DM4 are of considerable interest.

SUMMARY

This disclosure provides, inter alia, improved formulations of huMAb2-3-SPDB-DM4, an antibody-drug conjugate (ADC) comprised of a monoclonal antibody that binds specifically to human carcinoembryonic antigen-related cell adhesion molecule 5 (hCEACAM5), linked to N2'-deacetyl-N-2'(4-methyl-4-mercapto-1-oxopentyl)-maytansine (DM4). The formulations disclosed herein differ from, and are optimized relative to, formulations of huMAb2-3-SPDB-DM4 used in clinical trials to date.

An aspect of the instant disclosure is a pharmaceutical formulation comprising i) anti-human carcinoembryonic antigen-related cell adhesion molecule 5 (hCEACAM5) antibody-drug conjugate (ADC),
ii) a buffering agent,
iii) a tonicity agent, and
iv) a surfactant,
at pH about 5.0 to about 6.5, wherein the ADC consists of huMAb2-3-SPDB-DM4.

In certain embodiments, the pharmaceutical formulation is a lyophilized formulation.

In certain embodiments, the pharmaceutical formulation is a liquid formulation.

An aspect of the instant disclosure is a pharmaceutical formulation comprising i) anti-human carcinoembryonic antigen-related cell adhesion molecule 5 (hCEACAM5) antibody-drug conjugate (ADC),
ii) a buffering agent,
iii) a tonicity agent,
iv) a surfactant, and
v) a chelating agent,
at pH about 5.0 to about 6.5, wherein the ADC consists of huMAb2-3-SPDB-DM4.

In certain embodiments, the pharmaceutical formulation is a lyophilized formulation.

In certain embodiments, the pharmaceutical formulation is a liquid formulation.

In certain embodiments, the buffering agent is selected from the group consisting of acetate, arginine, histidine, citrate, and any combination thereof. In some embodiments, the buffering agent is acetate, for example a sodium acetate.

In certain embodiments, the tonicity agent is a polyol. In certain embodiments, the polyol is selected from the group consisting of erythritol, glycerol, lactitol, maltitol, mannitol, sorbitol, sucrose, threitol, xylitol, and any combination thereof. In certain embodiments, the tonicity agent is sorbitol.

In certain embodiments, the surfactant is selected from the group consisting of polysorbate 20, polysorbate 80, poloxamer 188, and any combination thereof.

In certain embodiments, the surfactant is polysorbate 80.

In certain embodiments, the chelating agent is selected from the group consisting of diethylenetriaminepentaacetic acid (DTPA), ethylene glycol-bis(β-aminoethyl ether)-N,N,N',N'-tetraacetic acid (EGTA), ethylenediaminetetraacetic acid (EDTA), hydroxyethylenediamine triacetic acid (HEDTA), nitrilotriacetic acid, and any combination thereof. In certain embodiments, the chelating agent is EDTA.

In certain embodiments, the pharmaceutical formulation comprises i) anti-human carcinoembryonic antigen-related cell adhesion molecule 5 (hCEACAM5) antibody-drug conjugate (ADC),
ii) a buffering agent, for example selected from the group consisting of acetate, arginine, histidine, citrate, and any combination thereof, or for example being acetate,
iii) a polyol, for example a sorbitol,
iv) a polysorbate, for example polysorbate 80, and
v) optionally a chelating agent,
at pH about 5.0 to about 6.5, wherein the ADC consists of huMAb2-3-SPDB-DM4.

In certain embodiments, the pharmaceutical formulation comprises i) anti-human carcinoembryonic antigen-related cell adhesion molecule 5 (hCEACAM5) antibody-drug conjugate (ADC),
ii) a buffering agent, for example selected from the group consisting of acetate, arginine, histidine, citrate, and any combination thereof, or for example being acetate,
iii) a sorbitol,
iv) a polysorbate, and
v) optionally a chelating agent,
at pH about 5.0 to about 6.5, wherein the ADC consists of huMAb2-3-SPDB-DM4.

In certain embodiments, the pharmaceutical formulation comprises i) anti-human carcinoembryonic antigen-related cell adhesion molecule 5 (hCEACAM5) antibody-drug conjugate (ADC),
ii) a buffering agent, for example selected from the group consisting of acetate, arginine, histidine, citrate, and any combination thereof, or for example being acetate,
iii) a polyol,
iv) polysorbate 80, and
v) optionally a chelating agent,
at pH about 5.0 to about 6.5, wherein the ADC consists of huMAb2-3-SPDB-DM4.

In certain embodiments, the pharmaceutical formulation comprises i) anti-human carcinoembryonic antigen-related cell adhesion molecule 5 (hCEACAM5) antibody-drug conjugate (ADC),
ii) a buffering agent, for example selected from the group consisting of acetate, arginine, histidine, citrate, and any combination thereof, or for example being acetate,
iii) sorbitol,
iv) polysorbate 80, and
v) optionally a chelating agent,
at pH about 5.0 to about 6.5, wherein the ADC consists of huMAb2-3-SPDB-DM4.

In certain embodiments, the pharmaceutical formulation comprises i) anti-human carcinoembryonic antigen-related cell adhesion molecule 5 (hCEACAM5) antibody-drug conjugate (ADC),
ii) sodium acetate,
iii) sorbitol,
iv) polysorbate 80, and
v) optionally a chelating agent,
at pH about 5.0 to about 6.5, wherein the ADC consists of huMAb2-3-SPDB-DM4.

In certain embodiments, the pharmaceutical formulation comprises i) anti-human carcinoembryonic antigen-related cell adhesion molecule 5 (hCEACAM5) antibody-drug conjugate (ADC),
ii) a buffering agent,
iii) a tonicity agent,
iv) a polysorbate, for example polysorbate 80, and
v) a chelating agent,
at pH about 5.0 to about 6.5, wherein the ADC consists of huMAb2-3-SPDB-DM4.

In certain embodiments, the pharmaceutical formulation comprises i) anti-human carcinoembryonic antigen-related cell adhesion molecule 5 (hCEACAM5) antibody-drug conjugate (ADC),
ii) a buffering agent selected from acetate, arginine, histidine, citrate, and any combination thereof,
iii) a tonicity agent,
iv) polysorbate 80, and
v) ethylenediaminetetraacetic acid (EDTA),
at pH about 5.0 to about 6.5, wherein the ADC consists of huMAb2-3-SPDB-DM4.

In certain embodiments, the pharmaceutical formulation comprises i) anti-human carcinoembryonic antigen-related cell adhesion molecule 5 (hCEACAM5) antibody-drug conjugate (ADC),
ii) a buffering agent selected from acetate, histidine, citrate, and any combination thereof,
iii) a tonicity agent selected from erythritol, glycerol, lactitol, maltitol, mannitol, sorbitol, sucrose, threitol, xylitol, and any combination thereof,
iv) polysorbate 80, and
v) EDTA,
at pH about 5.0 to about 6.5, wherein the ADC consists of huMAb2-3-SPDB-DM4.

In certain embodiments, the pharmaceutical formulation comprises i) anti-human carcinoembryonic antigen-related cell adhesion molecule 5 (hCEACAM5) antibody-drug conjugate (ADC),
ii) a buffering agent selected from acetate, histidine, citrate, and any combination thereof,
iii) sorbitol,
iv) polysorbate 80, and
v) EDTA,
at pH about 5.0 to about 6.5, wherein the ADC consists of huMAb2-3-SPDB-DM4.

In certain embodiments, the pharmaceutical formulation comprises i) anti-human carcinoembryonic antigen-related cell adhesion molecule 5 (hCEACAM5) antibody-drug conjugate (ADC),
ii) sodium acetate,
iii) sorbitol,
iv) polysorbate 80, and
v) EDTA,
at pH about 5.0 to about 6.5, wherein the ADC consists of huMAb2-3-SPDB-DM4.

In certain embodiments, the pharmaceutical formulation comprises i) anti-human carcinoembryonic antigen-related cell adhesion molecule 5 (hCEACAM5) antibody-drug conjugate (ADC), ii) a buffering agent selected from acetate, histidine, citrate, and any combination thereof, at a concentration of about 5 mM to about 100 mM,
iii) a polyol,
iv) a surfactant selected from the group consisting of polysorbate 80, polysorbate 20, poloxamer 188, and any combination thereof, and
v) EDTA,
at pH about 4.0 to about 6.5,
wherein the ADC consists of huMAb2-3-SPDB-DM4.

In certain embodiments, the pharmaceutical formulation comprises
i) anti-human carcinoembryonic antigen-related cell adhesion molecule 5 (hCEACAM5) antibody-drug conjugate (ADC),
ii) a buffering agent selected from acetate, histidine, citrate, and any combination thereof, at a concentration of about 5 mM to about 100 mM,
iii) a polyol,
iv) a surfactant selected from the group consisting of polysorbate 80, polysorbate 20, poloxamer 188, and any combination thereof, and
v) EDTA,
at pH about 4.5 to about 6.5,
wherein the ADC consists of huMAb2-3-SPDB-DM4.

In certain embodiments, the pharmaceutical formulation comprises
i) anti-human carcinoembryonic antigen-related cell adhesion molecule 5 (hCEACAM5) antibody-drug conjugate (ADC),
ii) a buffering agent selected from acetate, histidine, citrate, and any combination thereof, at a concentration of about 5 mM to about 100 mM,
iii) a polyol,
iv) a surfactant selected from the group consisting of polysorbate 80, polysorbate 20, poloxamer 188, and any combination thereof, and
v) EDTA,
at pH about 5.0 to about 6.5,
wherein the ADC consists of huMAb2-3-SPDB-DM4.

In certain embodiments, the pharmaceutical formulation comprises
i) anti-human carcinoembryonic antigen-related cell adhesion molecule 5 (hCEACAM5) antibody-drug conjugate (ADC),
ii) a buffering agent selected from acetate, histidine, citrate, and any combination thereof, at a concentration of about 5 mM to about 100 mM,
iii) a tonicity agent selected from erythritol, glycerol, lactitol, maltitol, mannitol, sorbitol, sucrose, threitol, xylitol, and any combination thereof,
iv) polysorbate 80, and
v) EDTA,
at pH about 5.0 to about 6.5,
wherein the ADC consists of huMAb2-3-SPDB-DM4.

In certain embodiments, the pharmaceutical formulation comprises
i) anti-human carcinoembryonic antigen-related cell adhesion molecule 5 (hCEACAM5) antibody-drug conjugate (ADC),
ii) a buffering agent selected from acetate, histidine, citrate, and any combination thereof,
iii) a tonicity agent selected from erythritol, glycerol, lactitol, maltitol, mannitol, sorbitol, sucrose, threitol, xylitol, and any combination thereof, at a concentration of about 1% (w/v) to about 50% (w/v),
iv) polysorbate 80, and
v) EDTA,
at pH about 5.0 to about 6.5,
wherein the ADC consists of huMAb2-3-SPDB-DM4.

In certain embodiments, the pharmaceutical formulation comprises
i) anti-human carcinoembryonic antigen-related cell adhesion molecule 5 (hCEACAM5) antibody-drug conjugate (ADC),
ii) a buffering agent selected from acetate, histidine, citrate, and any combination thereof, at a concentration of about 5 mM to about 100 mM,
iii) a tonicity agent selected from erythritol, glycerol, lactitol, maltitol, mannitol, sorbitol, sucrose, threitol, xylitol, and any combination thereof, at a concentration of about 1% (w/v) to about 50% (w/v),
iv) polysorbate 80, and
v) EDTA,
at pH about 5.0 to about 6.5,
wherein the ADC consists of huMAb2-3-SPDB-DM4.

An aspect of the instant disclosure is a pharmaceutical formulation comprising
i) anti-human carcinoembryonic antigen-related cell adhesion molecule 5 (hCEACAM5) antibody-drug conjugate (ADC),
ii) sodium acetate,
iii) sorbitol,
iv) polysorbate 80, and
v) disodium EDTA,
at pH 5.5,
wherein the ADC consists of huMAb2-3-SPDB-DM4.

In certain embodiments, the pharmaceutical formulation comprises
i) 5 mg/mL anti-human carcinoembryonic antigen-related cell adhesion molecule 5 (hCEACAM5) antibody-drug conjugate (ADC),
ii) sodium acetate 10 mM,
iii) sorbitol 5% (w/v),
iv) 0.04% (w/v) polysorbate 80, and
v) 1-50 μM disodium EDTA,
at pH 5.5,
wherein the ADC consists of huMAb2-3-SPDB-DM4.

In certain embodiments, the pharmaceutical formulation comprises
i) 5 mg/mL anti-human carcinoembryonic antigen-related cell adhesion molecule 5 (hCEACAM5) antibody-drug conjugate (ADC),
ii) sodium acetate 10 mM,
iii) sorbitol 5% (w/v),
iv) 0.04% (w/v) polysorbate 80, and
v) 1 μM disodium EDTA,
at pH 5.5,
wherein the ADC consists of huMAb2-3-SPDB-DM4.

In certain embodiments, the pharmaceutical formulation comprises
i) 5 mg/mL anti-human carcinoembryonic antigen-related cell adhesion molecule 5 (hCEACAM5) antibody-drug conjugate (ADC),
ii) sodium acetate 10 mM,
iii) sorbitol 5% (w/v),
iv) 0.04% (w/v) polysorbate 80, and
v) 10 μM disodium EDTA,
at pH 5.5,
wherein the ADC consists of huMAb2-3-SPDB-DM4.

In certain embodiments, the pharmaceutical formulation comprises i) 5 mg/mL anti-human carcinoembryonic antigen-related cell adhesion molecule 5 (hCEACAM5) antibody-drug conjugate (ADC),
ii) sodium acetate 10 mM,
iii) sorbitol 5% (w/v),
iv) 0.04% (w/v) polysorbate 80, and
v) 50 μM disodium EDTA,
at pH 5.5, wherein the ADC consists of huMAb2-3-SPDB-DM4.

An aspect of the instant disclosure is a method of treating a cancer, the method comprising administering to a subject in need thereof an effective amount of any one of the foregoing pharmaceutical formulations.

In certain embodiments, the pharmaceutical formulation comprises i) 5 mg/mL anti-human carcinoembryonic antigen-related cell adhesion molecule 5 (hCEACAM5) antibody-drug conjugate (ADC),
ii) sodium acetate 10 mM,
iii) sorbitol 5% (w/v),
iv) 0.04% (w/v) polysorbate 80, and
v) 10 μM disodium EDTA,
at pH 5.5, wherein the ADC consists of huMAb2-3-SPDB-DM4.

In certain embodiments, the cancer is a high carcinoembryonic antigen-related cell adhesion molecule cancer.

In certain embodiments, the cancer is selected from the group consisting of colorectal, gastric, lung, breast, prostate, ovarian, cervical, and bladder cancer.

In certain embodiments, the cancer is selected from the group consisting of lung, breast, prostate, ovarian, cervical, and bladder cancer.

In certain embodiments, the cancer is lung cancer.

In certain embodiments, the lung cancer is non-squamous non-small cell lung carcinoma.

In certain embodiments, the subject is a human.

DETAILED DESCRIPTION

Figure 1:
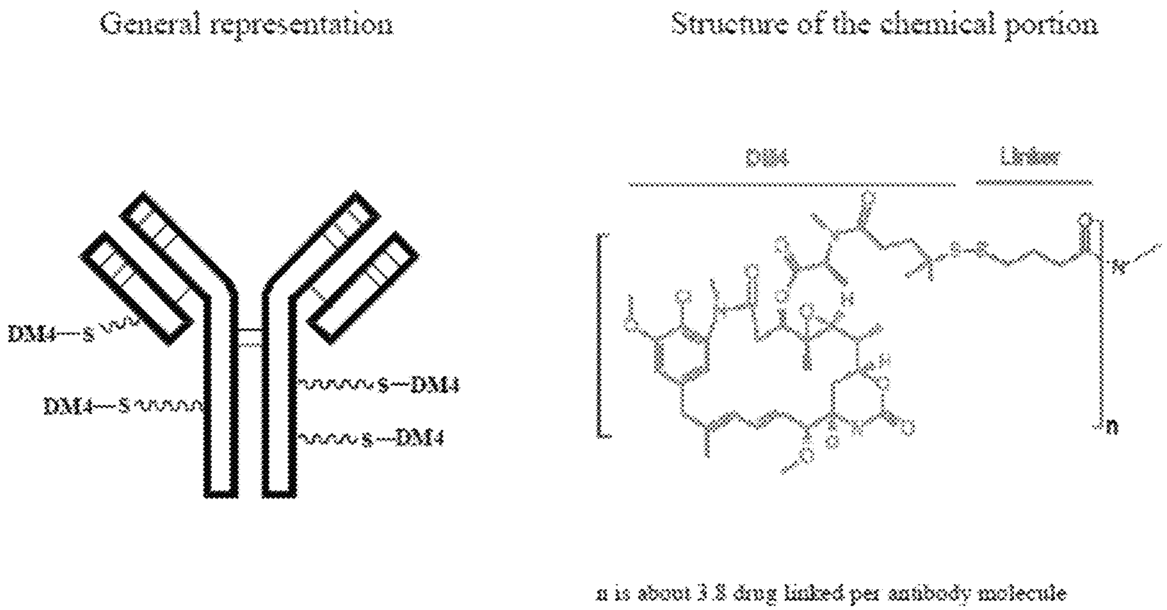
FIG. 1 is a general representation of huMAb2-3-SPDB-DM4 (left) and structure of the chemical portion (right).

The present invention discloses a pharmaceutical formulation of an antibody-drug conjugate (ADC) which specifically binds human and *Macaca fascicularis* CEACAM5 proteins. This ADC, known as huMAb2-3-SPDB-DM4, and its formulation disclosed herein, are useful in the treatment of any of various types of CEACAM5-expressing cancers, including non-squamous non-small cell lung cancer. Unexpectedly, it has been found in accordance with the instant disclosure that inclusion of modest amounts of ethylenediaminetetraacetic acid (EDTA) in formulation of huMAb2-3-SPDB-DM4 significantly increased stability of the ADC and its formulation.

Carcinoembryonic antigen (CEA) is a glycoprotein involved in cell adhesion. CEA was first identified in 1965 (Gold and Freedman, *J Exp Med,* 121, 439, 1965) as a protein normally expressed by fetal gut during the first six months of gestation, and found in cancers of the pancreas, liver and colon. CEA is part of a family that belongs to the immunoglobulin superfamily. The CEA family, which consists of 18 genes, is subdivided into two subgroups of proteins: the carcinoembryonic antigen-related cell adhesion molecule (CEACAM) subgroup and the pregnancy-specific glycoprotein subgroup (Kammerer & Zimmermann, *BMC Biology* 2010, 8:12).

In humans, the CEACAM subgroup consists of 7 members: CEACAM1, CEACAM3, CEACAM4, CEACAM5, CEACAM6, CEACAM7, and CEACAM5. Numerous studies have shown that CEACAM5, identical to the originally identified CEA, is highly expressed on the surface of colorectal, gastric, lung, breast, prostate, ovary, cervix, and bladder tumor cells and only weakly expressed in few normal epithelial tissues such as columnar epithelial and goblet cells in colon, mucous neck cells in the stomach, and squamous epithelial cells in esophagus and cervix (Hammarstrom et al, 2002, in "Tumor Markers, Physiology, Pathobiology, Technology and Clinical Applications" Eds. Diamandis E. P. et al., AACC Press, Washington pp 375). Thus, CEACAM5 constitutes a therapeutic target suitable for tumor-specific targeting approaches, such as immunoconjugates.

As used herein "CEACAM5" designates the "carcinoembryonic antigen-related cell adhesion molecule 5", also known as CD66e (Cluster of Differentiation 66e) or CEA. CEACAM5 is a glycoprotein involved in cell adhesion. CEACAM5 is highly expressed in particular on the surface of colorectal, gastric, lung and uterine tumor cells.

As used herein, "high CEACAM5 cancer" refers to any of several types of cancer including colorectal, gastric, lung, breast, prostate, ovary, cervical, and bladder cancer. In certain embodiments, "high CEACAM5 cancer" refers to any of several types of cancer including colon, lung, stomach, cervical and pancreatic cancer.

In some embodiments, the lung cancer is non-squamous non-small cell lung cancer. In certain embodiments, high CEACAM5 expressers have greater than or equal to 2+ intensity in at least 50% of expressing tumor cell population. In certain embodiments, high CEACAM5 expressers have greater than 2+ intensity in at least 50% of expressing tumor cell population. High CEACAM5 expressers represent ~20% of lung cancers.

Immunoconjugate

The ADC huMAb2-3-SPDB-DM4 is an immunoconjugate combining huMAb2-3 (anti-CEACAM5) antibody and the maytansinoid derivative 4 (DM4), a potent antimitotic agent that inhibits microtubule assembly. DM4 is covalently bound to huMAb2-3 through an optimized linker SPDB [N-succinimidyl 4-(2-pyridyldithio)-butyrate] that is stable in plasma and cleavable inside cells. After binding and internalization in targeted cancer cells, huMAb2-3-SPDB-DM4 is degraded, releasing cytotoxic DM4 metabolites.

The antibody portion of huMAb2-3-SPDB-DM4 is a human IgG1 kappa antibody having a pair of heavy chains (HC) each comprising a variable heavy (VH) domain, and a pair of light chains (LC) each comprising a variable light (VL) domain. Each VH domain comprises three complementarity-determining regions (CDRs), HCDR1, HCDR2, and HCDR3. Each VL domain comprises three complementarity-determining regions (CDRs), LCDR1, LCDR2, and LCDR3. The amino acid sequences for these polypeptides are as follows:

HCDR1
SEQ ID NO: 1
GFVFSSYD

HCDR2
SEQ ID NO: 2
ISSGGGIT

HCDR3
SEQ ID NO: 3
AAHYFGSSGPFAY

LCDR1
SEQ ID NO: 4
ENIFSY

LCDR2
NTR

LCDR3
SEQ ID NO: 5
QHHYGTPFT

-continued

VH

SEQ ID NO: 6

EVQLQESGPGLVKPGGSLSLSCAASGFVFSSYDMSWVRQTPERGLEWVAY

ISSGGGITYAPSTVKGRFTVSRDNAKNTLYLQMNSLTSEDTAVYYCAAHY

FGSSGPFAYWGQGTLVTVSS

VL

SEQ ID NO: 7

DIQMTQSPASLSASVGDRVTITCRASENIFSYLAWYQQKPGKSPKLLVYN

TRTLAEGVPSRFSGSGSGTDFSLTISSLQPEDFATYYCQHHYGTPFTFGS

GTKLEIK

HC

SEQ ID NO: 8

EVQLQESGPGLVKPGGSLSLSCAASGFVFSSYDMSWVRQTPERGLEWVAY

ISSGGGITYAPSTVKGRFTVSRDNAKNTLYLQMNSLTSEDTAVYYCAAHY

FGSSGPFAYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

LC

SEQ ID NO: 9

DIQMTQSPASLSASVGDRVTITCRASENIFSYLAWYQQKPGKSPKLLVYN

TRTLAEGVPSRFSGSGSGTDFSLTISSLQPEDFATYYCQHHYGTPFTFGS

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

As used herein "maytansinoids" denotes maytansinoids and maytansinoid analogs. Maytansinoids are drugs that inhibit microtubule formation and that are highly toxic to mammalian cells.

Examples of suitable maytansinoids include maytansinol and maytansinol analogs.

The cytotoxic conjugates of the present invention utilize the thiol-containing maytansinoid DM4, formally termed $N^{2'}$-deacetyl-N-$^{2'}$(4-methyl-4-mercapto-1-oxopentyl)-maytansine, as the cytotoxic agent. DM4 is represented by the following structural formula (I):

(I)

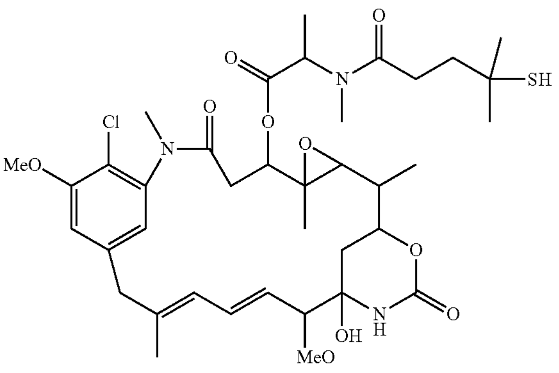

In some embodiments, the antibodies of the present invention are covalently attached, directly or via a cleavable or non-cleavable linker, to at least one growth inhibitory agent.

"Linker", as used herein, means a chemical moiety comprising a covalent bond or a chain of atoms that covalently attaches a polypeptide to a drug moiety.

The conjugates may be prepared by in vitro methods. In order to link a drug or prodrug to the antibody, a linking group is used. Suitable linking groups are well known in the art and include disulfide groups, thioether groups, acid labile groups, photolabile groups, peptidase labile groups and esterase labile groups. Conjugation of an antibody of the invention with cytotoxic agents or growth inhibitory agents may be made using a variety of bifunctional protein coupling agents including but not limited to N-succinimidyl-4-(2-pyridyldithio)butanoic acid (SPDB), butanoic acid 4-[(5-nitro-2-pyridinyl)dithio]-2,5-dioxo-1-pyrrolidinyl ester (nitro-SPDB), 4-(Pyridin-2-yldisulfanyl)-2-sulfo-butyric acid (sulfo-SPDB), N-succinimidyl (2-pyridyldithio) propionate (SPDP), succinimidyl (N-maleimidomethyl) cyclohexane-1-carboxylate (SMCC), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl)-hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

The linker may be a "cleavable linker" facilitating release of the cytotoxic agent or growth inhibitory agent in the cell. For example, an acid-labile linker, a peptidase-sensitive linker, an esterase-labile linker, a photolabile linker or a disulfide-containing linker (See e.g., U.S. Pat. No. 5,208,020) may be used. The linker may be also a "non-cleavable linker" (for example SMCC linker) that might lead to better tolerance in some cases.

According to an embodiment, in the conjugate of the invention, the growth inhibitory agent is the maytansinoid DM4.

In said conjugate, the antibody is conjugated to said at least one growth inhibitory agent by a linking group. In an embodiment said linking group is a cleavable or a non-cleavable linker, such as N-succinimidyl-4-(2-pyridyldithio) butanoic acid (SPDB), 4-(Pyridin-2-yldisulfanyl)-2-sulfo-butyric acid (sulfo-SPDB), or succinimidyl (N-maleimidomethyl) cyclohexane-1-carboxylate (SMCC).

In an embodiment, the linking group is SPDB, and the conjugate consists of an antibody-SPDB-DM4 conjugate of formula (II)

(II)

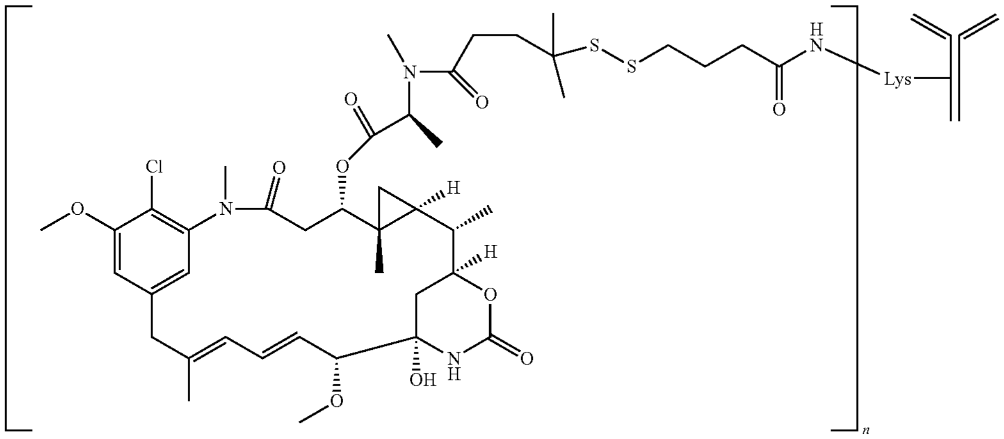

;

Ab-SPDB-DM4 where n is an integer greater than or equal to 1. An average value of n is typically about 3.8. See also FIG. 1.

In general, the conjugate can be obtained by a process comprising the steps of:

(i) bringing into contact an optionally-buffered aqueous solution of a cell-binding agent (e.g., an antibody according to the invention) with solutions of a linker and a cytotoxic compound;

(ii) then optionally separating the conjugate which was formed in (i) from the unreacted cell-binding agent.

The aqueous solution of cell-binding agent can be buffered with buffers such as, e.g., potassium phosphate, acetate, citrate or N-2-Hydroxyethylpiperazine-N'-2-ethanesulfonic acid (HEPES buffer). The buffer depends upon the nature of the cell-binding agent. The cytotoxic compound is in solution in an organic polar solvent, e.g., dimethyl sulfoxide (DMSO) or dimethylacetamide (DMA).

The reaction temperature is usually comprised between 20 and 40° C. The reaction time can vary from 1 to 24 hours. The reaction between the cell-binding agent and the cytotoxic agent can be monitored by size exclusion chromatography (SEC) with a refractometric and/or UV detector. If the conjugate yield is too low, the reaction time can be extended.

A number of different chromatography methods can be used by the person skilled in the art in order to perform the separation of step (ii): the conjugate can be purified e.g., by SEC, adsorption chromatography (such as ion exchange chromatography, IEC), hydrophobic interaction chromatography (HIC), affinity chromatography, mixed-support chromatography such as hydroxyapatite chromatography, or high-performance liquid chromatography (HPLC). Purification by dialysis or diafiltration can also be used.

According to an embodiment, the conjugate according to the invention is characterised by a "drug-to-antibody ratio" (or "DAR") ranging from 1 to 10, for instance from 2 to 5, in particular from 3 to 4. This is generally the case of conjugates including maytansinoid molecules.

This DAR number can vary with the nature of the antibody and of the drug (i.e., the growth-inhibitory agent) used along with the experimental conditions used for the conjugation (like the ratio growth-inhibitory agent/antibody, the reaction time, the nature of the solvent and of the cosolvent if any). Thus, the contact between the antibody and the growth-inhibitory agent leads to a mixture comprising several conjugates differing from one another by different drug-to-antibody ratios; optionally the naked antibody; optionally aggregates. The DAR that is determined is thus a mean value.

A method which can be used to determine the DAR consists in measuring spectrophotometrically the ratio of the absorbance at of a solution of substantially purified conjugate at $\lambda_D$ and 280 nm. 280 nm is a wavelength generally used for measuring protein concentration, such as antibody concentration. The wavelength $\lambda_D$ is selected so as to allow discriminating the drug from the antibody, i.e., as readily known to the skilled person, $\lambda_D$ is a wavelength at which the drug has a high absorbance and $\lambda_D$ is sufficiently remote from 280 nm to avoid substantial overlap in the absorbance peaks of the drug and antibody. $\lambda_D$ may be selected as being 252 nm in the case of maytansinoid molecules. A method of DAR calculation may be derived from Antony S. Dimitrov (ed), LLC, 2009, Therapeutic Antibodies and Protocols, vol 525, 445, Springer Science.

The absorbances for the conjugate at $\lambda_D$ ($A_{\lambda D}$) and at 280 nm ($A_{280}$) are measured either on the monomeric peak of the size exclusion chromatography (SEC) analysis (allowing to calculate the "DAR(SEC)" parameter) or using a classic spectrophotometer apparatus (allowing to calculate the "DAR(UV)" parameter). The absorbances can be expressed as follows:

$$A_{\lambda D}=(c_D \times \varepsilon_{D\lambda D})+(c_A \times \varepsilon_{A\lambda D})$$

$$A_{280}=(c_D \times \varepsilon_{D280})+(c_A \times \varepsilon_{A280})$$

wherein:

$c_D$ and $c_A$ are respectively the concentrations in the solution of the drug and of the antibody;

$\varepsilon_{D\lambda D}$ and $\varepsilon_{D280}$ are respectively the molar extinction coefficients of the drug at $\lambda_D$ and 280 nm; and $\varepsilon_{A\lambda D}$ and $\varepsilon_{A280}$ are respectively the molar extinction coefficients of the antibody at $\lambda_D$ and 280 nm.

Resolution of these two equations with two unknowns leads to the following equations:

$$c_D=[(\varepsilon_{A280} \times A_{\lambda D}) \times (\varepsilon_{A\lambda D} \times A_{280})]/[(\varepsilon_{D\lambda D} \times \varepsilon_{A280})-(\varepsilon_{A\lambda D} \times \varepsilon_{D280})]$$

$$c_A=[A_{280}-(c_D \times \varepsilon_{D280})]/\varepsilon_{A280}$$

The average DAR is then calculated from the ratio of the drug concentration to that of the antibody:$DAR=c_D/c_A$.

huMAb2-3-SPDB-DM4 is currently completing a Phase 1/Phase 2 first-in-human study for the evaluation of the safety, pharmacokinetics and antitumor activity of huMAb2-3-SPDB-DM4 in patients with advanced solid tumors (NCT02187848).

huMAb2-3-SPDB-DM4 is currently undergoing a randomized, open label Phase 3 study versus docetaxel in previously treated metastatic non-squamous non-small cell lung cancer patients with CEACAM5 positive tumors (NCT04154956).

As used herein, a "subject" refers to a mammal, including mice, rats, hamsters, Guinea pigs, rabbits, cats, dogs, sheep, goats, pigs, cows, horses, non-human primates, and humans. In certain embodiments, a subject is a human.

Formulations

It has now been discovered, in accordance with the instant disclosure, that the formulation of huMAb2-3-SPDB-DM4 advantageously includes the ADC, a buffering agent, a tonicity agent, a surfactant, and optionally a chelating agent. Further, it has been discovered, in accordance with the present disclosure, that the formulation of huMAb2-3-SPDB-DM4 advantageously includes the ADC, acetate, sorbitol, and polysorbate 80 (PS80). It has now further been discovered, in accordance with the instant disclosure, that the formulation of huMAb2-3-SPDB-DM4 advantageously includes the ADC, acetate, sorbitol, polysorbate 80 (PS80), and EDTA. This formulation is suitable for both liquid and lyophilized forms.

It will be understood that the pharmaceutical compositions disclosed herein can be aqueous solutions containing each of the recited components in amounts and concentrations as specified.

In the case of lyophilizates prepared from aqueous solutions, the recited components in amounts and concentrations as specified relate to amounts and concentrations in the formulations upon reconstitution. Liquid used for reconstitution will generally be sterile water for injection, in amounts suitable to realize the recited amounts and concentrations of the specified components.

An aspect of the instant disclosure is a pharmaceutical formulation comprising i) anti-human carcinoembryonic antigen-related cell adhesion molecule 5 (hCEACAM5) antibody-drug conjugate (ADC),
ii) a buffering agent,
iii) a tonicity agent, and
iv) a surfactant,
at pH about 5.0 to about 6.5, wherein the ADC consists of huMAb2-3-SPDB-DM4.

In certain embodiments, the pharmaceutical formulation is a lyophilized formulation.

In certain embodiments, the pharmaceutical formulation is a liquid formulation.

In certain embodiments, the pharmaceutical formulation comprises i) anti-human carcinoembryonic antigen-related cell adhesion molecule 5 (hCEACAM5) antibody-drug conjugate (ADC),
ii) a buffering agent,
iii) a tonicity agent, for example a polyol,
iv) a surfactant, for example a polysorbate, and
v) optionally a chelating agent,
at pH about 5.0 to about 6.5, wherein the ADC consists of huMAb2-3-SPDB-DM4.

In certain embodiments, the pharmaceutical formulation comprises i) anti-human carcinoembryonic antigen-related cell adhesion molecule 5 (hCEACAM5) antibody-drug conjugate (ADC),
ii) a buffering agent,
iii) a polyol,
iv) a polysorbate, and
v) optionally a chelating agent,
at pH about 5.0 to about 6.5, wherein the ADC consists of huMAb2-3-SPDB-DM4.

An aspect of the instant disclosure is a pharmaceutical formulation comprising i) anti-human carcinoembryonic antigen-related cell adhesion molecule 5 (hCEACAM5) antibody-drug conjugate (ADC),
ii) a buffering agent,
iii) a tonicity agent,
iv) a surfactant, and
v) a chelating agent,
at pH about 5.0 to about 6.5, wherein the ADC consists of huMAb2-3-SPDB-DM4.

In certain embodiments, the pharmaceutical formulation is a lyophilized formulation.

In certain embodiments, the pharmaceutical formulation is a liquid formulation.

In certain embodiments, the pharmaceutical formulation comprises i) anti-human carcinoembryonic antigen-related cell adhesion molecule 5 (hCEACAM5) antibody-drug conjugate (ADC),
ii) a buffering agent, for example selected from the group consisting of acetate, arginine, histidine, citrate, and any combination thereof, or for example being acetate,
iii) a polyol, for example a sorbitol,
iv) a polysorbate, for example polysorbate 80, and
v) optionally a chelating agent,
at pH about 5.0 to about 6.5, wherein the ADC consists of huMAb2-3-SPDB-DM4.

In certain embodiments, the pharmaceutical formulation comprises i) anti-human carcinoembryonic antigen-related cell adhesion molecule 5 (hCEACAM5) antibody-drug conjugate (ADC),
ii) a buffering agent, for example selected from the group consisting of acetate, arginine, histidine, citrate, and any combination thereof, or for example being acetate,
iii) a sorbitol,
iv) a polysorbate, and
v) optionally a chelating agent,
at pH about 5.0 to about 6.5, wherein the ADC consists of huMAb2-3-SPDB-DM4.

In certain embodiments, the pharmaceutical formulation comprises i) anti-human carcinoembryonic antigen-related cell adhesion molecule 5 (hCEACAM5) antibody-drug conjugate (ADC),
ii) a buffering agent, for example selected from the group consisting of acetate, arginine, histidine, citrate, and any combination thereof, or for example being acetate,
iii) a polyol, iv) polysorbate 80, and
v) optionally a chelating agent,
at pH about 5.0 to about 6.5, wherein the ADC consists of huMAb2-3-SPDB-DM4.

In certain embodiments, the pharmaceutical formulation comprises i) anti-human carcinoembryonic antigen-related cell adhesion molecule 5 (hCEACAM5) antibody-drug conjugate (ADC),
ii) a buffering agent, for example selected from the group consisting of acetate, arginine, histidine, citrate, and any combination thereof, or for example being acetate,
iii) sorbitol,
iv) polysorbate 80, and
v) optionally a chelating agent,
at pH about 5.0 to about 6.5, wherein the ADC consists of huMAb2-3-SPDB-DM4.

In certain embodiments, the pharmaceutical formulation comprises i) anti-human carcinoembryonic antigen-related cell adhesion molecule 5 (hCEACAM5) antibody-drug conjugate (ADC),
ii) sodium acetate,
iii) sorbitol,
iv) polysorbate 80, and
v) optionally a chelating agent,
at pH about 5.0 to about 6.5, wherein the ADC consists of huMAb2-3-SPDB-DM4.

In certain embodiments, the pharmaceutical formulation comprises i) anti-human carcinoembryonic antigen-related cell adhesion molecule 5 (hCEACAM5) antibody-drug conjugate (ADC),
ii) a buffering agent,
iii) a tonicity agent,
iv) a polysorbate, and
v) a chelating agent,
at pH about 5.0 to about 6.5, wherein the ADC consists of huMAb2-3-SPDB-DM4.

In certain embodiments, the pharmaceutical formulation is a lyophilized formulation.

In certain embodiments, the pharmaceutical formulation is a liquid formulation.

In certain embodiments, the pharmaceutical formulation comprises i) anti-human carcinoembryonic antigen-related cell adhesion molecule 5 (hCEACAM5) antibody-drug conjugate (ADC),
ii) a buffering agent,
iii) a polyol,
iv) a polysorbate, and
v) a chelating agent,
at pH about 5.0 to about 6.5, wherein the ADC consists of huMAb2-3-SPDB-DM4.

Buffering agents that may be suitable for use in the formulations include, but are not limited to, organic acid salts such as salts of citric acid, ascorbic acid, gluconic acid, carbonic acid, tartaric acid, succinic acid, acetic acid or phthalic acid; Tris, tromethamine (his (hydroxymethyl)-aminomethane) hydrochloride, or phosphate buffer. In addition, amino acid components can also be used as buffering agent. Such amino acid component includes without limitation arginine, glycine, glycylglycine, and histidine. The arginine buffers include arginine acetate, arginine chloride, arginine phosphate, arginine sulfate, arginine succinate, etc. In one embodiment, the arginine buffer is arginine acetate. Examples of histidine buffers include histidine chloride-arginine chloride, histidine acetate-arginine acetate, histidine phosphate-arginine phosphate, histidine sulfate-arginine sulfate, histidine succinate-arginine succinate, etc. These are available from a number of commercial suppliers.

In some embodiments, a buffering agent may be a salt of acetic acid, arginine, histidine, citric acid, such as alkaline metal salt thereof. A salt of acetic acid may be sodium acetate.

Tonicity agents that may be suitable for use in the formulations include, but are not limited to, polyols including sugars (reducing and nonreducing sugars), sugar alcohols, and sugar acids. A "reducing sugar" is one which contains a hemiacetal group that can reduce metal ions or react covalently with lysine and other amino groups in proteins and a "nonreducing sugar" is one which does not have these properties of a reducing sugar. Examples of reducing sugars are fructose, mannose, maltose, lactose, arabinose, xylose, ribose, rhamnose, galactose and glucose. Nonreducing sugars include sucrose, trehalose, sorbose, melezitose and raffinose. Sugar alcohols are selected from mannitol, xylitol, erythritol, maltitol, lactitol erythritol, threitol, sorbitol and glycerol. Sugar acids include L-gluconate and metallic salts thereof. These are available from a number of commercial suppliers.

In some embodiments, a polyol may be sorbitol.

Surfactants that may be suitable for use in the formulations include, but are not limited to, polysorbates and poloxamers. Poloxamers include, for example, poloxamer 188. These are available from a number of commercial suppliers.

Polysorbates that may be suitable for use in the formulations include, but are not limited to, polysorbate 20, polysorbate 40, polysorbate 65, polysorbate 80, polysorbate 81, and polysorbate 85. These are available from a number of commercial suppliers.

In some embodiments, a polysorbate may be polysorbate 80.

Chelating agents that may be suitable for use in the formulations include, but are not limited to, diethylenetriaminepentaacetic acid (DTPA), ethylenediaminetetraacetic acid (EDTA), hydroxyethylenediamine triacetic acid (HEDTA), nitrilotriacetic acid, ethylene glycol-bis(β-aminoethyl ether)-N,N,N',N'-tetraacetic acid (EGTA), and salts thereof, e.g., disodium EDTA, calcium disodium EDTA, tetrasodium EDTA. These are available from a number of commercial suppliers.

In some embodiments, a chelating agent may be ethylenediaminetetraacetic acid (EDTA), or a salt thereof, e.g., disodium EDTA, calcium disodium EDTA, tetrasodium EDTA.

In certain embodiments, the pharmaceutical formulation comprises i) anti-human carcinoembryonic antigen-related cell adhesion molecule 5 (hCEACAM5) antibody-drug conjugate (ADC),
ii) a buffering agent selected from acetate, arginine, histidine, citrate, and any combination thereof,
iii) a tonicity agent,
iv) Polysorbate 80, and
v) ethylenediaminetetraacetic acid (EDTA),
at pH about 5.0 to about 6.5, wherein the ADC consists of huMAb2-3-SPDB-DM4.

In certain embodiments, the pharmaceutical formulation comprises i) anti-human carcinoembryonic antigen-related cell adhesion molecule 5 (hCEACAM5) antibody-drug conjugate (ADC), ii) a buffering agent selected from acetate, histidine, citrate, and any combination thereof,
iii) a tonicity agent selected from erythritol, glycerol, lactitol, maltitol, mannitol, sorbitol, sucrose, threitol, xylitol, and any combination thereof,
iv) Polysorbate 80, and
v) EDTA,
at pH about 5.0 to about 6.5,
wherein the ADC consists of huMAb2-3-SPDB-DM4.

In certain embodiments, the pharmaceutical formulation comprises
i) anti-human carcinoembryonic antigen-related cell adhesion molecule 5 (hCEACAM5) antibody-drug conjugate (ADC),
ii) a buffering agent selected from acetate, histidine, citrate, and any combination thereof,
iii) sorbitol,
iv) polysorbate 80, and
v) EDTA,
at pH about 5.0 to about 6.5,
wherein the ADC consists of huMAb2-3-SPDB-DM4.

In certain embodiments, the pharmaceutical formulation comprises
i) anti-human carcinoembryonic antigen-related cell adhesion molecule 5 (hCEACAM5) antibody-drug conjugate (ADC),
ii) sodium acetate,
iii) sorbitol,
iv) polysorbate 80, and
v) EDTA,
at pH about 5.0 to about 6.5,
wherein the ADC consists of huMAb2-3-SPDB-DM4.

In certain embodiments, the pharmaceutical formulation comprises
i) anti-human carcinoembryonic antigen-related cell adhesion molecule 5 (hCEACAM5) antibody-drug conjugate (ADC),
ii) a buffering agent selected from acetate, histidine, citrate, and any combination thereof, at a concentration of about 5 mM to about 100 mM,
iii) a polyol,
iv) a surfactant selected from the group consisting of polysorbate 80, polysorbate 20, poloxamer 188, and any combination thereof, and
v) EDTA,
at pH about 4.0 to about 6.5,
wherein the ADC consists of huMAb2-3-SPDB-DM4.

In certain embodiments, the pharmaceutical formulation comprises
i) anti-human carcinoembryonic antigen-related cell adhesion molecule 5 (hCEACAM5) antibody-drug conjugate (ADC),
ii) a buffering agent selected from acetate, histidine, citrate, and any combination thereof, at a concentration of about 5 mM to about 100 mM,
iii) a polyol,
iv) a surfactant selected from the group consisting of polysorbate 80, polysorbate 20, poloxamer 188, and any combination thereof, and
v) EDTA,
at pH about 4.5 to about 6.5,
wherein the ADC consists of huMAb2-3-SPDB-DM4.

In certain embodiments, the pharmaceutical formulation comprises
i) anti-human carcinoembryonic antigen-related cell adhesion molecule 5 (hCEACAM5) antibody-drug conjugate (ADC), ii) a buffering agent selected from acetate, histidine, citrate, and any combination thereof, at a concentration of about 5 mM to about 100 mM,
iii) a polyol,
iv) a surfactant selected from the group consisting of polysorbate 80, polysorbate 20, poloxamer 188, and any combination thereof, and
v) EDTA,
at pH about 5.0 to about 6.5,
wherein the ADC consists of huMAb2-3-SPDB-DM4.

In certain embodiments, the pharmaceutical formulation comprises
i) anti-human carcinoembryonic antigen-related cell adhesion molecule 5 (hCEACAM5) antibody-drug conjugate (ADC),
ii) a buffering agent selected from acetate, histidine, citrate, and any combination thereof, at a concentration of about 5 mM to about 100 mM,
iii) a tonicity agent selected from erythritol, glycerol, lactitol, maltitol, mannitol, sorbitol, sucrose, threitol, xylitol, and any combination thereof,
iv) Polysorbate 80, and
v) EDTA,
at pH about 5.0 to about 6.5,
wherein the ADC consists of huMAb2-3-SPDB-DM4.

In certain embodiments, the pharmaceutical formulation comprises
i) anti-human carcinoembryonic antigen-related cell adhesion molecule 5 (hCEACAM5) antibody-drug conjugate (ADC),
ii) a buffering agent selected from acetate, histidine, citrate, and any combination thereof,
iii) a tonicity agent selected from erythritol, glycerol, lactitol, maltitol, mannitol, sorbitol, sucrose, threitol, xylitol, and any combination thereof, at a concentration of about 1% (w/v) to about 50% (w/v),
iv) Polysorbate 80, and
v) EDTA,
at pH about 5.0 to about 6.5,
wherein the ADC consists of huMAb2-3-SPDB-DM4.

In certain embodiments, the pharmaceutical formulation comprises
i) anti-human carcinoembryonic antigen-related cell adhesion molecule 5 (hCEACAM5) antibody-drug conjugate (ADC),
ii) a buffering agent selected from acetate, histidine, citrate, and any combination thereof, at a concentration of about 5 mM to about 100 mM,
iii) a tonicity agent selected from erythritol, glycerol, lactitol, maltitol, mannitol, sorbitol, sucrose, threitol, xylitol, and any combination thereof, at a concentration of about 1% (w/v) to about 50% (w/v),
iv) Polysorbate 80, and
v) EDTA,
at pH about 5.0 to about 6.5,
wherein the ADC consists of huMAb2-3-SPDB-DM4.

In accordance with each of the foregoing aspects and embodiments, in various certain embodiments, the pH can be about 5.0 to about 6.0. In various certain embodiments, the pH can be about 5.0 to about 5.5. In various certain embodiments, the pH can be about 5.6 to about 6.5. In various certain embodiments, the pH can be about 5.6 to about 6.0. In various certain embodiments, the pH can be about 6.1 to about 6.5.

In accordance with each of the foregoing aspects and embodiments, in various certain embodiments, the pH can be 5.0 to 6.0. In various certain embodiments, the pH can be 5.0 to 5.5. In various certain embodiments, the pH can be 5.6 to 6.5. In various certain embodiments, the pH can be 5.6 to 6.0. In various certain embodiments, the pH can be 6.1 to 6.5.

In accordance with each of the foregoing aspects and embodiments, in various certain embodiments, the pH can be about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, or about 6.5.

In accordance with each of the foregoing aspects and embodiments, in various certain embodiments, the pH can be 5.0, 5.1, 5.2, 5.3, 5.4, 5.5, 5.6, 5.7, 5.8, 5.9, 6.0, 6.1, 6.2, 6.3, 6.4, or 6.5.

In accordance with each of the foregoing aspects and embodiments, the buffering agent can be selected from acetate, histidine, citrate, and any combination thereof, at a concentration of about 5 mM to about 100 mM. In various embodiments, the buffering agent is present at a concentration of about 10 mM to about 100 mM. In various embodiments, the buffering agent is present at a concentration of about 20 mM to about 100 mM. In various embodiments, the buffering agent is present at a concentration of about 30 mM to about 100 mM. In various embodiments, the buffering agent is present at a concentration of about 40 mM to about 100 mM. In various embodiments, the buffering agent is present at a concentration of about 50 mM to about 100 mM. In various embodiments, the buffering agent is present at a concentration of about 60 mM to about 100 mM. In various embodiments, the buffering agent is present at a concentration of about 70 mM to about 100 mM. In various embodiments, the buffering agent is present at a concentration of about 80 mM to about 100 mM. In various embodiments, the buffering agent is present at a concentration of about 90 mM to about 100 mM. In various embodiments, the buffering agent is present at a concentration of about 5 mM to about 90 mM. In various embodiments, the buffering agent is present at a concentration of about 5 mM to about 80 mM. In various embodiments, the buffering agent is present at a concentration of about 5 mM to about 70 mM. In various embodiments, the buffering agent is present at a concentration of about 5 mM to about 60 mM. In various embodiments, the buffering agent is present at a concentration of about 5 mM to about 50 mM. In various embodiments, the buffering agent is present at a concentration of about 5 mM to about 40 mM. In various embodiments, the buffering agent is present at a concentration of about 5 mM to about 30 mM. In various embodiments, the buffering agent is present at a concentration of about 5 mM to about 20 mM. In various embodiments, the buffering agent is present at a concentration of about 5 mM to about 10 mM.

In accordance with each of the foregoing aspects and embodiments, the buffering agent can be selected from acetate, histidine, citrate, and any combination thereof, at a concentration of 5 mM to 100 mM. In various embodiments, the buffering agent is present at a concentration of 10 mM to 100 mM. In various embodiments, the buffering agent is present at a concentration of 20 mM to 100 mM. In various embodiments, the buffering agent is present at a concentration of 30 mM to 100 mM. In various embodiments, the buffering agent is present at a concentration of 40 mM to 100 mM. In various embodiments, the buffering agent is present at a concentration of 50 mM to 100 mM. In various embodiments, the buffering agent is present at a concentration of 60 mM to 100 mM. In various embodiments, the buffering agent is present at a concentration of 70 mM to 100 mM. In various embodiments, the buffering agent is present at a concentration of 80 mM to 100 mM. In various embodiments, the buffering agent is present at a concentration of 90 mM to 100 mM. In various embodiments, the buffering agent is present at a concentration of 5 mM to 90 mM. In various embodiments, the buffering agent is present at a concentration of 5 mM to 80 mM. In various embodiments, the buffering agent is present at a concentration of 5 mM to 70 mM. In various embodiments, the buffering agent is present at a concentration of 5 mM to 60 mM. In various embodiments, the buffering agent is present at a concentration of 5 mM to 50 mM. In various embodiments, the buffering agent is present at a concentration of 5 mM to 40 mM. In various embodiments, the buffering agent is present at a concentration of 5 mM to 30 mM. In various embodiments, the buffering agent is present at a concentration of 5 mM to 20 mM. In various embodiments, the buffering agent is present at a concentration of 5 mM to 10 mM.

In accordance with each of the foregoing aspects and embodiments, in various embodiments, the buffering agent is present at a concentration of about 5 mM. In various embodiments, the buffering agent is present at a concentration of about 10 mM. In various embodiments, the buffering agent is present at a concentration of about 15 mM. In various embodiments, the buffering agent is present at a concentration of about 20 mM. In various embodiments, the buffering agent is present at a concentration of about 25 mM. In various embodiments, the buffering agent is present at a concentration of about 30 mM. In various embodiments, the buffering agent is present at a concentration of about 40 mM. In various embodiments, the buffering agent is present at a concentration of about 50 mM. In various embodiments, the buffering agent is present at a concentration of about 60 mM. In various embodiments, the buffering agent is present at a concentration of about 70 mM. In various embodiments, the buffering agent is present at a concentration of about 80 mM. In various embodiments, the buffering agent is present at a concentration of about 90 mM. In various embodiments, the buffering agent is present at a concentration of about 100 mM.

In accordance with each of the foregoing aspects and embodiments, in various embodiments, the buffering agent is present at a concentration of 5 mM. In various embodiments, the buffering agent is present at a concentration of 10 mM. In various embodiments, the buffering agent is present at a concentration of 15 mM. In various embodiments, the buffering agent is present at a concentration of 20 mM. In various embodiments, the buffering agent is present at a concentration of 25 mM. In various embodiments, the buffering agent is present at a concentration of 30 mM. In various embodiments, the buffering agent is present at a concentration of 40 mM. In various embodiments, the buffering agent is present at a concentration of 50 mM. In various embodiments, the buffering agent is present at a concentration of 60 mM. In various embodiments, the buffering agent is present at a concentration of 70 mM. In various embodiments, the buffering agent is present at a concentration of 80 mM. In various embodiments, the buffering agent is present at a concentration of 90 mM. In various embodiments, the buffering agent is present at a concentration of 100 mM.

In some embodiments, a buffering agent may be a salt of acetic acid, such as a metal alkaline salt of acetic acid, such as a sodium acetate, present in an amount ranging from about 2 mM to about 25 mM, or from 5 mM to about 20 mM, or from about 8 mM to about 15 mM, or at about 10 mM.

In accordance with each of the foregoing aspects and embodiments, in certain embodiments the tonicity agent is selected from erythritol, glycerol, lactitol, maltitol, mannitol, sorbitol, sucrose, threitol, xylitol, and any combination thereof, at a concentration of about 1% (w/v) to about 50% (w/v). In certain embodiments, the tonicity agent is present at a concentration of about 5% (w/v) to about 50% (w/v). In certain embodiments, the tonicity agent is present at a concentration of about 10% (w/v) to about 50% (w/v). In certain embodiments, the tonicity agent is present at a concentration of about 15% (w/v) to about 50% (w/v). In certain embodiments, the tonicity agent is present at a concentration of about 20% (w/v) to about 50% (w/v). In certain embodiments, the tonicity agent is present at a concentration of about 25% (w/v) to about 50% (w/v). In certain embodiments, the tonicity agent is present at a concentration of about 30% (w/v) to about 50% (w/v). In certain embodiments, the tonicity agent is present at a concentration of about 40% (w/v) to about 50% (w/v). In certain embodiments, the tonicity agent is present at a concentration of about 1% (w/v) to about 40% (w/v). In certain embodiments, the tonicity agent is present at a concentration of about 1% (w/v) to about 30% (w/v). In certain embodiments, the tonicity agent is present at a concentration of about 1% (w/v) to about 25% (w/v). In certain embodiments, the tonicity agent is present at a concentration of about 1% (w/v) to about 20% (w/v). In certain embodiments, the tonicity agent is present at a concentration of about 1% (w/v) to about 15% (w/v). In certain embodiments, the tonicity agent is present at a concentration of about 1% (w/v) to about 10% (w/v). In certain embodiments, the tonicity agent is present at a concentration of about 1% (w/v) to about 5% (w/v).

In accordance with each of the foregoing aspects and embodiments, in certain embodiments the tonicity agent is selected from erythritol, glycerol, lactitol, maltitol, mannitol, sorbitol, sucrose, threitol, xylitol, and any combination thereof, at a concentration of 1% (w/v) to 50% (w/v). In certain embodiments, the tonicity agent is present at a concentration of 5% (w/v) to 50% (w/v). In certain embodiments, the tonicity agent is present at a concentration of 10% (w/v) to 50% (w/v). In certain embodiments, the tonicity agent is present at a concentration of 15% (w/v) to 50% (w/v). In certain embodiments, the tonicity agent is present at a concentration of 20% (w/v) to 50% (w/v). In certain embodiments, the tonicity agent is present at a concentration of 25% (w/v) to 50% (w/v). In certain embodiments, the tonicity agent is present at a concentration of 30% (w/v) to 50% (w/v). In certain embodiments, the tonicity agent is present at a concentration of 40% (w/v) to 50% (w/v). In certain embodiments, the tonicity agent is present at a concentration of 1% (w/v) to 40% (w/v). In certain embodiments, the tonicity agent is present at a concentration of 1% (w/v) to 30% (w/v). In certain embodiments, the tonicity agent is present at a concentration of 1% (w/v) to 25% (w/v). In certain embodiments, the tonicity agent is present at a concentration of 1% (w/v) to 20% (w/v). In certain embodiments, the tonicity agent is present at a concentration of 1% (w/v) to 15% (w/v). In certain embodiments, the tonicity agent is present at a concentration of 1% (w/v) to 10% (w/v). In certain embodiments, the tonicity agent is present at a concentration of 1% (w/v) to 5% (w/v).

In accordance with each of the foregoing aspects and embodiments, in certain embodiments the tonicity agent is selected from erythritol, glycerol, lactitol, maltitol, mannitol, sorbitol, sucrose, threitol, xylitol, and any combination thereof, at a concentration of about 1% (w/v). In certain embodiments, the tonicity agent is present at a concentration of about 2% (w/v). In certain embodiments, the tonicity agent is present at a concentration of about 3% (w/v). In certain embodiments, the tonicity agent is present at a concentration of about 4% (w/v). In certain embodiments, the tonicity agent is present at a concentration of about 5% (w/v). In certain embodiments, the tonicity agent is present at a concentration of about 10% (w/v). In certain embodiments, the tonicity agent is present at a concentration of about 15% (w/v). In certain embodiments, the tonicity agent is present at a concentration of about 20% (w/v). In certain embodiments, the tonicity agent is present at a concentration of about 25% (w/v). In certain embodiments, the tonicity agent is present at a concentration of about 30% (w/v). In certain embodiments, the tonicity agent is present at a concentration of about 40% (w/v). In certain embodiments, the tonicity agent is present at a concentration of about 50% (w/v).

In accordance with each of the foregoing aspects and embodiments, in certain embodiments the tonicity agent is selected from erythritol, glycerol, lactitol, maltitol, mannitol, sorbitol, sucrose, threitol, xylitol, and any combination thereof, at a concentration of 1% (w/v). In certain embodiments, the tonicity agent is present at a concentration of 2% (w/v). In certain embodiments, the tonicity agent is present at a concentration of 3% (w/v). In certain embodiments, the tonicity agent is present at a concentration of 4% (w/v). In certain embodiments, the tonicity agent is present at a concentration of 5% (w/v). In certain embodiments, the tonicity agent is present at a concentration of 10% (w/v). In certain embodiments, the tonicity agent is present at a concentration of 15% (w/v). In certain embodiments, the tonicity agent is present at a concentration of 20% (w/v). In certain embodiments, the tonicity agent is present at a concentration of 25% (w/v). In certain embodiments, the tonicity agent is present at a concentration of 30% (w/v). In certain embodiments, the tonicity agent is present at a concentration of 40% (w/v). In certain embodiments, the tonicity agent is present at a concentration of 50% (w/v).

In some embodiments, a polyol may be sorbitol present in amount ranging from about 1 to about 10% (w/v), or from about 2 to about 8% (w/v), or from about 4 to about 6% (w/v), or is at about 5% (w/v).

In accordance with each of the foregoing aspects and embodiments, in certain embodiments the surfactant may be a selected among polysorbates, such as polysorbate 20, polysorbate 40, polysorbate 65, polysorbate 80, polysorbate 81, and polysorbate 85, poloxamers, and any combination thereof, at a concentration of about 0.0001% (w/v) to about 10% (w/v). In certain embodiments, the surfactant is present at a concentration of about 0.0001% (w/v) to about 10% (w/v). In certain embodiments, the surfactant is present at a concentration of about 0.0005% (w/v) to about 5% (w/v). In certain embodiments, the surfactant is present at a concentration of about 0.001% (w/v) to about 3% (w/v). In certain embodiments, the surfactant is present at a concentration of about 0.005% (w/v) to about 2% (w/v). In certain embodiments, the surfactant is present at a concentration of about 0.01% (w/v) to about 1% (w/v). In certain embodiments, the surfactant is present at a concentration of about 0.02% (w/v) to about 0.5% (w/v). In certain embodiments, the surfactant is present at a concentration of about 0.03% (w/v) to about 0.1% (w/v). In certain embodiments, the surfactant is present at a concentration of about 0.04% (w/v) to about 0.08% (w/v). In certain embodiments, the surfactant is present at a concentration of about 0.04% (w/v) to about 0.06% (w/v). In certain embodiments, the surfactant is present at a concentration of about 0.04% (w/v).

In accordance with each of the foregoing aspects and embodiments, in certain embodiments the surfactant is selected from polysorbates, such as polysorbate 20, polysorbate 40, polysorbate 65, polysorbate 80, polysorbate 81, and polysorbate 85, poloxamers, and any combination thereof, at a concentration of 0.0001% (w/v) to 10% (w/v). In certain embodiments, the surfactant is present at a concentration of 0.0005% (w/v) to 10% (w/v). In certain embodiments, the surfactant is present at a concentration of 0.001% (w/v) to 10% (w/v). In certain embodiments, the surfactant is present at a concentration of 0.005% (w/v) to 10% (w/v). In certain embodiments, the surfactant is present at a concentration of 0.01% (w/v) to 10% (w/v). In certain embodiments, the surfactant is present at a concentration of 0.02% (w/v) to 10% (w/v). In certain embodiments, the surfactant is present at a concentration of 0.03% (w/v) to 10% (w/v). In certain embodiments, the surfactant is present at a concentration of 0.04% (w/v) to 10% (w/v). In certain embodiments, the surfactant is present at a concentration of 0.001% (w/v) to 5% (w/v). In certain embodiments, the surfactant is present at a concentration of 0.001% (w/v) to 3% (w/v). In certain embodiments, the surfactant is present at a concentration of 0.001% (w/v) to 2% (w/v). In certain embodiments, the surfactant is present at a concentration of 0.001% (w/v) to 1% (w/v). In certain embodiments, the surfactant is present at a concentration of 0.001% (w/v) to 0.5% (w/v). In certain embodiments, the surfactant is present at a concentration of 0.001% (w/v) to 0.1% (w/v). In certain embodiments, the surfactant is present at a concentration of 0.001% (w/v) to 0.08% (w/v).

In accordance with each of the foregoing aspects and embodiments, in certain embodiments the surfactant is selected from polysorbates, such as polysorbate 20, polysorbate 40, polysorbate 65, polysorbate 80, polysorbate 81, and polysorbate 85, poloxamers, and any combination thereof, at a concentration of about 0.0001% (w/v). In certain embodiments, the surfactant is present at a concentration of about 0.0005% (w/v). In certain embodiments, the surfactant is present at a concentration of about 0.001% (w/v). In certain embodiments, the surfactant is present at a concentration of about 0.005% (w/v). In certain embodiments, the surfactant is present at a concentration of about 0.01% (w/v). In certain embodiments, the surfactant is present at a concentration of about 0.02% (w/v). In certain embodiments, the surfactant is present at a concentration of about 0.03% (w/v). In certain embodiments, the surfactant is present at a concentration of about 0.04% (w/v). In certain embodiments, the surfactant is present at a concentration of about 0.06% (w/v). In certain embodiments, the surfactant is present at a concentration of about 0.08% (w/v). In certain embodiments, the surfactant is present at a concentration of about 0.1% (w/v). In certain embodiments, the surfactant is present at a concentration of about 0.5% (w/v). In certain embodiments, the surfactant is present at a concentration of about 1% (w/v). In certain embodiments, the surfactant is present at a concentration of about 2% (w/v). In certain embodiments, the surfactant is present at a concentration of about 5% (w/v). In certain embodiments, the surfactant is present at a concentration of about 10% (w/v).

In some embodiments, a surfactant may be a polysorbate, such as a polysorbate 80 present in amount ranging from about 0.005 to about 5% (w/v), or from about 0.01 to about 2% (w/v), or from about 0.02 to about 1% (w/v), or from about 0.03 to about 0.08% (w/v), or is at about 0.04% (w/v).

An aspect of the instant disclosure is a pharmaceutical formulation comprising i) anti-human carcinoembryonic antigen-related cell adhesion molecule 5 (hCEACAM5) antibody-drug conjugate (ADC),
ii) Sodium Acetate,
iii) Sorbitol,
iv) Polysorbate 80, and
v) disodium EDTA, at pH 5.5, wherein the ADC consists of huMAb2-3-SPDB-DM4.

In certain embodiments, the pharmaceutical formulation comprises about 1 to about 50 mg/mL huMAb2-3-SPDB-DM4. In certain embodiments, the pharmaceutical formulation comprises about 2 to about 40 mg/mL huMAb2-3-SPDB-DM4. In certain embodiments, the pharmaceutical formulation comprises about 3 to about 30 mg/mL huMAb2-3-SPDB-DM4. In certain embodiments, the pharmaceutical formulation comprises about 4 to about 20 mg/mL huMAb2-3-SPDB-DM4. In certain embodiments, the pharmaceutical formulation comprises about 5 to about 10 mg/mL huMAb2-3-SPDB-DM4. In certain embodiments, the pharmaceutical formulation comprises about 5 mg/mL huMAb2-3-SPDB-DM4.

In certain embodiments, the pharmaceutical formulation comprises 1-50 mg/mL huMAb2-3-SPDB-DM4. In certain embodiments, the pharmaceutical formulation comprises 2-40 mg/mL huMAb2-3-SPDB-DM4. In certain embodiments, the pharmaceutical formulation comprises 3-30 mg/mL huMAb2-3-SPDB-DM4. In certain embodiments, the pharmaceutical formulation comprises 4-20 mg/mL huMAb2-3-SPDB-DM4. In certain embodiments, the pharmaceutical formulation comprises 5-10 mg/mL huMAb2-3-SPDB-DM4. In certain embodiments, the pharmaceutical formulation comprises 5 mg/mL huMAb2-3-SPDB-DM4. In certain embodiments, the pharmaceutical formulation comprises 10 mg/mL huMAb2-3-SPDB-DM4.

In some embodiments, a chelating agent may be selected among diethylenetriaminepentaacetic acid (DTPA), ethylenediaminetetraacetic acid (EDTA), hydroxyethylenediamine tri acetic acid (HEDTA), nitrilotriacetic acid, ethylene glycol-bis(β-aminoethyl ether)-N,N,N',N'-tetraacetic acid (EGTA), and salts thereof, e.g., disodium EDTA, calcium disodium EDTA, tetrasodium EDTA, present in amount ranging from about 1 to about 50 μM, or from about 1 to about 40 μM, or from about 1 to about 30 μM, or from 1 to about 20 μM, or from about 1 to about 10 μM. In some embodiments, a chelating agent may be present in an amount from about 10 to about 50 μM, or from about 10 to about 40 μM, or from about 10 to about 20 μM disodium EDTA. In some embodiments, a chelating agent may be present at about 10 μM, or at about 20 μM, or at about 30 μM, or at about 40 or μM, at about 50 μM.

In certain embodiments, the pharmaceutical composition comprises about 1 to about 50 μM disodium EDTA. In certain embodiments, the pharmaceutical composition comprises about 1 to about 40 μM disodium EDTA. In certain embodiments, the pharmaceutical composition comprises about 1 to about 30 μM disodium EDTA. In certain embodiments, the pharmaceutical composition comprises about 1 to about 20 μM disodium EDTA. In certain embodiments, the pharmaceutical composition comprises about 1 to about 10 μM disodium EDTA. In certain embodiments, the pharmaceutical composition comprises about 10 to about 50 μM disodium EDTA. In certain embodiments, the pharmaceutical composition comprises about 10 to about 40 μM disodium EDTA. In certain embodiments, the pharmaceutical composition comprises about 10 to about 20 μM disodium EDTA. In certain embodiments, the pharmaceutical composition comprises about 10 μM disodium EDTA. In certain embodiments, the pharmaceutical composition comprises about 20 μM disodium EDTA. In certain embodiments, the pharmaceutical composition comprises about 30 μM disodium EDTA. In certain embodiments, the pharmaceutical composition comprises about 40 μM disodium EDTA. In certain embodiments, the pharmaceutical composition comprises about 50 μM disodium EDTA.

In certain embodiments, the pharmaceutical composition comprises 1 to 50 μM disodium EDTA. In certain embodiments, the pharmaceutical composition comprises 1 to 40 μM disodium EDTA. In certain embodiments, the pharmaceutical composition comprises 1 to 30 μM disodium EDTA. In certain embodiments, the pharmaceutical composition comprises 1 to 20 μM disodium EDTA. In certain embodiments, the pharmaceutical composition comprises 1 to 10 μM disodium EDTA. In certain embodiments, the pharmaceutical composition comprises 10 to 50 μM disodium EDTA. In certain embodiments, the pharmaceutical composition comprises 10 to 40 μM disodium EDTA. In certain embodiments, the pharmaceutical composition comprises 10 to 20 μM disodium EDTA. In certain embodiments, the pharmaceutical composition comprises 10 μM disodium EDTA. In certain embodiments, the pharmaceutical composition comprises 20 μM disodium EDTA. In certain embodiments, the pharmaceutical composition comprises 30 μM disodium EDTA. In certain embodiments, the pharmaceutical composition comprises 40 μM disodium EDTA. In certain embodiments, the pharmaceutical composition comprises 50 μM disodium EDTA.

In some embodiments, a chelating agent may be EDTA, or salt thereof, present in an amount ranging from about 1 to about 30 μM, or from about 2 to about 25 μM, or from about 5 to about 20 μM, or from about 8 to about 15 μM, or may be at about 10 μM.

In certain embodiments, the pharmaceutical formulation comprises i) 5 mg/mL anti-human carcinoembryonic antigen-related cell adhesion molecule 5 (hCEACAM5) antibody-drug conjugate (ADC),
ii) Sodium Acetate 10 mM,
iii) Sorbitol 5% (w/v),
iv) 0.04% (w/v) Polysorbate 80, and
v) 1-50 μM disodium EDTA,
at pH 5.5, wherein the ADC consists of huMAb2-3-SPDB-DM4.

In certain embodiments, the pharmaceutical formulation comprises i) 5 mg/mL anti-human carcinoembryonic antigen-related cell adhesion molecule 5 (hCEACAM5) antibody-drug conjugate (ADC),
ii) Sodium Acetate 10 mM,
iii) Sorbitol 5% (w/v),
iv) 0.04% (w/v) Polysorbate 80, and
v) 1 μM disodium EDTA,
at pH 5.5, wherein the ADC consists of huMAb2-3-SPDB-DM4.

In certain embodiments, the pharmaceutical formulation comprises i) 5 mg/mL anti-human carcinoembryonic antigen-related cell adhesion molecule 5 (hCEACAM5) antibody-drug conjugate (ADC),
ii) Sodium Acetate 10 mM,
iii) Sorbitol 5% (w/v),
iv) 0.04% (w/v) Polysorbate 80, and
v) 10 μM disodium EDTA,
at pH 5.5, wherein the ADC consists of huMAb2-3-SPDB-DM4.

In certain embodiments, the pharmaceutical formulation comprises i) 5 mg/mL anti-human carcinoembryonic antigen-related cell adhesion molecule 5 (hCEACAM5) antibody-drug conjugate (ADC),
ii) Sodium Acetate 10 mM,
iii) Sorbitol 5% (w/v),
iv) 0.04% (w/v) Polysorbate 80, and
v) 50 μM disodium EDTA,
at pH 5.5, wherein the ADC consists of huMAb2-3-SPDB-DM4.

The formulations disclosed herein are generally suitable for administration to a subject by injection or infusion, for example by intravenous injection or infusion. The formulations disclosed herein are generally suitable for administration to a human subject by injection or infusion, for example by intravenous injection or infusion.

Methods

An aspect of the instant disclosure is a method of treating a cancer, the method comprising administering to a subject in need thereof an effective amount of any one of the foregoing pharmaceutical formulations.

In accordance with such method, in certain embodiments, the pharmaceutical formulation comprises i) anti-human carcinoembryonic antigen-related cell adhesion molecule 5 (hCEACAM5) antibody-drug conjugate (ADC),
ii) a buffering agent,
iii) a tonicity agent, for example a polyol,
iv) a surfactant, for example a polysorbate, and
v) optionally a chelating agent,
at pH about 5.0 to about 6.5, wherein the ADC consists of huMAb2-3-SPDB-DM4.

In certain embodiments in accordance with the method, the pharmaceutical formulation comprises i) anti-human carcinoembryonic antigen-related cell adhesion molecule 5 (hCEACAM5) antibody-drug conjugate (ADC),
ii) a buffering agent,
iii) a polyol,
iv) a polysorbate, and
v) optionally a chelating agent,
at pH about 5.0 to about 6.5, wherein the ADC consists of huMAb2-3-SPDB-DM4.

In certain embodiments in accordance with the method, the pharmaceutical formulation comprises i) anti-human carcinoembryonic antigen-related cell adhesion molecule 5 (hCEACAM5) antibody-drug conjugate (ADC),
ii) a buffering agent, for example selected from the group consisting of acetate, arginine, histidine, citrate, and any combination thereof, or for example being acetate,
iii) a polyol, for example a sorbitol,
iv) a polysorbate, for example polysorbate 80, and
v) optionally a chelating agent,
at pH about 5.0 to about 6.5, wherein the ADC consists of huMAb2-3-SPDB-DM4.

In certain embodiments in accordance with the method, the pharmaceutical formulation comprises i) anti-human carcinoembryonic antigen-related cell adhesion molecule 5 (hCEACAM5) antibody-drug conjugate (ADC),
ii) a buffering agent, for example selected from the group consisting of acetate, arginine, histidine, citrate, and any combination thereof, or for example being acetate,
iii) a sorbitol, iv) a polysorbate, and v) optionally a chelating agent, at pH about 5.0 to about 6.5, wherein the ADC consists of huMAb2-3-SPDB-DM4.

In certain embodiments in accordance with the method, the pharmaceutical formulation comprises i) anti-human carcinoembryonic antigen-related cell adhesion molecule 5 (hCEACAM5) antibody-drug conjugate (ADC), ii) a buffering agent, for example selected from the group consisting of acetate, arginine, histidine, citrate, and any combination thereof, or for example being acetate, iii) a polyol, iv) polysorbate 80, and v) optionally a chelating agent, at pH about 5.0 to about 6.5, wherein the ADC consists of huMAb2-3-SPDB-DM4.

In certain embodiments in accordance with the method, the pharmaceutical formulation comprises i) anti-human carcinoembryonic antigen-related cell adhesion molecule 5 (hCEACAM5) antibody-drug conjugate (ADC), ii) a buffering agent, for example selected from the group consisting of acetate, arginine, histidine, citrate, and any combination thereof, or for example being acetate, iii) sorbitol, iv) polysorbate 80, and v) optionally a chelating agent, at pH about 5.0 to about 6.5, wherein the ADC consists of huMAb2-3-SPDB-DM4.

In certain embodiments in accordance with the method, the pharmaceutical formulation comprises i) anti-human carcinoembryonic antigen-related cell adhesion molecule 5 (hCEACAM5) antibody-drug conjugate (ADC), ii) sodium acetate, iii) sorbitol, iv) polysorbate 80, and v) optionally a chelating agent, at pH about 5.0 to about 6.5, wherein the ADC consists of huMAb2-3-SPDB-DM4.

In certain embodiments in accordance with the method, the pharmaceutical formulation comprises i) anti-human carcinoembryonic antigen-related cell adhesion molecule 5 (hCEACAM5) antibody-drug conjugate (ADC), ii) a buffering agent, iii) a tonicity agent, iv) a polysorbate, and v) a chelating agent, at pH about 5.0 to about 6.5, wherein the ADC consists of huMAb2-3-SPDB-DM4.

In certain embodiments in accordance with the method, the pharmaceutical formulation comprises i) anti-human carcinoembryonic antigen-related cell adhesion molecule 5 (hCEACAM5) antibody-drug conjugate (ADC), ii) a buffering agent, iii) a polyol, iv) a polysorbate, and v) a chelating agent, at pH about 5.0 to about 6.5, wherein the ADC consists of huMAb2-3-SPDB-DM4.

In certain embodiments in accordance with the method, the pharmaceutical formulation comprises i) anti-human carcinoembryonic antigen-related cell adhesion molecule 5 (hCEACAM5) antibody-drug conjugate (ADC), ii) a buffering agent selected from acetate, arginine, histidine, citrate, and any combination thereof, iii) a tonicity agent, iv) Polysorbate 80, and v) ethylenediaminetetraacetic acid (EDTA), at pH about 5.0 to about 6.5, wherein the ADC consists of huMAb2-3-SPDB-DM4.

In certain embodiments in accordance with the method, the pharmaceutical formulation comprises i) anti-human carcinoembryonic antigen-related cell adhesion molecule 5 (hCEACAM5) antibody-drug conjugate (ADC), ii) a buffering agent selected from acetate, histidine, citrate, and any combination thereof, iii) a tonicity agent selected from erythritol, glycerol, lactitol, maltitol, mannitol, sorbitol, sucrose, threitol, xylitol, and any combination thereof, iv) Polysorbate 80, and v) EDTA, at pH about 5.0 to about 6.5, wherein the ADC consists of huMAb2-3-SPDB-DM4.

In certain embodiments in accordance with the method, the pharmaceutical formulation comprises i) anti-human carcinoembryonic antigen-related cell adhesion molecule 5 (hCEACAM5) antibody-drug conjugate (ADC), ii) a buffering agent selected from acetate, histidine, citrate, and any combination thereof, iii) sorbitol, iv) polysorbate 80, and v) EDTA, at pH about 5.0 to about 6.5, wherein the ADC consists of huMAb2-3-SPDB-DM4.

In certain embodiments in accordance with the method, the pharmaceutical formulation comprises i) anti-human carcinoembryonic antigen-related cell adhesion molecule 5 (hCEACAM5) antibody-drug conjugate (ADC), ii) sodium acetate, iii) sorbitol, iv) polysorbate 80, and v) EDTA, at pH about 5.0 to about 6.5, wherein the ADC consists of huMAb2-3-SPDB-DM4.

In certain embodiments in accordance with the method, the pharmaceutical formulation comprises i) anti-human carcinoembryonic antigen-related cell adhesion molecule 5 (hCEACAM5) antibody-drug conjugate (ADC), ii) a buffering agent selected from acetate, histidine, citrate, and any combination thereof, at a concentration of about 5 mM to about 100 mM, iii) a tonicity agent selected from erythritol, glycerol, lactitol, maltitol, mannitol, sorbitol, sucrose, threitol, xylitol, and any combination thereof, iv) Polysorbate 80, and v) EDTA, at pH about 5.0 to about 6.5, wherein the ADC consists of huMAb2-3-SPDB-DM4.

In certain embodiments in accordance with the method, the pharmaceutical formulation comprises i) anti-human carcinoembryonic antigen-related cell adhesion molecule 5 (hCEACAM5) antibody-drug conjugate (ADC), ii) a buffering agent selected from acetate, histidine, citrate, and any combination thereof,
iii) a tonicity agent selected from erythritol, glycerol, lactitol, maltitol, mannitol, sorbitol, sucrose, threitol, xylitol, and any combination thereof, at a concentration of about 1% (w/v) to about 50% (w/v),
iv) Polysorbate 80, and
v) EDTA,
at pH about 5.0 to about 6.5,
wherein the ADC consists of huMAb2-3-SPDB-DM4.

In certain embodiments in accordance with the method, the pharmaceutical formulation comprises
i) anti-human carcinoembryonic antigen-related cell adhesion molecule 5 (hCEACAM5) antibody-drug conjugate (ADC),
ii) a buffering agent selected from acetate, histidine, citrate, and any combination thereof, at a concentration of about 5 mM to about 100 mM,
iii) a tonicity agent selected from erythritol, glycerol, lactitol, maltitol, mannitol, sorbitol, sucrose, threitol, xylitol, and any combination thereof, at a concentration of about 1% (w/v) to about 50% (w/v),
iv) Polysorbate 80, and
v) EDTA,
at pH about 5.0 to about 6.5,
wherein the ADC consists of huMAb2-3-SPDB-DM4.

In certain embodiments in accordance with the method, the pharmaceutical formulation comprises
i) anti-human carcinoembryonic antigen-related cell adhesion molecule 5 (hCEACAM5) antibody-drug conjugate (ADC),
ii) Sodium Acetate,
iii) Sorbitol,
iv) Polysorbate 80, and
v) disodium EDTA,
at pH 5.5,
wherein the ADC consists of huMAb2-3-SPDB-DM4.

In certain embodiments in accordance with the method, the pharmaceutical formulation comprises
i) 5 mg/mL anti-human carcinoembryonic antigen-related cell adhesion molecule 5 (hCEACAM5) antibody-drug conjugate (ADC),
ii) Sodium Acetate 10 mM,
iii) Sorbitol 5% (w/v),
iv) 0.04% (w/v) Polysorbate 80, and
v) 1-50 μM disodium EDTA,
at pH 5.5,
wherein the ADC consists of huMAb2-3-SPDB-DM4.

In certain embodiments in accordance with the method, the pharmaceutical formulation comprises
i) 5 mg/mL anti-human carcinoembryonic antigen-related cell adhesion molecule 5 (hCEACAM5) antibody-drug conjugate (ADC),
ii) Sodium Acetate 10 mM,
iii) Sorbitol 5% (w/v),
iv) 0.04% (w/v) Polysorbate 80, and
v) 1 μM disodium EDTA,
at pH 5.5,
wherein the ADC consists of huMAb2-3-SPDB-DM4.

In certain embodiments in accordance with the method, the pharmaceutical formulation comprises
i) 5 mg/mL anti-human carcinoembryonic antigen-related cell adhesion molecule 5 (hCEACAM5) antibody-drug conjugate (ADC),
ii) Sodium Acetate 10 mM,
iii) Sorbitol 5% (w/v),
iv) 0.04% (w/v) Polysorbate 80, and
v) 10 μM disodium EDTA,
at pH 5.5,
wherein the ADC consists of huMAb2-3-SPDB-DM4.

In certain embodiments in accordance with the method, the pharmaceutical formulation comprises
i) 5 mg/mL anti-human carcinoembryonic antigen-related cell adhesion molecule 5 (hCEACAM5) antibody-drug conjugate (ADC),
ii) Sodium Acetate 10 mM,
iii) Sorbitol 5% (w/v),
iv) 0.04% (w/v) Polysorbate 80, and
v) 50 μM disodium EDTA,
at pH 5.5,
wherein the ADC consists of huMAb2-3-SPDB-DM4.

In certain embodiments, the cancer is a high carcinoembryonic antigen-related cell adhesion molecule cancer.

In certain embodiments, the cancer is selected from the group consisting of colorectal, gastric, lung, breast, prostate, ovary, cervical, and bladder cancer.

In certain embodiments, the cancer is selected from the group consisting of lung, breast, prostate, ovary, cervical, and bladder cancer.

In certain embodiments, the cancer is lung cancer.

In certain embodiments, the lung cancer is non-squamous non-small cell lung carcinoma.

In certain embodiments, the subject is a human.

In certain embodiments, the cancer is selected from the group consisting of colorectal, gastric, lung, breast, prostate, ovary, cervical, and bladder cancer.

In certain embodiments, the cancer is selected from the group consisting of lung, breast, prostate, ovary, cervical, and bladder cancer.

In certain embodiments, the cancer is lung cancer.

In certain embodiments, the lung cancer is non-squamous non-small cell lung carcinoma.

Non-small cell lung cancer (NSCLC) is the most common type of lung cancer. It usually grows and spreads more slowly than less-common small cell lung cancer. There are three main subtypes of non-small cell lung cancer, including squamous cell carcinoma (25% of lung cancers), adenocarcinoma (40% of lung cancers), and large cell carcinoma (10% of lung cancers). Non-squamous non-small cell lung cancer thus includes adenocarcinoma (40% of lung cancers) and large cell carcinoma (10% of lung cancers).

In certain embodiments, the subject is a human.

EXAMPLES

Example 1. Initial Formulation of huMAb2-3-SPDB-DM4 huMAb2-3-SPDB-DM4 (see FIG. 1) was initially developed as a concentrate for solution for infusion. The dosage form was a solution at 5 mg/mL for single use in glass vial stored at 5° C. The drug substance was developed as a bulk frozen solution at −20° C. in polycarbonate bottle, representative of other containers. The aim of this initial study was to identify a set of pH buffering systems and stabilizing excipients. A total of 8 formulations with the combined excipients were tested in thermal stress at 40° C., 25° C. and 5° C. and upon freeze/thaw stress and mechanical stress (shaking).

Prototypes are presented in Table 1.

TABLE 1

Combination of excipients around pH 6.0 for huMAb2-3-SPDB-DM4 evaluation

| N ° | Buffer System | Excipient | pH |
|---|---|---|---|
| A | Acetate 10 mM | Sucrose 2.5%<br>Mannitol 3.75%<br>PS80 0.005% | 5.5 |
| B | Acetate 10 mM | Sucrose 2.5%<br>Mannitol 3.75%<br>PS80 0.1% | 5.5 |
| C | Histidine 10 mM | Sucrose 5.0%<br>Glycine 130 mM<br>PS80 0.1% | 5.5 |
| D | Histidine 10 mM | Sucrose 10%<br>PS80 0.1% | 6.5 |
| E | Citrate 10 mM | Sucrose 10%<br>PS80 0.1% | 6.0 |
| F | Acetate 10 mM | Sucrose 10%<br>PS80 0.1% | 6.0 |
| G | Acetate 10 mM | Sucrose 10%<br>PS80 0.1% | 5.5 |
| H | Acetate 10 mM | Sucrose 10%<br>PS20 0.1% | 5.5 |

Methods

UF/DF Procedure

The starting material was provided in histidine buffer. To manufacture acetate-based prototypes (prototypes A, B, F, G, H), the starting material was processed for diafiltration on Cogent µScale system with Pellicon 3® cassette against Acetate 10 mM pH 5.5 (3 membranes of 88 $cm^2$, 68.7 g of protein/$m^2$ membrane). To manufacture citrate-based prototype (prototype E), the starting material was processed for diafiltration on Cogent µScale system with Pellicon 3® cassette against Citrate 10 mM pH 6.0 (1 membrane of 88 $cm^2$, 51.4 g of protein/$m^2$ membrane).

In both cases, the diafiltration was stopped after passing 10 volumes of diafiltration buffer. After the diafiltration, concentration was targeted to 5 mg/mL by adding appropriate concentrated 2× solution as described in Table 3.

TABLE 3

Concentrated excipient solution 2 × recipes

| N° | Buffer System | Excipient | Targeted pH |
|---|---|---|---|
| A | Acetate 10 mM | Sucrose 5%<br>Mannitol 7.5%<br>PS80 0.01% | 5.5 |
| B | Acetate 10 mM | Sucrose 5%<br>Mannitol 7.5%<br>PS80 0.2% | 5.5 |
| C | Histidine 10 mM | Sucrose 10%<br>Glycine 260 mM | 5.5 |
| D | Histidine 10 mM | PS80 0.2%<br>Sucrose 20% | 6.5 |
| E | Citrate 10 mM | PS80 0.2%<br>Sucrose 20% | 6.0 |
| F | Acetate 10 mM | PS80 0.2%<br>Sucrose 20% | 6.0 |
| G | Acetate 10 mM | PS80 0.2%<br>Sucrose 20% | 5.5 |
| H | Acetate 10 mM | PS80 0.2%<br>Sucrose 20%<br>PS20 0.2% | 5.5 |

Filtration 0.2 µm

All formulations were filtered on 0.2 µm filters after formulation with concentrated 2× solutions and collected on Nalgene® (HDPE) bottles before filling.

Stress Conditions

Thermal Stress

Formulation assays A to H were stored at 40° C. for 2 weeks; at 5° C., 25° C. and 40° C. for 4 weeks before analyses.

Freeze/Thaw Cycles

Formulation assays A to H were frozen at −20° C. or −80° C. and thawed at room temperature. 3 cycles of freeze/thaw procedure were performed and the formulations were then analyzed.

Shaking Stress

Formulation assays A to H were shaken in vials during 15 hours via orbital shaking at a speed of 350 rpm.

Analytical Methods

The following analytical methods were performed during the study:

Visual inspection for appearance (clarity, color and particles): the vials are inspected 5 s on white surface then on black surface of the visual inspection table.

Protein Concentration and DAR by UV measurement: OD at 280 nm and 254 nm measured using below absorptivity. Dilution factor of the solution for examination: F=10.

Absorbance of the solution for examination at 254 nm: $A254D$

Absorbance of the solution for examination at 280 nm: $A280D$

Molecular weight of naked antibody $h4D4$=144522 g/mol

Molecular weight of $DM4$=780 g/mol

Molar extinction coefficient of $DM4$ at 280 nm=4927 $L^*mol^{-1}{}^*cm^{-1}$

Molar extinction coefficient of naked antibody $h4D4$ at 280 nm=201400 $L^*mol^{-1}{}^*cm^{-1}$ $A254/A280$ of $h4D4$=0.43

$A254/A280$ of $DM4$=4.83

$$[\text{Drug}]\ (M)=[A254-(0.43\times A280)]/[(4.83\times 4927)-(0.43\times 4927)]$$

$$[\text{Drug}]\ (\text{mg/mL})=[\text{Drug}]\ (M)\times 780\times F$$

$$[\text{Protein}]\ (M)=[A280-4927\times[\text{Drug}]\ (M)]/201400$$

$$[\text{Protein}]\ (\text{mg/mL})=[\text{Protein}]\ (M)\times 144522\times F$$

Turbidity (OD at 350 nm) for opalescence characterization: the absorbance of the solution is measured at 350 nm, on 0.8 mL of non-diluted solution.

Protein purity by SEC-UPLC: Size-exclusion ultra-performance liquid chromatography (SEC-UPLC) was performed for samples A, B, G and H, at T0, after 2 and 4 weeks at 40° C. and after 4 weeks at 5° C.

SEC-UPLC Conditions:

Column: BEH 200, 1.7 µm, 300 mm*4.6 mm

Flow: 0.30 mL/min

Detection: 230 nm

Column temperature: 30° C.±2° C.

Syringe temperature: 5° C.±0.3° C.

Volume of injection: 4 µL

Analysis time: 17 min

Phase mobile D-PBS (2×): prepared with D-PBS (10×) (Dulbecco's Phosphate Buffered Saline (D-PBS) (10×)), reference Invitrogen: 14200083: dilute this solution in 1/5 with water for injection (WFI) and filtrate on 0.22 μm. ADS batch was used as reference within each sequences (injection of 5 μL at 5 g/L).

Protein Purity by SDS-PAGE:

Measured only at T0 and after 2 at weeks 40° C. Samples are prepared in reduced and non-reduced conditions (by addition of nem) and migrated on a 4-12% Bis-Tris gel. The migration buffer is manufactured by diluting 50 mL of Nu-Page MOPS SDS buffer 20× in sqf 1000 mL of purified water. Migration parameters are 135V during 90 minutes. Gels are colored with a Bleu rotiphorese solution.

Charge Heterogeneity by iCIEF:

4 weeks analysis realized only for acetate formulations at pH 5.5.

IcIEF is performed using a cIEF Cartbridge FC-coated with a Convergent Biosciences iCE280 imaged capillary electrophoresis system. Samples are diluted in a Master mix containing Pharmalyte 3-10, Pharmalyte 8-10.5, 4M Urea, 0.35% Methyl Cellulose 1% and pI markers.

Each sample is injected into the capillary with an autosampler. After focusing, the detection is performed by a CCD camera which realizes a direct measurement of the 280 nm UV absorbance. The iCE280 software calculates the apparent pI of each separated peak and Empower allows a quantification of the isoform by normalization per area.

Free Maytansinoids:

4 weeks analysis realized only for formulations at pH 5.5.

Free maytansinoids are measured by RP-HPLC with two columns: a first column to separate the protein from the free maytansinoids, and a second column to separate free maytansinoids species and detect them on a PDA detector. Mobile phase A is a 0.1% trifluoroacetic acid solution in purified water. Mobile phase B is a 0.08% trifluoroacetic acid solution in acetonitrile. DM4 solutions are used as reference.

- DSC (differential scanning calorimetry) for thermal stability performed only at T0.
- DLS (dynamic light scattering) for colloidal aggregation state: Size average of particles and distribution. 4 weeks analysis realized only for formulations at pH 5.5.
- FCM (flow cytometry) for the sub-visible aggregation state: Morphological analysis and counting of particles. 4 weeks analysis realized only for formulations at pH 5.5.

Results and Discussion

Observation and SEC Analysis of DS in Histidine Buffer and after TFF in Acetate and Citrate Buffers At reception the batch of DS in histidine buffer post filtration 0.2 μm was slightly opalescent with particles. The results after UFDF in acetate and citrate buffers are given in Table 4.

TABLE 4

| UFDF results | | | | | | |
|---|---|---|---|---|---|---|
| Batch | Yield of TFF (%) | Process time and volume | Concentration Post UFDF (mg/mL) | Purity (%) Monomer | HMW (%) | LMW (%) |
| After TFF in Acetate Buffer pH 5.5 | 92.0 | 46 min for 160 mL | 11.3 | 94.2 | 3.0 | 2.75 |

TABLE 4-continued

| UFDF results | | | | | | |
|---|---|---|---|---|---|---|
| Batch | Yield of TFF (%) | Process time and volume | Concentration Post UFDF (mg/mL) | Purity (%) Monomer | HMW (%) | LMW (%) |
| After TFF in Citrate Buffer pH 6.0 | 81.5 | 68 min for 40 mL | 12.7 | 94.4 | 3.1 | 2.5 |

Acetate buffer seemed better with regards to opalescence and yield.

Stress Studies

Analysis at T0

Figure 2:
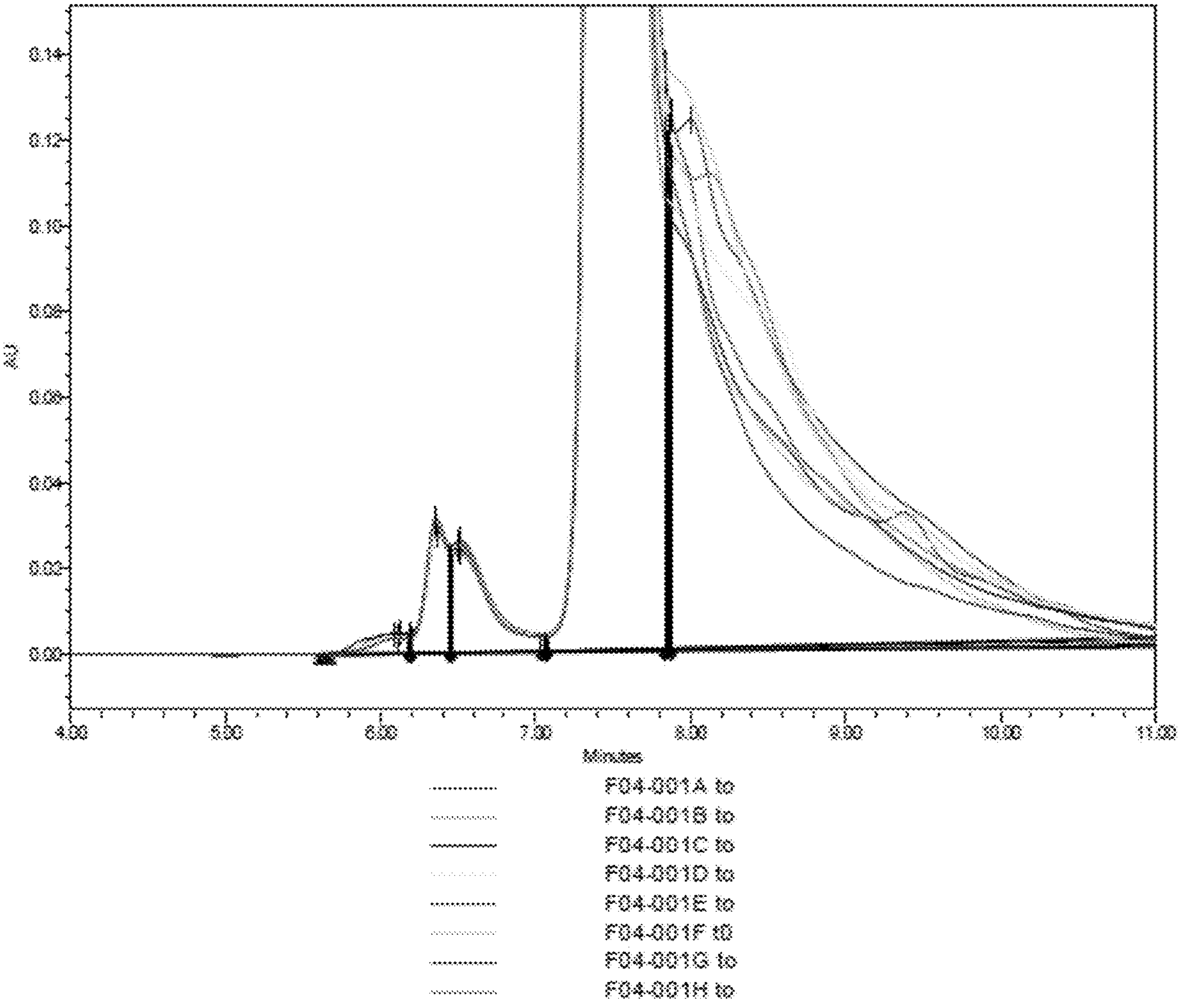
FIG. 2 is a graph depicting SEC-UPLC T0 analysis chromatograms of prototype formulations A-H. Shown are superposition of SEC-HPLC graphs for prototypes A-H at T0. See Example 3.

Prototypes are equivalent at T0 for visual inspection, FCM, DLS, SEC-UPLC (FIG. 2) and icIEF analytical assays:

- regarding visual inspection, all the formulations were very slightly opalescent and contained no visible particles.
- regarding DLS, all the formulations were polydisperse with a PDI superior to 30%.

Figure 3:
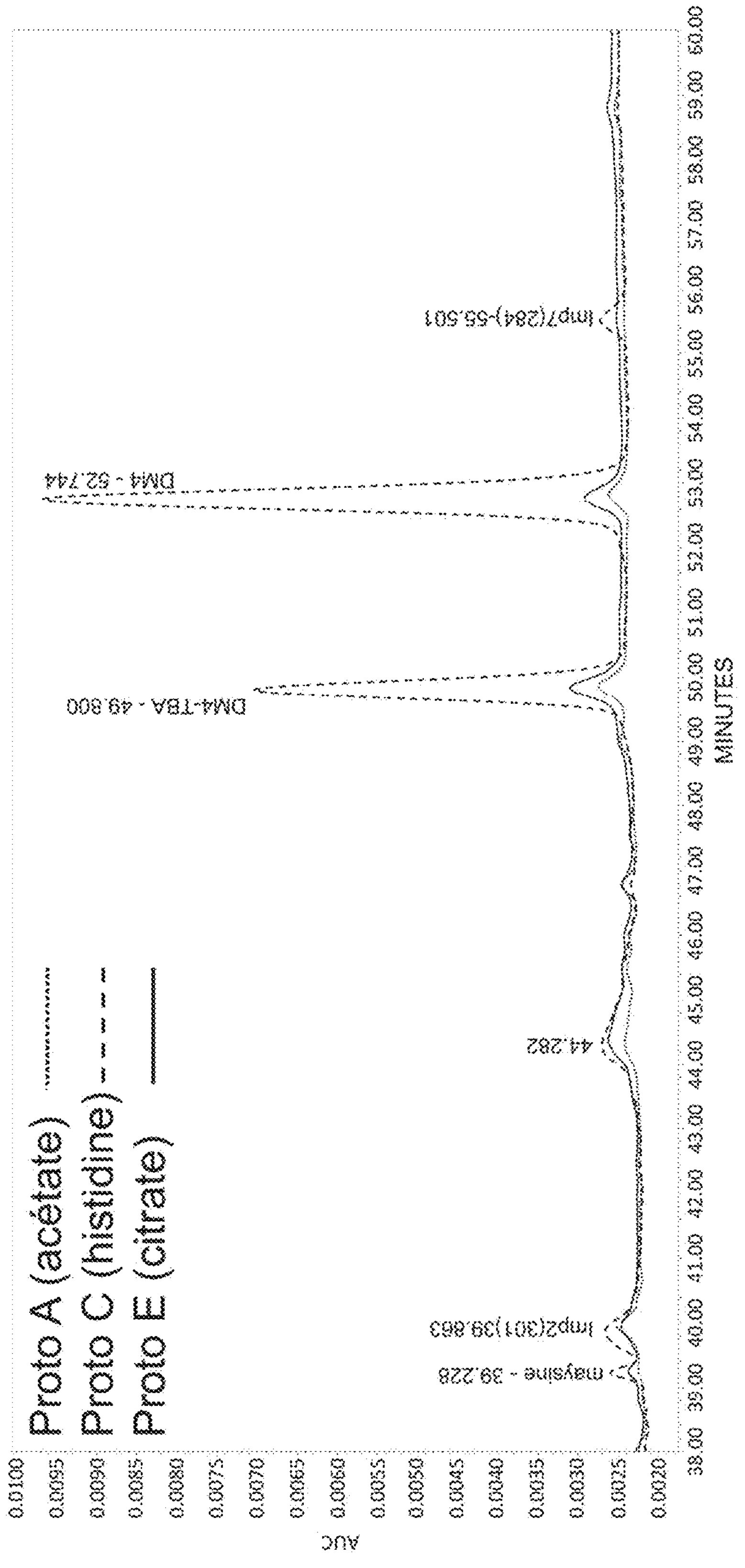
FIG. 3 is a graph depicting t0 analysis chromatograms of free maytansinoids for prototypes A (acetate), C (histidine), and E (citrate). Shown are free maytansinoids for prototypes A (medium grey), C (light grey) and E (heavy grey) at T0. X-axis, minutes; Y-axis, AU.
Figure 4A:
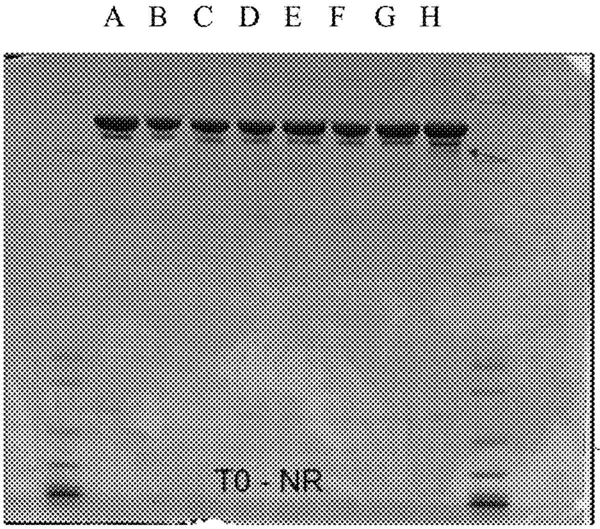
FIG. 4A is a photographic image of SDS-PAGE at t0 of prototype formulations A-H, non-reducing conditions.
Figure 4B:
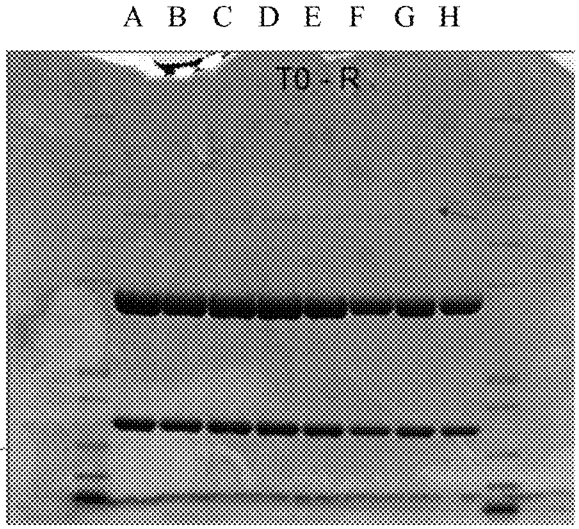
FIG. 4B is a photographic image of SDS-PAGE at t0 of prototype formulations A-H, reducing conditions.

Some differences between prototypes could be observed at T0:

- Regarding results of DSC, Tm was higher with Acetate buffer (pH 5.5 or 6).
- For free maytansinoids, total content was lower in acetate or citrate buffers and higher in histidine buffer (<0.1% for acetate and citrate buffers and around 0.6% for histidine buffer). See FIG. 3.
- Concerning results of SDS PAGE, formulations were similar except formulations G and H which had a different profile. Formulation H in non-reduced condition presents a supplementary band at 127 kDa, and Formulation Gin reduced condition presents a supplementary band at 89 kDa (FIGS. 4A and 4B).

Thermal Stress

Figure 5:
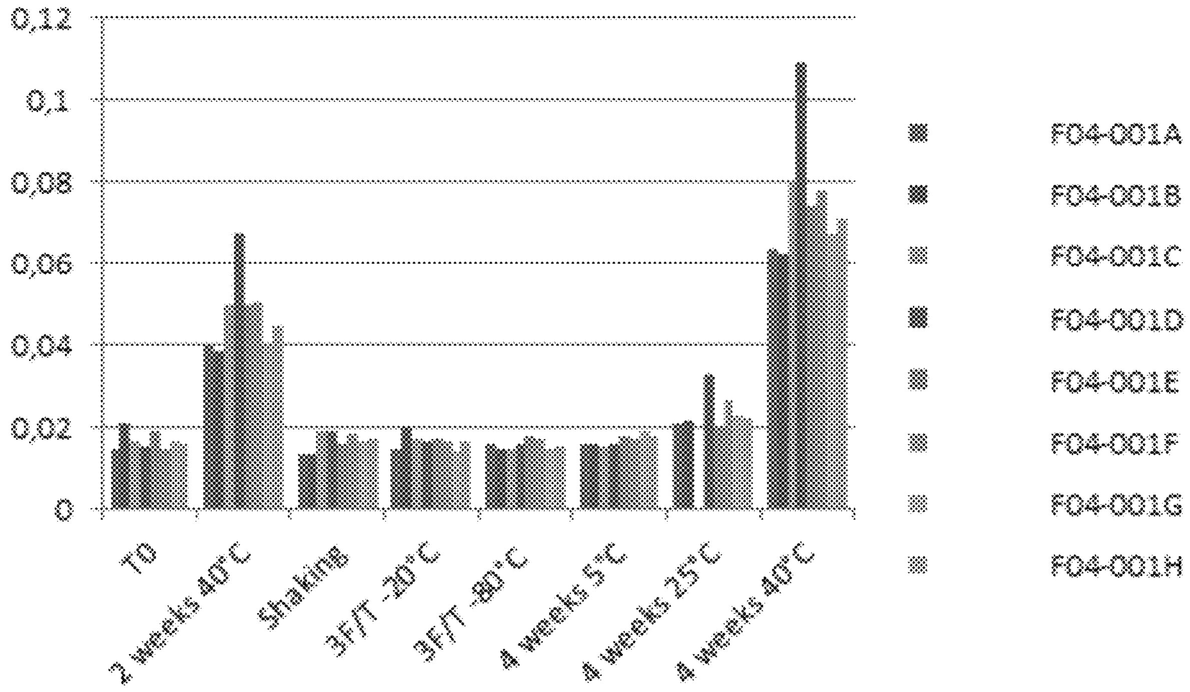
FIG. 5 is a graph depicting evolution of OD 350 nm after indicated stress. Y-axis, OD350 nm. For each stress condition, prototypes appear from A to H.

After 4 weeks at 5° C. and 25° C., all prototypes were similar for analyzed parameters (visual inspection, SEC-HPLC, FCM, DLS, free maytansinoids, is IEF) except prototype C after 4W25° C. that is suspected of contamination (as related to pH, concentration, DLS, FCM). See turbidity results FIG. 5.

After 2 weeks and 4 weeks at 40° C., prototypes are equivalent for protein concentration, SDS-PAGE, visual inspection analytical assays:

- After 2 weeks at 40° C., a new band at 145 kDa was detected for all formulations in SDS PAGE reduced conditions.
- After 2 weeks at 40° C., with regard to visual inspection, all the formulations were very slightly opalescent. Nevertheless, after 40° C. stress, no real evolution was observed versus T0.

Figure 6:
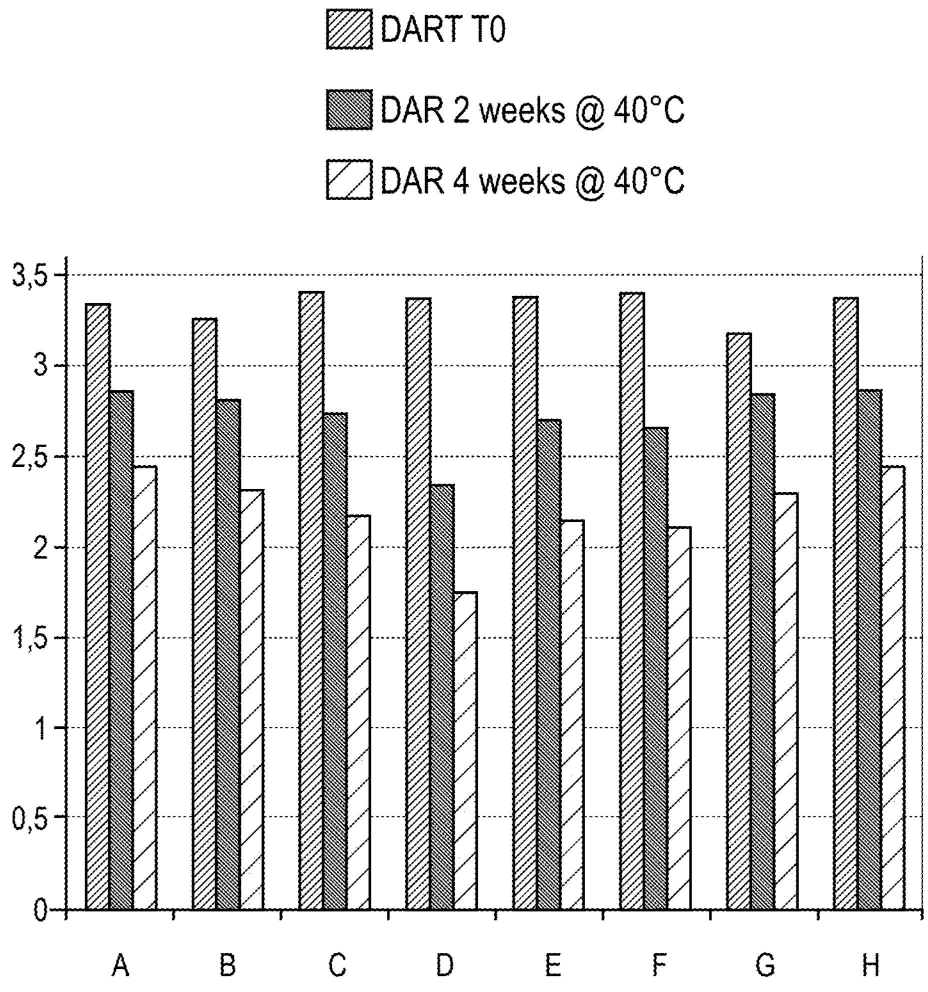
FIG. 6 is a graph depicting evolution of drug-to-antibody ratio (DAR) after indicated thermal stress. X-axis, prototype formulation.
Figure 7:
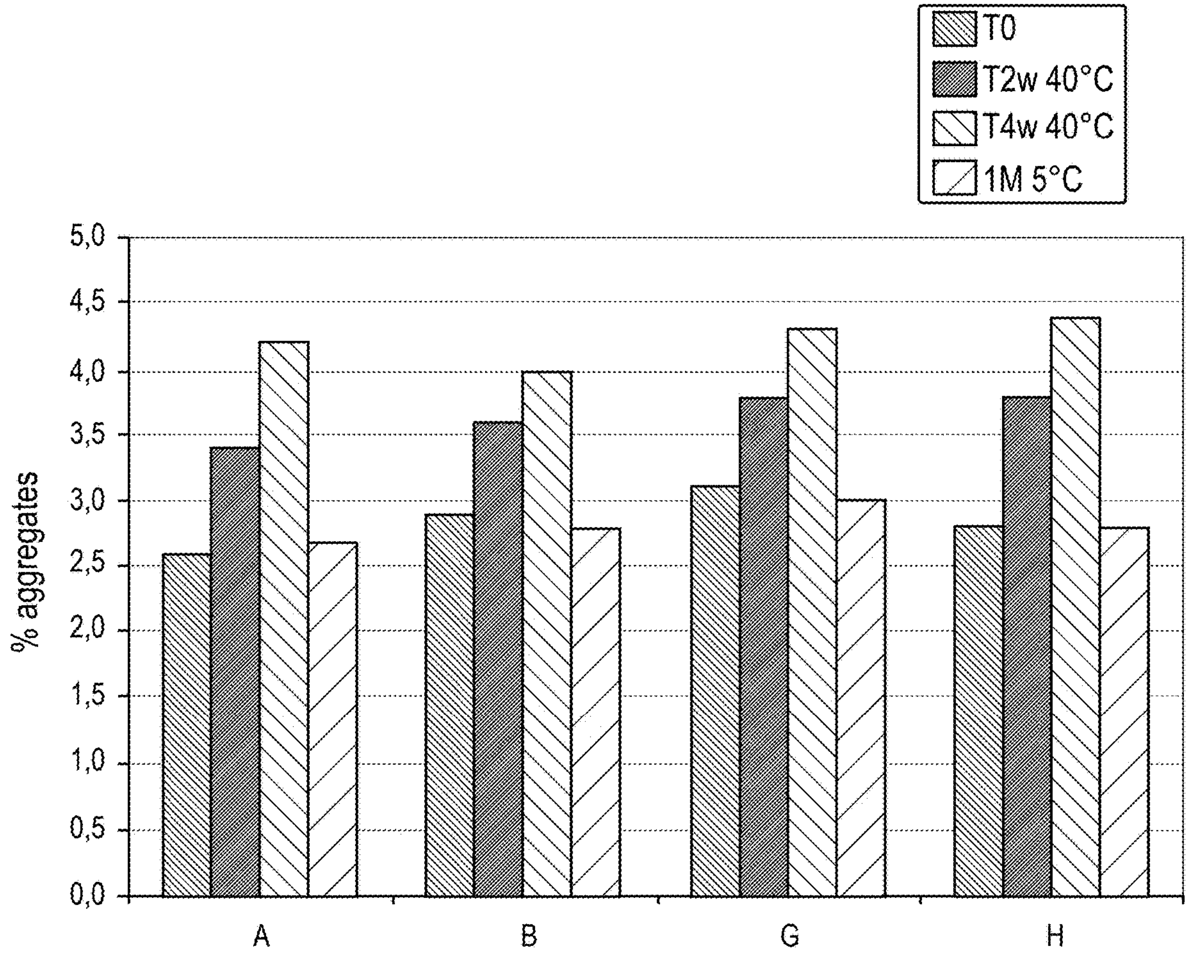
FIG. 7 is a graph depicting evolution of aggregates during indicated thermal stress. For each prototype, stress conditions appear in following order: T0, T2w40° C., T4W40° C., T1M5° C. X-axis, prototype formulation.
Figure 8:
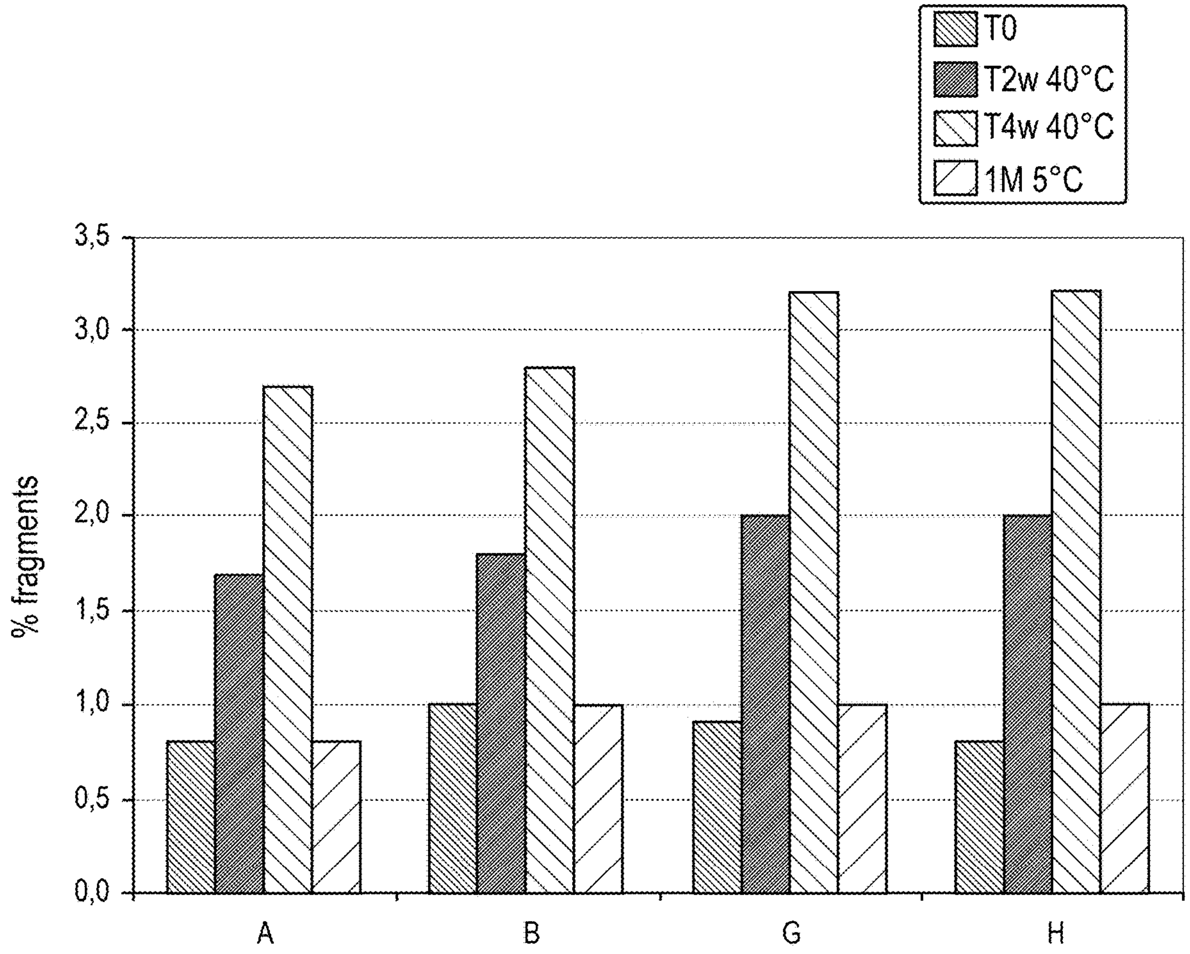
FIG. 8 is a graph depicting evolution of fragments during indicated thermal stress. For each prototype, stress conditions appear in following order: T0, T2w40° C., T4W40° C., T1M5° C. X-axis, prototype formulation.

Some differences between prototypes could be observed after 2W and 4W 40° C.:

- After 4 weeks at 40° C., the DAR decrease is the highest for formulation D (Histidine buffer at pH 6.5) and is high for formulations at pH 6.5 or in histidine (FIG. 6).
- After 2 weeks at 40° C., the highest BMW increase is observed for citrate pH 6.0 (prototype E) and is high for the 2 other formulations above pH 5.5 (D & F). Regarding prototypes at pH 5.5 in acetate buffer (A, B, G, H), an increase of aggregates (FIG. 7) and of fragments (FIG. 8) was observed after 4W40° C., higher for formulations G and H. (Prototypes C, D, E, F not analyzed at 4W40° C.).

Figure 9:
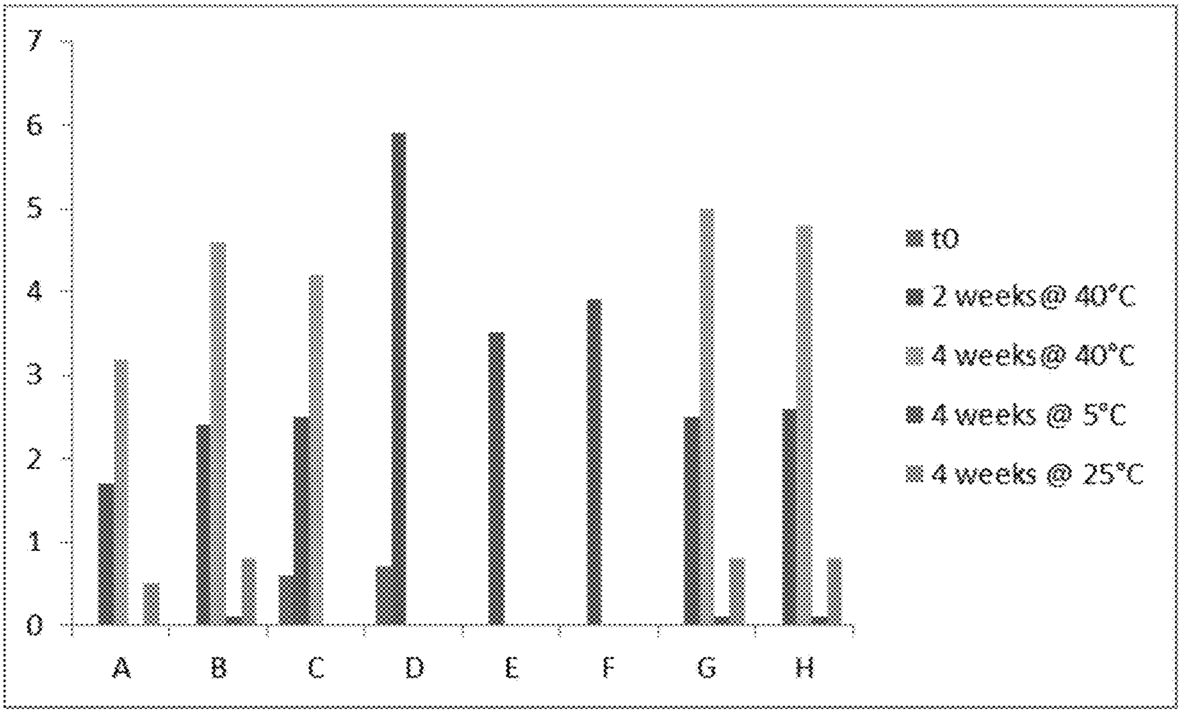
FIG. 9 is a graph depicting sum of free maytansinoids after indicated thermal stress. T0 content not visible except for Prototype D. T2W40° C. visible for all prototypes. T4W timepoint analyzed only for prototypes A, B, C, G, H. X-axis, prototype formulation; Y-axis: free maytansinoid content.
Figure 10:
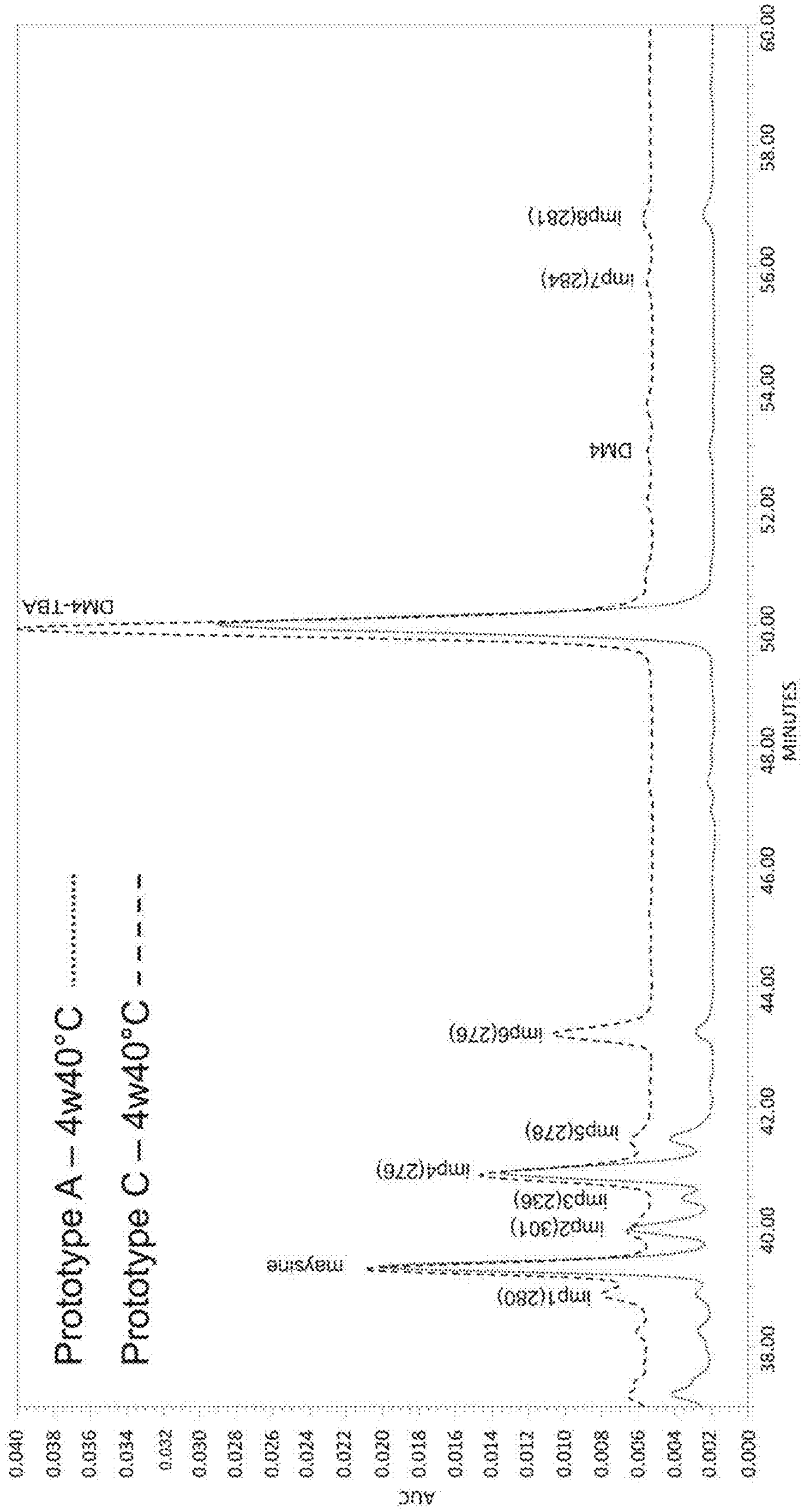
FIG. 10 is a graph depicting overlain free maytansinoid profiles after 4 weeks at 40° C. for formulations A (acetate, lower tracing) and C (histidine, upper tracing).

After 2 weeks at 40° C., regarding the free maytansinoids analysis, formulations D, E and F presented the higher levels of free maytansinoids. After 4 weeks at 40° C., only formulations at pH 5.5 were analyzed (prototypes A, B, C, G, and H) and prototype A presented the lower level of free maytansinoids (FIG. 9). The buffer type (acetate versus histidine) influenced maytansinoid detected impurities (FIG. 10).

After 4 weeks at 40° C., the highest increase of OD at 350 nm is observed for prototype D (histidine, pH 6.5) and is high for formulations at high pH or in histidine.

Figure 11:
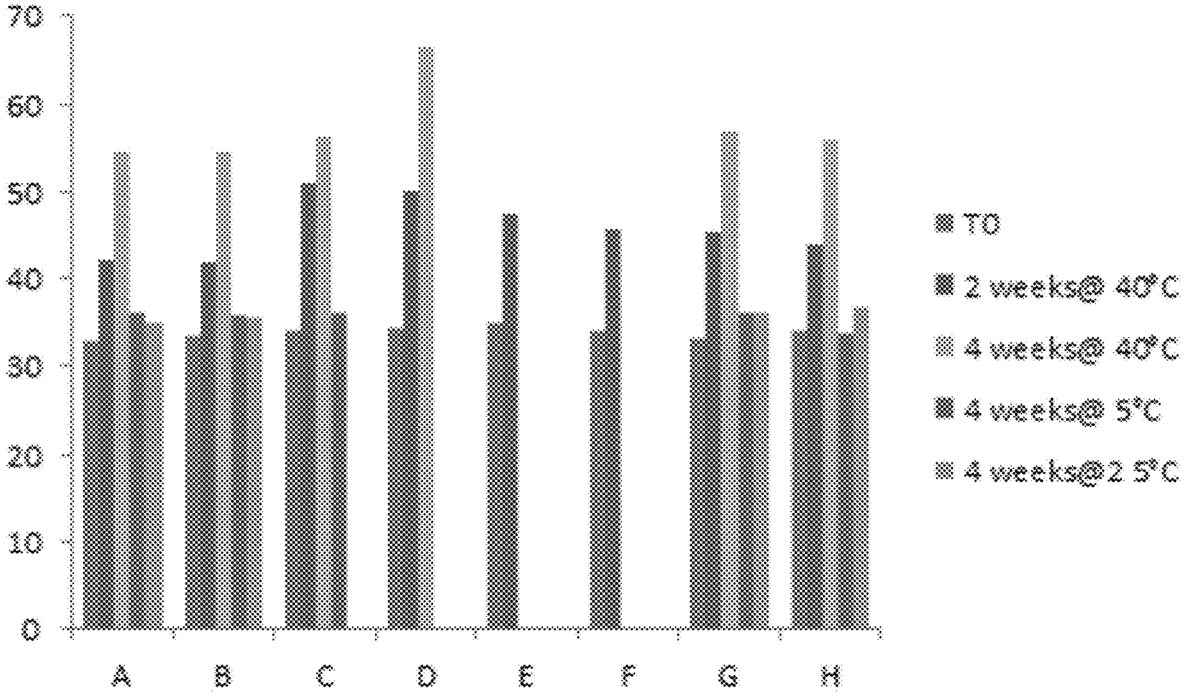
FIG. 11 is a graph depicting evolution of acidic isoforms after indicated thermal stress. For each prototype, timepoints are presented in following order: T0, T2W40° C., T4W40° C., T4W5° C., T4W25° C. Prototypes E and F not analyzed for T4W timepoint. X-axis, prototype formulation; Y axis, acidic isoforms %.
Figure 12:
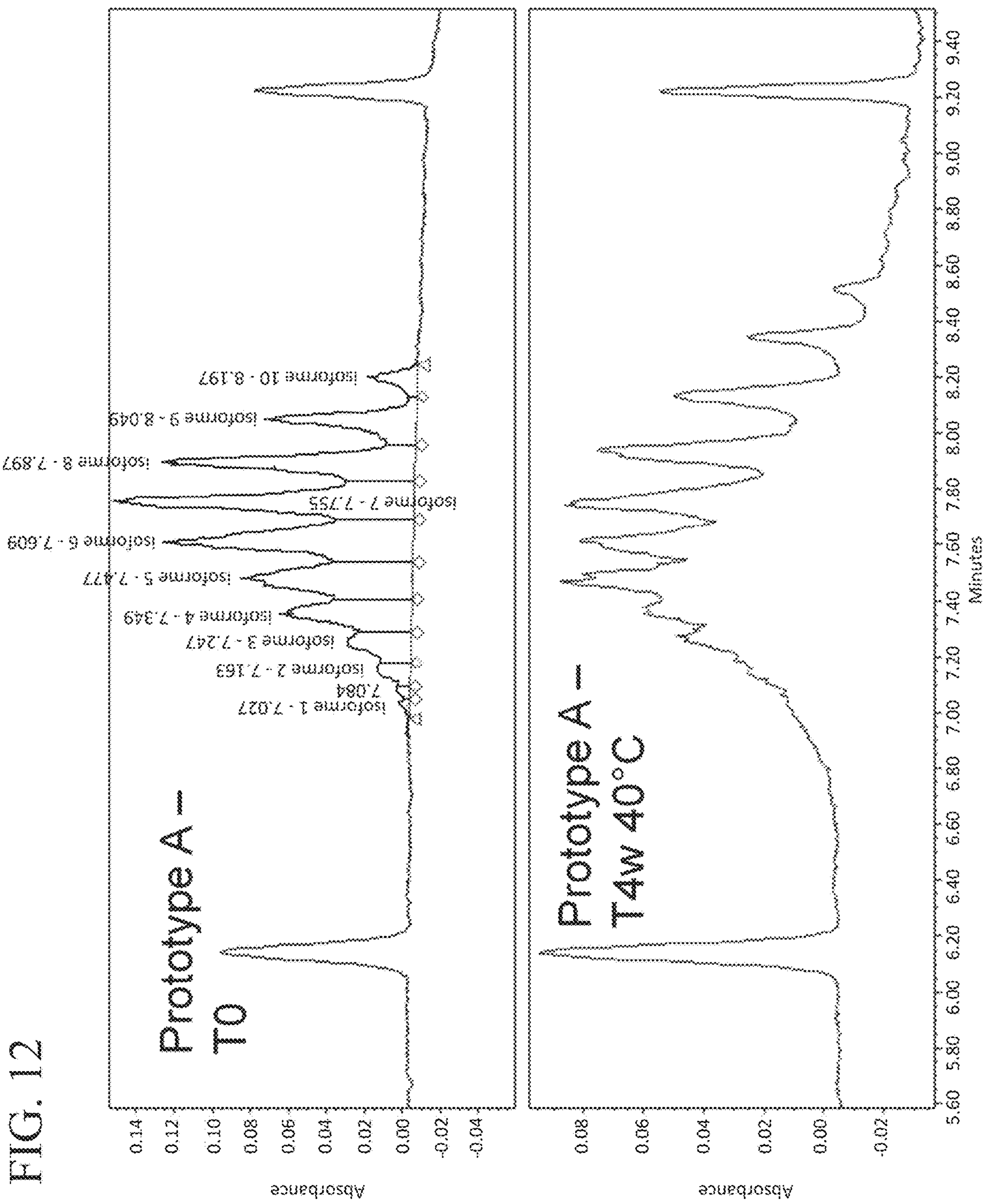
FIG. 12 is a graph depicting imaged capillary isoelectric focusing (iCIEF) chromatograms for prototype formulation A (acetate) at t0 (upper panel) and after 4 weeks at 40° C. (lower panel). X-axis, time (minutes).

Concerning results of charge isoforms by iCIEF, the highest increase of acidic species is observed for formulation D (pH 6.5) after 4W40° C. (FIG. 12). Other tested prototypes (prototypes A, B, G, and H) behaved similarly after 2W40° C. and 4W40° C. (FIG. 11).

Shaking Stress

After shaking stress, prototypes were similar for pH, concentration & DAR, DLS, turbidity, SEC-UPLC, Free maytansinoids.

Figure 13:
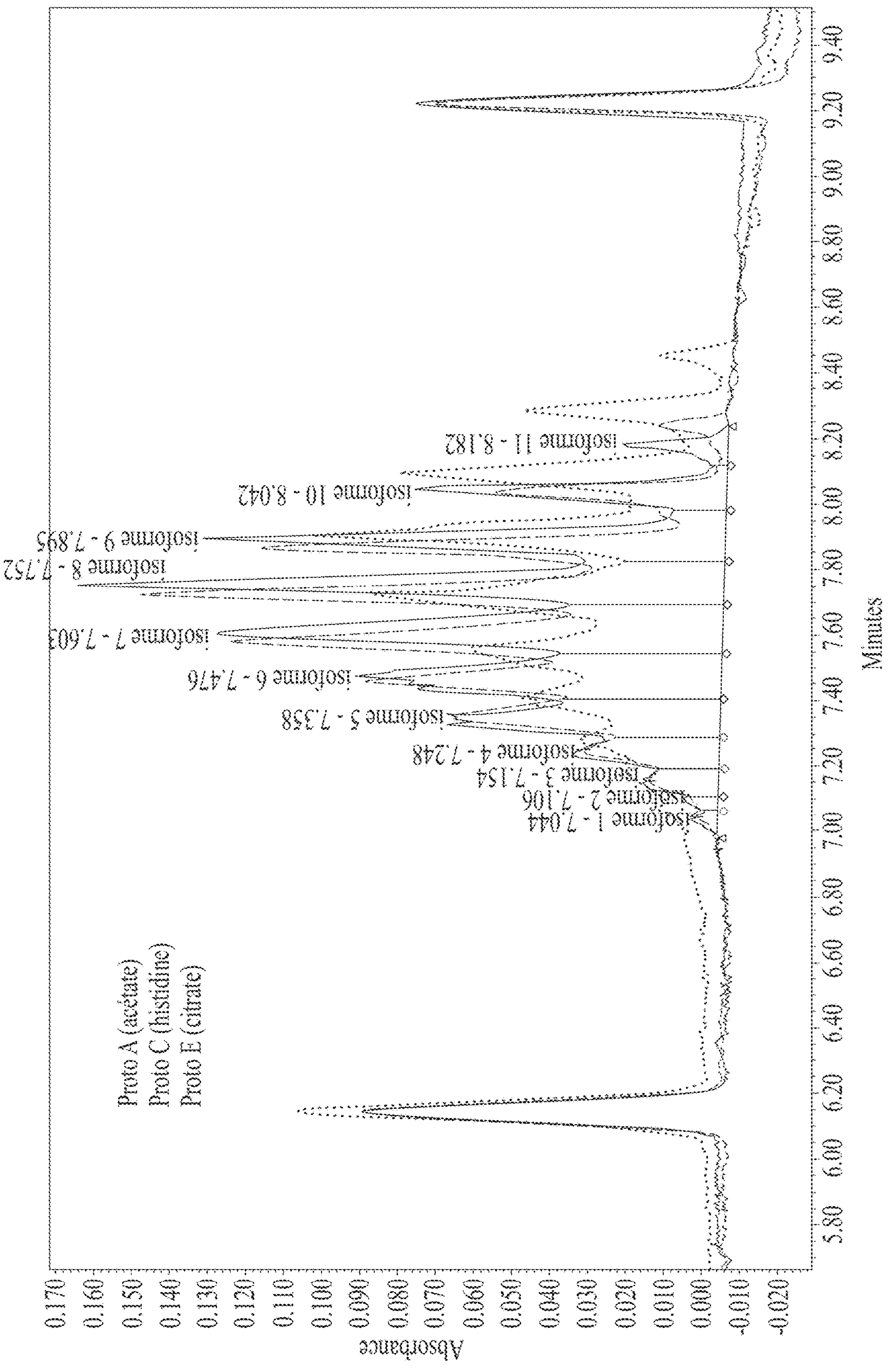
FIG. 13 is a graph depicting overlain iCIEF chromatograms after shaking stress for formulations A (acetate), C (histidine), and E (citrate).

After shaking stress, some differences between prototypes were observed:

regarding visual inspection, prototypes A and B presented no particles while prototypes D, G and H contained numerous visible particles.

regarding FCM, a slight increase of particles ≥10 and 25 μm was observed for prototype H, that could show an aggregation start with PS20 (Table 5).

regarding icIEF results, prototype C (histidine, pH 5.5) presents the highest charge variants evolution (+5% acids, −3% basics, PI shift, FIG. 13). Other prototypes depict no charge variants evolution after shaking stress.

TABLE 5

FCM results after shaking: Number of particles/mL

| Formu-lation | T0 ≥2 μm | T0 ≥10 μm | T0 ≥25 μm | Shaking ≥2 μm | Shaking ≥10 μm | Shaking ≥25 μm |
|---|---|---|---|---|---|---|
| A | 138 | 13 | 6 | 263 | 35 | 15 |
| B | 72 | 6 | 1 | 165 | 29 | 9 |
| C | 128 | 11 | 7 | 178 | 34 | 10 |
| D | 194 | 23 | 5 | 653 | 18 | 4 |
| E | 236 | 17 | 7 | 229 | 18 | 2 |
| F | 100 | 5 | 2 | 390 | 18 | 6 |
| G | 83 | 2 | 1 | 268 | 32 | 6 |
| H | 133 | 10 | 1 | 413 | 149 | 50 |

Freeze and Thaw (F/T) Stress

After F/T stress, prototypes were similar for visual inspection, pH, concentration & DAR, turbidity, SEC-UPLC, Free Maytansinoids, FCM and DLS. Regarding icIEF, prototype C is the most sensitive to F/T stress (+6% acids for −20° C. and +5% for −80° C., −6% basics for the 2 temperatures, Table 6, Table 7).

TABLE 6 iCIEF results after F/T −20° C./RT

| Formulation | Main pI | % Main Peak | Σ % Acids | Σ % Basics | No. isoforms observed |
|---|---|---|---|---|---|
| A | 7.62 | 20.5 | 34.1 | 45.4 | 11 |
| B | 7.61 | 20.6 | 33.2 | 46.3 | 11 |
| C | 7.62 | 20.2 | 40.1 | 39.1 | 11 |

TABLE 6-continued iCIEF results after F/T −20° C./RT

| Formulation | Main pI | % Main Peak | Σ % Acids | Σ % Basics | No. isoforms observed |
|---|---|---|---|---|---|
| D | 7.60 | 20.2 | 35.8 | 44.1 | 11 |
| E | 7.56 | 20.3 | 34.6 | 45.1 | 11 |
| F | 7.58 | 20.6 | 34.5 | 44.9 | 11 |
| G | 7.57* | 20.0 | 34.8 | 45.3 | 11 |
| H | 7.58 | 20.4 | 34.3 | 45.4 | 11 |

*2nd main isoform but kept for % consistency between conditions

TABLE 7 iCIEF results after F/T −80° C./RT

| Formulation | Main pI | % Main Peak | Σ % Acids | Σ % Basics | No. isoforms observed |
|---|---|---|---|---|---|
| A | 7.63 | 20.8 | 33.8 | 45.4 | 11 |
| B | 7.62 | 20.5 | 34.6 | 44.6 | 11 |
| C | 7.62 | 20.6 | 38.8 | 40.6 | 11 |
| D | 7.62 | 19.6 | 35.6 | 44.8 | 11 |
| E | 7.56 | 20.1 | 35.2 | 44.7 | 11 |
| F | 7.57 | 21.2 | 34.3 | 44.5 | 11 |
| G | 7.56 | 20.3 | 34.7 | 45.0 | 11 |
| H | 7.56* | 20.3 | 35.2 | 44.6 | 11 |

*2nd main isoform but kept for % consistency between conditions

Conclusion

The yield after UF/DF concentrated up to around 12 mg/mL was better in Acetate buffer (~92%) and the processing time was shorter than in citrate buffer. huMAb2-3-SPDB-DM4 in Citrate 10 mM pH 6.0 buffer was slightly opalescent post UF/DF.

Regarding Formulations Behavior Upon Stress:

A very slight opalescence was observed by visual inspection for all formulations but didn't evolve. By OD 350 nm, the turbidity increased after 40° C. stress for all formulations but mainly for histidine pH 6.5 (formulation D).

Some visible particles were observed only after stress of shaking for all formulations but less for formulations A and B (acetate pH 5.5 with sucrose and mannitol).

Histidine pH 6.5 was the more destabilizing for DAR after 4 weeks 40° C.

Acetate pH 5.5 was the more stabilizing for HMW (by SEC-UPLC) after 2 weeks 40° C.

After 4 weeks 40° C., LMW (by SEC-UPLC) increased by 3 for all acetate pH 5.5 formulations (not analyzed for other formulations).

For free maytansinoid and iCIEF, pH 5.5 and acetate buffer were the more stabilizing after stress (mainly thermal stress).

No aggregation in subvisible particles with PS80 was observed by FCM.

The higher Tm (by DSC) was obtained in acetate buffer (pH 5.5 and 6.0).

In conclusion, Acetate pH 5.5 appeared to be the best stabilizing buffer (mainly for DAR, HMW, free maytansinoid, charge variants) and the presence of PS80 allowed the decrease of particles.

Example 2. Selection of Sorbitol as Excipient

Methods

The formulation development study described in this example was designed based on the results of Example 1 with the following rationale:

Sodium Acetate buffer 10 mM at pH 5.5 was selected as improving several physicochemical quality attributes (mainly DAR, HMWs %, Free Maytansinoids & charge variants);

Mannitol tested in Example 1 was kept for one formulation and other polyols were tested as replacement: sucrose and sorbitol, at concentrations compatible with isotonicity; and PS80 was selected from Example 1 as improving aggregation propensity (mainly subvisible particles by FCM after shaking stress). The concentration of PS80 was varied between 0.01% w/v and 0.04% w/v.

The composition of the 6 prototypes selected for this study is given in Table 8.

TABLE 8

Prototype formulations

| Formulation ID | Buffer system | Targeted pH | Excipient | Concentration (mg/mL) |
|---|---|---|---|---|
| A | Acetate 10 mM | 5.5 | Sucrose 2.5% + Mannitol 3.75% + PS80 0.01% | 5.0 |
| B | Acetate 10 mM | 5.5 | Sucrose 10% + PS 80 0.01% | 5.0 |
| C | Acetate 10 mM | 5.5 | Sucrose 10% + PS 80 0.02% | 5.0 |
| D | Acetate 10 mM | 5.5 | Sucrose 10% + PS 80 0.04% | 5.0 |
| E | Acetate 10 mM | 5.5 | Sorbitol 5% + PS 80 0.01% | 5.0 |
| F | Acetate 10 mM | 5.5 | Sorbitol 5% + PS 80 0.04% | 5.0 |

The 6 prototype formulations were stored at 40° C. up to 1 month, at −20° C., 5° C. and 25° C. up to 3 months. They were also evaluated under stress conditions by shaking stress followed by in-use simulation. Table 9 describes the time points, stress conditions and analytical methods of the formulation study.

TABLE 9

Timepoints and analytical methods

| Timepoints | Purpose | Analytical methods |
|---|---|---|
| T0 | Initial timepoint | DSC, Visual observation, turbidity, pH, DAR and protein concentration, icIEF, Free Maytansinoids, SEC-UPLC (Monomer %, HMWs %, LMWs %), DLS, FCM, Binding by ELISA, SDS-PAGE under reduced and non-reduced conditions |
| Shaking stress (SS) | Orbital shaking, 15 hours 350 rpm | Visual observation, LO (HIAC) and FCM |
| In-use simulation (performed after SS) | Samples were diluted in NaCl 0.9% Polyolefine bags at a concentration of 0.8 mg/mL (P0 analysis). Diluted bags were kept 24 h at room temperature (P1 analysis). The diluted bags were then perfused via Hospira infusion set (Polyethylene tube and polyethersulfone 0.2 μm filter) and pumps at 1 mL/min. The collected samples (around 10 mL) were analyzed (P2 analysis). | Visual observation, LO (HIAC), DAR and protein concentration, SEC-UPLC (Monomer %, HMWs %, LMWs %) |

Drug substance used in this Example was derived from a single batch and was characterized by formulation in Acetate 10 mM, pH 5.5, 12.4 g/L. Samples were diluted in acetate buffer and supplemented with excipients to arrive at the 6 formulations shown in Table 8.

Visual inspection for appearance (clarity and particles) was performed on a visual inspection table. Vials were inspected 5 s on white surface then on black surface and the presence of visible particles was assessed. Vials were additionally inspected using an optical fiber MLC-150C from MOTIC (color temperature: 2000-3500K), with a scoring detailed in Table 10 and Table 11.

TABLE 10

Visual inspection scoring for opalescence evaluation

| | Opalescence |
|---|---|
| L | Limpid |
| SO | Slightly opalescent |
| O | Opalescent |

TABLE 11

Visual inspection scoring for particles evaluation

| Detection of particles | | Number of particles |
|---|---|---|
| 0 Not detected with cold light (optical fiber) | + | Countable (1 ≤ n ≤ 5) |
| 1 Detected only with cold light (optical fiber) | ++ | Several (n > 5) |
| 2 visible particle on visual inspection table | +++ | Numerous |

Protein Concentration and DAR (UV)

Protein Concentration and DAR measurement was performed by UV measurement, using the following method: samples were diluted by a factor 10, then the OD at 280 nm and 254 nm were measured. Below formula are used to calculate the DAR and protein concentration.

$$[\text{Drug}]\ (\text{M})=A254-(0.43\times A280)/(4.83\times 4927)-(0.43\times 4927)$$

$$[\text{Drug}]\ \text{mg/mL}=[\text{Drug}]\ (\text{M})\times 780\times F$$

$$[\text{Protein}]\ (\text{M})=A280-4927\times[\text{Drug}]\ (\text{M})/201400$$

$$[\text{Protein}]\ \text{mg/mL}=[\text{Protein}]\ (\text{M})\times 144522\times F$$

$$\text{DAR}=[\text{Drug}]\ (\text{M})/[\text{Protein}]\ (\text{M})$$

Turbidity

Turbidity was assessed by measuring the absorbance of the solution at 350 nm on 0.8 mL of non-diluted solution on a Cary UV 100 spectrometer.

Light Obscuration

Sub-visible particulate counting was performed by light obscuration technique using a high accuracy liquid particle counter (HIAC). Each result was the average of 4 measurements of 0.9 mL of sample. About 4 mL of sample was needed to perform the analysis.

Protein Purity by SDS-PAGE

Protein purity by SDS-PAGE was performed according to below procedure. Sample preparation is described in Table 12.

TABLE 12

Sample preparation for SDS PAGE

| | Reducing Conditions | Non-Reducing Conditions |
|---|---|---|
| Sample (solution or reference at 5 mg/mL) | 5 µL | 5 µL |
| Nu page LDS Buffer (×4) | 12.5 µL | +nem 12.5 µL |
| Reducing agent (×10) | 5 µL | — |
| Formulation buffer | 20 µL | 20 µL |
| Water | 7.5 µL | 12.5 µL |
| Heating | 10 minutes at 90° C. | 10 minutes at 70° C. |
| Deposit | 20 µL | 10 µL |

The sample was diluted to a concentration of 1 g/L. A reference was passed along with the samples. The 1× migration Buffer was manufactured by diluting 50 mL of buffer Nu-Page MOPS SDS Buffer 20× (Invitrogen NP0001) in sufficient quantity for 1 L purified water. The gel was a 4-12% Bis-Tris. Electrophoretic migration parameters were 135 volts for 90 minutes. Gels were then colored with a “Blue Rotiphorese” solution. Data processing was performed with Quantity one.

Results

Thermal stress study (1 month 5° C., 25° C., 40° C. and 3 months 5° C., 25° C., −20° C.).

DSC

Results of DSC at T0 are presented in Table 13.

TABLE 13

DSC results at T0

| Formulation | Td (° C.) |
|---|---|
| A—Sue 2.5% Man 3.75% PS80 0.01% | 86.4 |
| B—Sue 10% PS80 0.01% | 86.7 |
| C—Sue 10% PS80 0.02% | 86.7 |
| D—Sue 10% PS80 0.04% | 86.7 |
| E—Sorb 5% PS80 0.01% | 86.4 |
| F—Sorb 5% PS80 0.04% | 86.4 |

The thermal stability was equivalent among the 6 formulations at T0.

Visual Inspection

Results of visual inspection are provided in Table 14 (particles) and Table 15 (clarity).

TABLE 14

Visual observation results (particles)

| Visual observation | | 5° C. | | 25° C. | | 40° C. |
|---|---|---|---|---|---|---|
| Formulation | T0 | T1M | T3M | T1M | T3M | T1M |
| A—Suc 2.5% Man 3.75% PS80 0.01% | 2+ | 0 | 0 | 0 | 2+ | 0 |
| B—Suc 10% PS80 0.01% | 2+ | 0 | 0 | 1+ | 2+ | 0 |
| C—Suc 10% PS80 0.02% | 2+ | 0 | 0 | 0 | 0 | 0 |
| D—Suc 10% PS80 0.04% | 0 | 0 | 0 | 0 | 0 | 0 |
| E—Sorb 5% PS80 0.01% | 2+ | 0 | 0 | 1+ | 0 | 0 |
| F—Sorb 5% PS80 0.04% | 2+ | 0 | 0 | 0 | 0 | 0 |

TABLE 15

Visual observation results (clarity)

| Visual observation | | 5° C. | | 25° C. | | 40° C. |
|---|---|---|---|---|---|---|
| Formulation | T0 | T1M | T3M | T1M | T3M | T1M |
| A—Suc 2.5% Man 3.75% PS80 0.01% | L | SO | L | SO | L | SO |
| B—Suc 10% PS80 0.01% | L | SO | L | SO | L | SO |
| C—Suc 10% PS80 0.02% | L | SO | L | SO | L | SO |
| D—Suc 10% PS80 0.04% | L | SO | L | SO | L | SO |
| E—Sorb 5% PS80 0.01% | L | SO | L | SO | L | SO |
| F—Sorb 5% PS80 0.04% | L* | SO | L | SO | L | SO |

Overall, very few particles were observed in all formulations and for all timepoints. All formulations were limpid or slightly opalescent, without significant evolution other time.

Turbidity (OD at 350 nm)

Table 16 presents the turbidity (OD at 350 nm) results after thermal stress.

TABLE 16

Turbidity

| Turbidity | | 5° C. | | 25° C. | | 40° C. | −20° C. |
|---|---|---|---|---|---|---|---|
| Formulation | T0 | T1M | T3M | T1M | T3M | T1M | T3M |
| A—Suc 2.5% Man 3.75% PS80 0.01% | 0.0145 | 0.0153 | 0.0157 | 0.0185 | 0.0294 | 0.0631 | 0.0150 |
| B—Suc 10% PS80 0.01% | 0.0169 | 0.0177 | 0.0159 | 0.0260 | 0.0318 | 0.0698 | 0.0149 |

TABLE 16-continued

| Turbidity | | 5° C. | | 25° C. | | 40° C. | −20° C. |
|---|---|---|---|---|---|---|---|
| Formulation | T0 | T1M | T3M | T1M | T3M | T1M | T3M |
| C—Suc 10% PS80 0.02% | 0.0152 | 0.0163 | 0.0155 | 0.0214 | 0.0337 | 0.0692 | 0.0157 |
| D—Suc 10% PS80 0.04% | 0.0164 | 0.0167 | 0.0167 | 0.0221 | 0.0332 | 0.0681 | 0.0163 |
| E—Sorb 5% PS80 0.01% | 0.0140 | 0.0152 | 0.0138 | 0.0193 | 0.0277 | 0.0618 | 0.0138 |
| F—Sorb 5% PS80 0.04% | 0.0146 | 0.0152 | 0.0143 | 0.0199 | 0.0289 | 0.0599 | 0.0157 |

A significant evolution was observed after T1M40° C. for all formulations. A slight difference between E and F sorbitol-based formulations and others was noted at T1M40° C. and T3M25° C., with slightly less diffusion with sorbitol-based prototypes.

pH

The results of pH are reported in Table 17.

TABLE 17 pH results

| pH | | 5° C. | | 25° C. | | 40° C. | −20° C. |
|---|---|---|---|---|---|---|---|
| Formulation | T0 | T1M | T3M | T1M | T3M | T1M | T3M |
| A—Suc 2.5% Man 3.75% PS80 0.01% | 5.49 | 5.49 | 5.49 | 5.48 | 5.46 | 5.48 | 5.50 |
| B—Suc 10% PS80 0.01% | 5.50 | 5.48 | 5.49 | 5.49 | 5.49 | 5.48 | 5.49 |
| C—Suc 10% PS80 0.02% | 5.50 | 5.49 | 5.48 | 5.48 | 5.48 | 5.48 | 5.50 |
| D—Suc 10% PS80 0.04% | 5.51 | 5.48 | 5.50 | 5.49 | 5.48 | 5.49 | 5.49 |
| E—Sorb 5% PS80 0.01% | 5.48 | 5.49 | 5.49 | 5.49 | 5.50 | 5.49 | 5.50 |
| F—Sorb 5% PS80 0.04% | 5.48 | 5.49 | 5.50 | 5.49 | 5.52 | 5.49 | 5.50 |

No evolution of pH was observed during the stresses for all formulations.

DAR and Concentration

The results of protein concentration and DAR are reported in Table 18.

TABLE 18

Concentration and DAR results

| | | 5° C. | | 25° C. | | 40° C. | −20° C. |
|---|---|---|---|---|---|---|---|
| Formulation | T0 | T1M | T3M | T1M | T3M | T1M | T3M |
| Concentration | | | | | | | |
| A—Suc 2.5% Man 3.75% PS80 0.01% | 5.2 | 5.2 | 5.1 | 5.1 | 5.2 | 5.3 | 5.2 |
| B—Suc 10% PS80 0.01% | 5.1 | 5.1 | 5.1 | 5.1 | 5.2 | 5.2 | 5.1 |
| C—Suc 10% PS80 0.02% | 5.1 | 5.1 | 5.2 | 5.1 | 5.2 | 5.3 | 5.2 |
| D—Suc 10% PS80 0.04% | 5.1 | 5.1 | 5.2 | 5.1 | 5.2 | 5.3 | 5.2 |
| E—Sorb 5% PS80 0.01% | 5.1 | 5.1 | 5.1 | 5.1 | 5.2 | 5.2 | 5.2 |
| F—Sorb 5% PS80 0.04% | 5.2 | 5.2 | 5.2 | 5.2 | 5.2 | 5.3 | 5.2 |

TABLE 18-continued

Concentration and DAR results

| | | 5° C. | | 25° C. | | 40° C. | −20° C. |
|---|---|---|---|---|---|---|---|
| Formulation | T0 | T1M | T3M | T1M | T3M | T1M | T3M |
| DAR | | | | | | | |
| A—Suc 2.5% Man 3.75% PS80 0.01% | 3.5 | 3.5 | 3.4 | 3.8 | 3.1 | 2.5 | 3.4 |
| B—Suc 10% PS80 0.01% | 3.5 | 3.4 | 3.4 | 3.3 | 3.1 | 2.4 | 3.5 |
| C—Suc 10% PS80 0.02% | 3.5 | 3.4 | 3.5 | 3.3 | 3.2 | 2.5 | 3.5 |
| D—Suc 10% PS80 0.04% | 3.5 | 3.5 | 3.6 | 3.4 | 3.2 | 2.4 | 3.6 |
| E—Sorb 5% PS80 0.01% | 3.4 | 3.4 | 3.3 | 3.3 | 3.0 | 2.5 | 3.3 |
| F—Sorb 5% PS80 0.04% | 3.5 | 3.5 | 3.5 | 3.4 | 3.2 | 2.5 | 3.5 |

Figure 14:
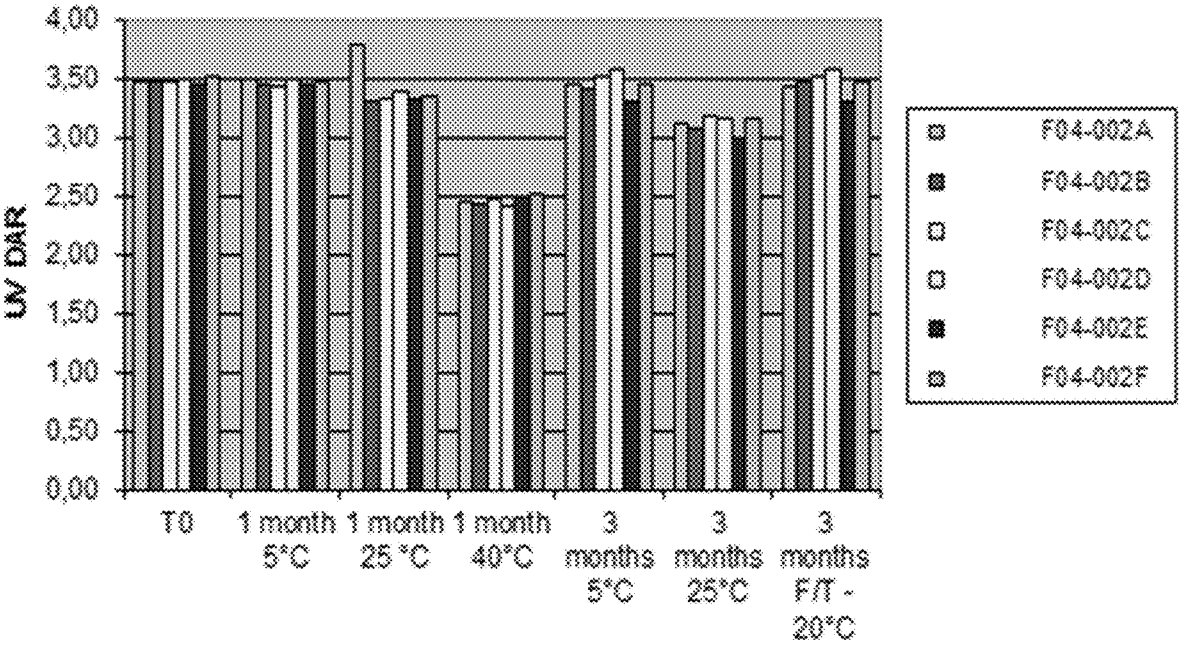
FIG. 14 is a graph depicting DAR evolution during thermal stress (initial formulation development; Example 2). For each timepoint, prototypes are presented from A to F. Y axis, DAR UV.

No evolution of concentration is observed during the stresses for all formulations. Regarding DAR, a decrease was observed upon thermal stress after T1M40° C. (approximately −1 unit) and T3M25° C. (approximately −0.5 unit) but no difference can be highlighted between prototypes (FIG. 14).

icIEF

Figure 15:
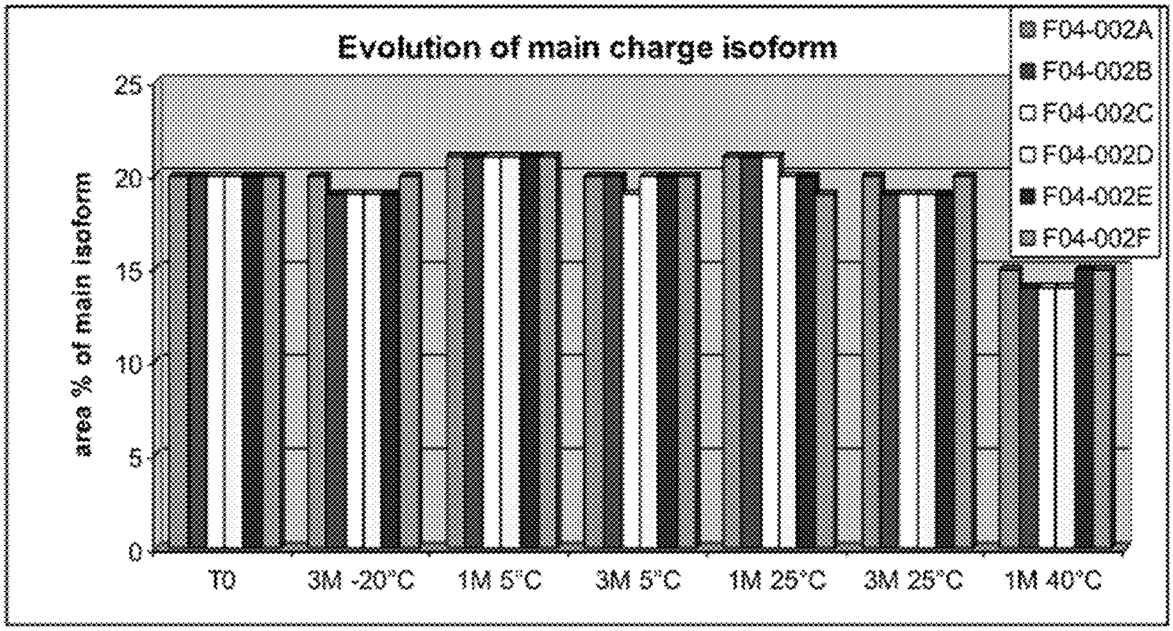
FIG. 15 is a graph depicting icIEF main charge isoforms evolution during thermal stress. For each timepoint, prototypes are presented from A to F.

The results of Main isoform %, Acidic forms % and Basic forms % are provided in Table 19. The results of main isoform content by icIEF are depicted in FIG. 15.

TABLE 19

| icIEF results | | | | | | | | |
|---|---|---|---|---|---|---|---|---|
| | | | 5° C. | | 25° C. | | 40° C. | −20° C. |
| | Formulation | T0 | T1M | T3M | T1M | T3M | T1M | T3M |
| Main Isoform % | A—Suc 2.5% Man 3.75% PS80 0.01% | 20 | 21 | 20 | 21 | 20 | 15 | 20 |
| | B—Suc 10% PS80 0.01% | 20 | 21 | 20 | 21 | 19 | 14 | 19 |
| | C—Suc 10% PS80 0.02% | 20 | 21 | 19 | 21 | 19 | 14 | 19 |
| | D—Suc 10% PS80 0.04% | 20 | 21 | 20 | 20 | 19 | 14 | 19 |
| | E—Sorb 5% PS80 0.01% | 20 | 21 | 20 | 20 | 19 | 15 | 19 |
| | F—Sorb 5% PS80 0.04% | 20 | 21 | 20 | 19 | 20 | 15 | 20 |
| Acidic isoforms % | A—Suc 2.5% Man 3.75% PS80 0.01% | 53 | 51 | 54 | 52 | 53 | 67 | 53 |
| | B—Suc 10% PS80 0.01% | 53 | 50 | 53 | 53 | 54 | 68 | 54 |
| | C—Suc 10% PS80 0.02% | 53 | 50 | 54 | 53 | 54 | 69 | 54 |
| | D—Suc 10% PS80 0.04% | 53 | 52 | 53 | 54 | 56 | 69 | 56 |
| | E—Sorb 5% PS80 0.01% | 54 | 51 | 54 | 54 | 54 | 67 | 54 |
| | F—Sorb 5% PS80 0.04% | 54 | 52 | 54 | 53 | 54 | 67 | 54 |
| Basic isoforms % | A—Suc 2.5% Man 3.75% PS80 0.01% | 27 | 28 | 27 | 27 | 27 | 18 | 27 |
| | B—Suc 10% PS80 0.01% | 27 | 29 | 27 | 27 | 27 | 18 | 27 |
| | C—Suc 10% PS80 0.02% | 27 | 29 | 27 | 26 | 27 | 18 | 27 |
| | D—Suc 10% PS80 0.04% | 27 | 28 | 28 | 26 | 24 | 17 | 24 |
| | E—Sorb 5% PS80 0.01% | 26 | 28 | 27 | 26 | 27 | 18 | 27 |
| | F—Sorb 5% PS80 0.04% | 26 | 27 | 27 | 27 | 26 | 18 | 26 |

For all formulations and all stress conditions except T1M40° C., no significant difference in the main isoform %, acidic isoforms % and basic isoforms % was observed. After T1M40° C., there was a significant decrease of main and basic isoforms %, along with an increase of acidic isoforms %. No significant difference between prototypes was seen.

Free Maytansinoids

Figure 16:
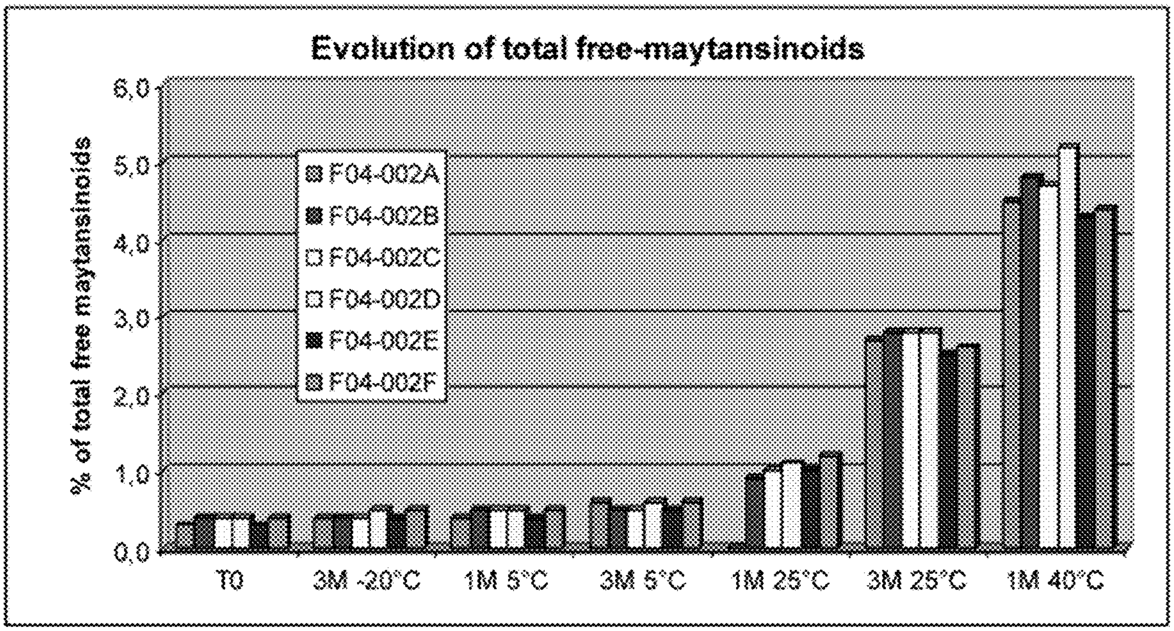
FIG. 16 is a graph depicting evolution of total free maytanisoids during thermal stress. For each timepoint, prototypes are presented from A to F.

The results of total free maytansinoids content during thermal stress are presented in FIG. 16 and in Table 20.

TABLE 20

| Free maytansinoids results | | | | | | | | |
|---|---|---|---|---|---|---|---|---|
| | | | 5° C. | | 25° C. | | 40° C. | −20° C. |
| | Formulation | T0 | T1M | T3M | T1M | T3M | T1M | T3M |
| Sum of free % | A—Suc 2.5% Man 3.75% PS80 0.01% | 0.3 | 0.4 | 0.6 | 0.8 | 2.7 | 4.5 | 0.4 |
| | B—Suc 10% PS80 0.01% | 0.4 | 0.5 | 0.5 | 0.9 | 2.8 | 4.8 | 0.4 |
| | C—Suc 10% PS80 0.02% | 0.4 | 0.5 | 0.5 | 1.0 | 2.8 | 4.7 | 0.4 |
| | D—Suc 10% PS80 0.04% | 0.4 | 0.5 | 0.6 | 1.1 | 2.8 | 5.2 | 0.5 |
| | E—Sorb 5% PS80 0.01% | 0.3 | 0.4 | 0.5 | 1.0 | 2.5 | 4.3 | 0.4 |
| | F—Sorb 5% PS80 0.04% | 0.4 | 0.5 | 0.6 | 1.2 | 2.6 | 4.4 | 0.5 |
| DM4-TBA (%) | A—Suc 2.5% Man 3.75% PS80 0.01% | 0.2 | 0.4 | 0.5 | 0.7 | 2.2 | 2.5 | 0.3 |
| | B—Suc 10% PS80 0.01% | 0.3 | 0.4 | 0.4 | 0.8 | 2.1 | 2.5 | 0.3 |
| | C—Suc 10% PS80 0.02% | 0.3 | 0.4 | 0.4 | 0.9 | 2.2 | 2.6 | 0.3 |
| | D—Suc 10% PS80 0.04% | 0.3 | 0.4 | 0.5 | 1.0 | 2.1 | 2.9 | 0.4 |
| | E—Sorb 5% PS80 0.01% | 0.2 | 0.3 | 0.4 | 0.8 | 2.0 | 2.4 | 0.3 |
| | F—Sorb 5% PS80 0.04% | 0.3 | 0.4 | 0.5 | 1.0 | 2.1 | 2.7 | 0.4 |
| DM4-(%) | A—Suc 2.5% Man 3.75% PS80 0.01% | 0.1 | 0.1 | 0.1 | — | — | — | 0.1 |
| | B—Suc 10% PS80 0.01% | 0.1 | 0.1 | 0.1 | — | — | — | 0.1 |
| | C—Suc 10% PS80 0.02% | 0.1 | 0.1 | 0.1 | — | — | — | 0.1 |
| | D—Suc 10% PS80 0.04% | 0.1 | 0.1 | 0.1 | 0.1 | — | — | 0.1 |
| | E—Sorb 5% PS80 0.01% | 0.1 | 0.1 | 0.1 | 0.1 | — | — | 0.1 |
| | F—Sorb 5% PS80 0.04% | 0.1 | 0.1 | 0.1 | 0.1 | — | — | 0.1 |

The free maytansinoids content of all formulations increased after T1M25° C. (slightly), T3m25° C. and T1M40° C. Equivalent levels were observed for all prototypes in each condition. Formulations E and F presented a slightly lower content of free maytansinoids after T3M25° C. and T1M40° C. Formulation D had a slightly higher free maytansinoids content after T1M40° C.

Overall, sorbitol-containing prototypes (formulations E and F) were better regarding total free maytansinoids content as seen at T1M40° C. and T3M25° C.

SEC-UPLC

Results of SEC-UPLC are depicted in Table 21.

TABLE 21

Monomer %, HMWs % and LMWs % under thermal stress by SEC-UPLC

| | Formulation | T0 | 5° C. T1M | 5° C. T3M | 25° C. T1M | 25° C. T3M | 40° C. T1M | −20° C. T3M |
|---|---|---|---|---|---|---|---|---|
| Monomer % | A—Suc 2.5% Man 3.75% PS80 0.01% | 98.3 | 98.3 | 98.2 | 98.1 | 96.3 | 93.7 | 98.3 |
| | B—Suc 10% PS80 0.01% | 98.3 | 98.3 | 98.2 | 98.1 | 96.2 | 93.7 | 98.4 |
| | C—Suc 10% PS80 0.02% | 98.3 | 98.3 | 98.2 | 98.1 | 96.2 | 93.5 | 98.4 |
| | D—Suc 10% PS80 0.04% | 98.3 | 98.3 | 98.2 | 98.1 | 96.1 | 93.5 | 98.3 |
| | E—Sorb 5% PS80 0.01% | 98.3 | 98.3 | 98.2 | 98.1 | 96.5 | 94.0 | 98.3 |
| | F—Sorb 5% PS80 0.04% | 98.3 | 98.3 | 98.2 | 98.1 | 96.4 | 93.9 | 98.3 |
| HMWs % | A—Suc 2.5% Man 3.75% PS80 0.01% | 1.7 | 1.7 | 1.7 | 1.8 | 2.1 | 3.2 | 1.7 |
| | B—Suc 10% PS80 0.01% | 1.7 | 1.7 | 1.7 | 1.8 | 2.0 | 3.1 | 1.6 |
| | C—Suc 10% PS80 0.02% | 1.7 | 1.7 | 1.7 | 1.8 | 2.0 | 3.1 | 1.6 |
| | D—Suc 10% PS80 0.04% | 1.7 | 1.7 | 1.7 | 1.8 | 2.0 | 3.1 | 1.6 |
| | E—Sorb 5% PS80 0.01% | 1.7 | 1.7 | 1.7 | 1.8 | 2.0 | 3.3 | 1.7 |
| | F—Sorb 5% PS80 0.04% | 1.7 | 1.7 | 1.7 | 1.8 | 2.0 | 3.2 | 1.7 |
| LMWs % | A—Suc 2.5% Man 3.75% PS80 0.01% | 0.1 | 0.1 | 0.1 | 0.1 | 1.7 | 3.1 | <0.1 |
| | B—Suc 10% PS80 0.01% | 0.1 | 0.1 | 0.1 | 0.1 | 1.8 | 3.3 | <0.1 |
| | C—Suc 10% PS80 0.02% | 0.1 | 0.1 | 0.1 | 0.1 | 1.8 | 3.4 | <0.1 |
| | D—Suc 10% PS80 0.04% | 0.1 | 0.1 | 0.1 | 0.1 | 1.8 | 3.4 | <0.1 |
| | E—Sorb 5% PS80 0.01% | 0.1 | 0.1 | 0.1 | 0.1 | 1.4 | 2.8 | <0.1 |
| | F—Sorb 5% PS80 0.04% | 0.1 | 0.1 | <0.1 | 0.1 | 1.5 | 2.8 | <0.1 |

For all formulations and all thermal stress conditions, MONOMER % and HMWS % evolved in a similar manner.

Figure 17:
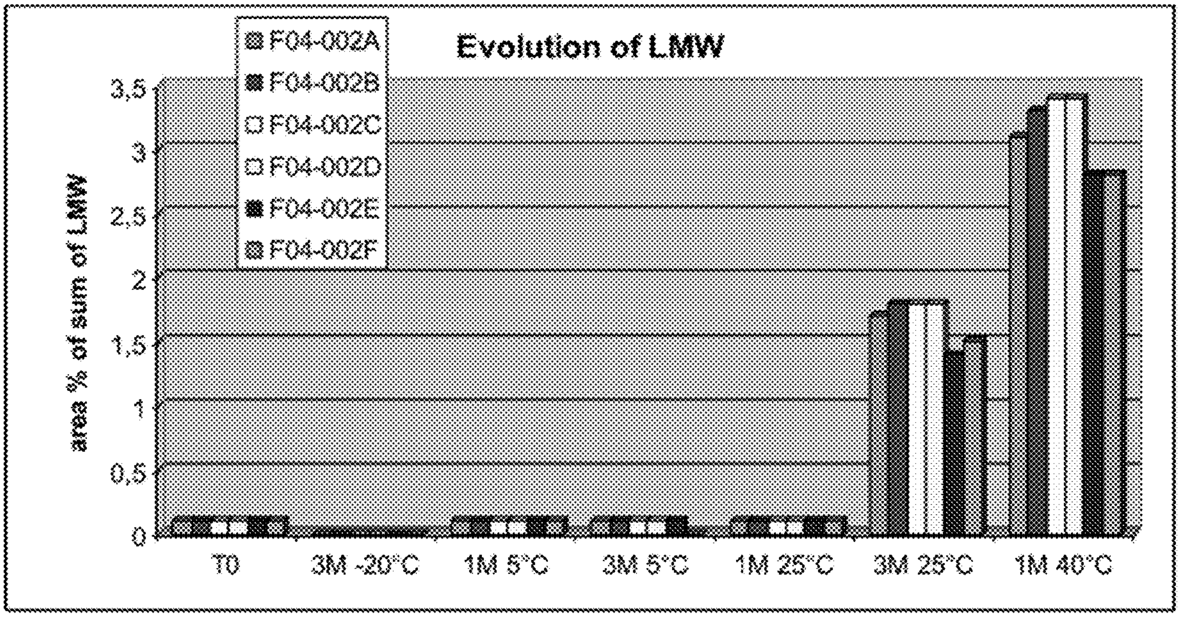
FIG. 17 is a graph depicting evolution of LMW during thermal stress. For each timepoint, prototypes are presented from A to F.

Regarding LMWS %, similar levels of fragments were observed at T0, T1M and T3M 5° C., T3M −20° C. and T1M25° C. for all formulations. After T3M25° C. and T1M40° C., formulations E and F seemed to have lower LMWS % than other formulations (−0.3% to −0.6% after T1M40° C. compared to other formulations), as depicted in FIG. 17.

SDS Page

Observations in non-reduced conditions were as follows: after T3M5° C. and T3M25° C., same pattern as T0 and no difference between formulations was observed. After T1m40° C., an additional band appeared at 46 kDa for all formulations. Its relative quantity was 0.1% to 0.6%.

Observations in reduced conditions were as follows: after T3m5° C. and T3m25° C., same pattern and no significant difference between formulations was observed. After T1m40° C., up to 9 additional bands appeared at 33, 42, 44, 83, 87, 90, 130, 150 and 160 kDa depending on the formulation. No significant difference was observed between formulations.

Overall, no difference between formulations can be highlighted by SDS-PAGE for all tested thermal stress conditions.

FCM

FCM results are presented in Table 22.

TABLE 22

FCM results during thermal stress

| Particles/mL | Formulation | T0 | 5° C. T1M | 5° C. T3M | 25° C. T1M | 25° C. T3M | 40° C. T1M | −20° C. T3M |
|---|---|---|---|---|---|---|---|---|
| ≥2 μm | A—Suc 2.5% Man 3.75% PS80 0.01% | 436 | 192 | 710 | 129 | 362 | 384 | 336 |
| | B—Suc 10% PS80 0.01% | 446 | 126 | 642 | 192 | 525 | 321 | 131 |
| | C—Suc 10% PS80 0.02% | 211 | 371 | 491 | 144 | 495 | 1806 | 374 |
| | D—Suc 10% PS80 0.04% | 105 | 208 | 287 | 168 | 1098 | 162 | 137 |
| | E—Sorb 5% PS80 0.01% | 158 | 284 | 422 | 194 | 326 | 210 | 168 |
| | F—Sorb 5% PS80 0.04% | 161 | 180 | 511 | 698 | 346 | 508 | 108 |
| ≥10 μm | A—Suc 2.5% Man 3.75% PS80 0.01% | 40 | 15 | 15 | 10 | 10 | 20 | 13 |
| | B—Suc 10% PS80 0.01% | 35 | 10 | 28 | 9 | 12 | 23 | 12 |
| | C—Suc 10% PS80 0.02% | 15 | 16 | 13 | 10 | 13 | 54 | 33 |
| | D—Suc 10% PS80 0.04% | 6 | 16 | 11 | 15 | 16 | 11 | 11 |
| | E—Sorb 5% PS80 0.01% | 7 | 21 | 11 | 13 | 14 | 10 | 13 |
| | F—Sorb 5% PS80 0.04% | 8 | 14 | 11 | 63 | 15 | 16 | 13 |
| ≥25 μm | A—Suc 2.5% Man 3.75% PS80 0.01% | 4 | 3 | 1 | 1 | 1 | 3 | 2 |
| | B—Suc 10% PS80 0.01% | 1 | 1 | 5 | 1 | 2 | 4 | 1 |
| | C—Suc 10% PS80 0.02% | 2 | 1 | 2 | 2 | 2 | 5 | 2 |
| | D—Suc 10% PS80 0.04% | 1 | 1 | 1 | 4 | 1 | 1 | 1 |
| | E—Sorb 5% PS80 0.01% | 1 | 1 | 1 | 2 | 4 | 2 | 1 |
| | F—Sorb 5% PS80 0.04% | 1 | 3 | 0 | 4 | 6 | 0 | 1 |

For all prototypes and all thermal stress conditions, there was no significant evolution of the sub-visible particles by FCM.

Binding to CEACAM5 by ELISA

Binding to CEACAM5 by ELISA results are presented in Table 23. Formulations were tested against the T0 samples after T3M −20° C., T3M5° C., and T3M25° C. (relative potencies $EC_{50}$ T0/$EC_{50}$ T3m).

TABLE 23

| Binding by ELISA after T3M5° C., T3M25° C. and T3M −20° C. | | | |
|---|---|---|---|
| Formulation | T3M5° C. | T3M25° C. | T3M−20° C. |
| A—Suc 2.5% Man 3.75% PS80 0.01% | 96 | 98 | 104 |
| B—Suc 10% PS80 0.01% | 101 | 93 | 102 |
| C—Suc 10% PS80 0.02% | 99 | 98 | 98 |
| D—Suc 10% PS80 0.04% | 100 | 95 | 97 |
| E—Sorb 5% PS80 0.01% | 102 | 94 | 94 |
| F—Sorb 5% PS80 0.04% | 99 | 100 | 92 |

The relative potency of the binding to CEACAM5 by ELISA was stable after T3M −20° C., T3M5° C., and T3M25° C. Under these experimental conditions, no difference was noted between formulation prototypes.

Shaking Stress

Table 24 presents results of visual observation after shaking stress.

TABLE 24

| Visual observation after shaking stress (particles) | | |
|---|---|---|
| Formulation | T0 | Shaking stress |
| A—Suc 2.5% Man 3.75% PS80 0.01% | 2+ | 2+ |
| B—Suc 10% PS80 0.01% | 2+ | 2+ |
| C—Suc 10% PS80 0.02% | 2+ | 2+ |
| D—Suc 10% PS80 0.04% | 0 | 2++ |
| E—Sorb 5% PS80 0.01% | 2+ | 2+ |
| F—Sorb 5% PS80 0.04% | 2+ | 2++ |

Few particles were observed for all formulations after shaking stress. Particles were most often identified as exogenous fibers.

LO (HIAC) and FCM

Table 25 and Table 26 present subvisible particles results by HIAC and FCM after shaking stress.

TABLE 25

| HIAC results after shaking stress | | | | | | |
|---|---|---|---|---|---|---|
| Particles/mL | T0 | | | After shaking stress | | |
| Formulations | ≥1.5 μm | ≥10 μm | ≥25 μm | ≥1.5 μm | ≥10 μm | ≥25 μm |
| A—Suc 2.5% Man 3.75% PS80 0.01% | 352 | 22 | 5 | 485 | 11 | 1 |
| B—Suc 10% PS80 0.01% | 114 | 10 | 4 | 222 | 13 | 2 |
| C—Suc 10% PS80 0.02% | 208 | 17 | 1 | 257 | 12 | 2 |
| D—Suc 10% PS80 0.04% | 198 | 24 | 5 | 155 | 13 | 1 |
| E—Sorb 5% PS80 0.01% | 277 | 19 | 3 | 105 | 7 | 1 |
| F—Sorb 5% PS80 0.04% | 241 | 34 | 2 | 124 | 6 | 2 |

TABLE 26

| FCM results after shaking | | | | | | |
|---|---|---|---|---|---|---|
| Particles/mL | T0 | | | After shaking stress | | |
| Prototypes | ≥2 μm | ≥10 μm | ≥25 μm | ≥2 μm | ≥10 μm | ≥25 μm |
| A—Suc 2.5% Man 3.75% PS80 0.01% | 436 | 40 | 4 | 1337 | 59 | 5 |
| B—Suc 10% PS80 0.01% | 446 | 35 | 1 | 1165 | 59 | 5 |
| C—Suc 10% PS80 0.02% | 211 | 15 | 2 | 759 | 102 | 12 |
| D—Suc 10% PS80 0.04% | 105 | 6 | 1 | 412 | 25 | 3 |
| E—Sorb 5% PS80 0.01% | 158 | 7 | 1 | 225 | 12 | 1 |
| F—Sorb 5% PS80 0.04% | 161 | 8 | 1 | 798 | 33 | 3 |

A slight increase of ≥10 µM particles was seen for formulation C by FCM, but not by HIAC. overall, the stability of all formulations with regards to sub-visible particles after shaking stress was satisfactory.

In-Use Simulation

Visual Observation

Three sampling points are assessed:

P0: T0 after dilution at 0.8 g/L in NaCl 0.9%

P1: T24 h at RT after dilution at 0.8 g/L in NaCl 0.9%, without infusion through infusion line and filter P2: T24 h at RT after dilution at 0.8 g/L in NaCl 0.9%, after infusion through infusion line and filter.

All formulations presented visible particles after dilution in NaCl 0.9%:

At P0 sampling point, following ranking was proposed: F<(better than) D<C<B<E<A, with a being the worst case and f significantly better than other formulations.

At P1 sampling point, following ranking was proposed: F<D<C<E<B<A (less difference between samples that at P0)

At P2 sampling point, there are much less particles in all formulations except prototype E. Prototype E presented numerous particles; other prototypes were similar, with few particles.

To conclude, the dilution in NaCl 0.9% increased the level of visible particles in all formulations. After infusion (P2 sample), the level of particles returned to levels comparable to T0 levels, except for formulation E with 100 ppm ps80.

Sub-Visible Particles

Table 27 and Table 28 depict the results of sub-visible particles by HIAC after in-use simulation, respectively in particles/ml and particles/container.

TABLE 27

HIAC results after in-use simulation

| Particles/mL | T0 | | | P0 | | | P1 | | | P2 | | |
|---|---|---|---|---|---|---|---|---|---|---|---|---|
| Formulations | ≥1.5 µm | ≥10 µm | ≥25 µm | ≥1.5 µm | ≥10 µm | ≥25 µm | ≥1.5 µm | ≥10 µm | ≥25 µm | ≥1.5 µm | ≥10 µm | ≥25 µm |
| A—Suc 2.5% Man 3.75% PS80 0.01% | 352 | 22 | 5 | 5836 | 245 | 5 | 4782 | 207 | 11 | 160 | 19 | 3 |
| B—Suc 10% PS80 0.01% | 114 | 10 | 4 | 4072 | 86 | 2 | 1735 | 52 | 2 | 120 | 8 | 0 |
| C—Suc 10% PS80 0.02% | 208 | 17 | 1 | 2733 | 37 | 2 | 1445 | 25 | 1 | 59 | 6 | 1 |
| D—Suc 10% PS80 0.04% | 198 | 24 | 5 | 1992 | 18 | 1 | 889 | 45 | 3 | 37 | 7 | 1 |
| E—Sorb 5% PS80 0.01% | 277 | 19 | 3 | 2676 | 110 | 4 | 935 | 43 | 1 | 260 | 37 | 3 |
| F—Sorb 5% PS80 0.04% | 241 | 34 | 2 | 881 | 8 | 0 | 1430 | 32 | 2 | 62 | 4 | 1 |

TABLE 28

HIAC results after in-use simulation, expressed in particles per container (50 mL bag)

| Particles per container | | T0 | | P0 | | P1 | | P2 | |
|---|---|---|---|---|---|---|---|---|---|
| Formulations | Specifications | ≥10 µm | ≥25 µm | ≥10 µm | ≥25 µm | ≥10 µm | ≥25 µm | ≥10 µm | ≥25 µm |
| A—Suc 2.5% Man 3.75% PS80 0.01% | Before infusion, for information only. | 1100 | 250 | 12250 | 250 | 10350 | 550 | 950 | 150 |
| B—Suc 10% PS80 0.01% | After infusion: Number of | 500 | 200 | 4300 | 100 | 2600 | 100 | 400 | 0 |
| C—Suc 10% PS80 0.02% | particles ≥10 µm ≤6000/recipient | 850 | 50 | 1850 | 100 | 1250 | 50 | 300 | 50 |
| D—Suc 10% PS80 0.04% | Number of particles ≥25 µm | 1200 | 250 | 900 | 50 | 2250 | 150 | 350 | 50 |
| E—Sorb 5% PS80 0.01% | ≤600/recipient | 950 | 150 | 5500 | 200 | 2150 | 50 | 1850 | 150 |
| F—Sorb 5% PS80 0.04% | | 1700 | 100 | 400 | 0 | 1600 | 100 | 200 | 50 |

Figure 18:
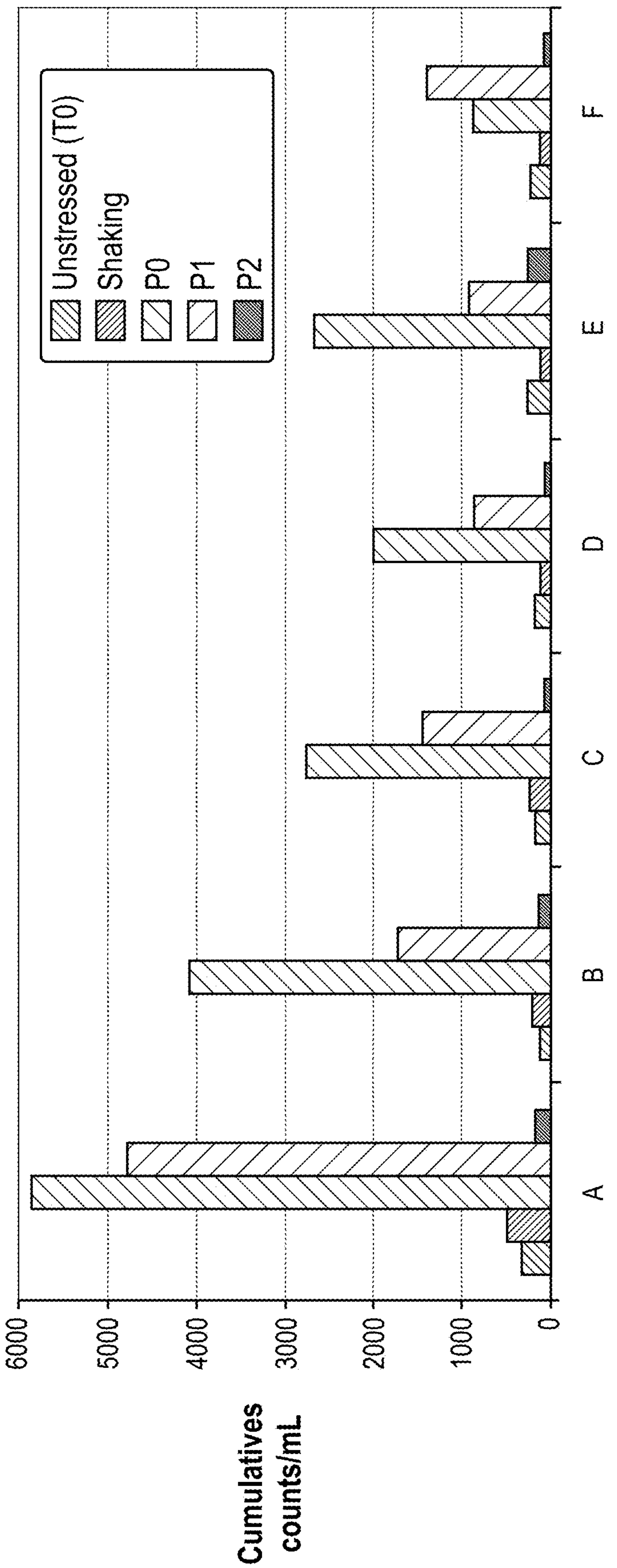
FIG. 18 is a graph depicting high accuracy liquid particle counter (HIAC) results after in-use simulation, particles ≥1.5 μm. For each prototype, stresses are represented in the following order: unstressed (T0), after shaking stress, P0 (after dilution in NaCl 0.9% IV bag at 0.9 g/L), P1 (24 h after dilution in NaCl 0.9% IV bag at 0.9 g/L) and P2 (24 h after dilution in NaCl 0.9% IV bag at 0.9 g/L and perfusion through an IV infusion set with in-line filter).

Osmotic stress by dilution in saline solution (NaCl 0.9%) generated ≥1.5 μm sub-visible particles in all formulations as seen in FIG. 18 on P0 and P1 sampling points. Formulation A had a significantly higher number of ≥1.5 μm particles. Formulations A and E had a significantly higher number of ≥10 μm particles on P0 sampling point. Both A and E formulations had the lower tested PS80 concentration of 100 ppm.

After infusion through the infusion line and 0.2 μm filter (P2 sampling point), sub-visible particles were reduced for all formulations. All formulations passed the pharmacopeia criteria for 50 mL infusion bags. Formulation E would not pass pharmacopeial criteria for volumes above 100 mL (below 25 particles/mL≥10 μm and below 3 particles/mL≥25 μm). A higher risk of non-compliance was highlighted for 100 ppm PS80 concentration.

Concentration & DAR

Figure 19A:
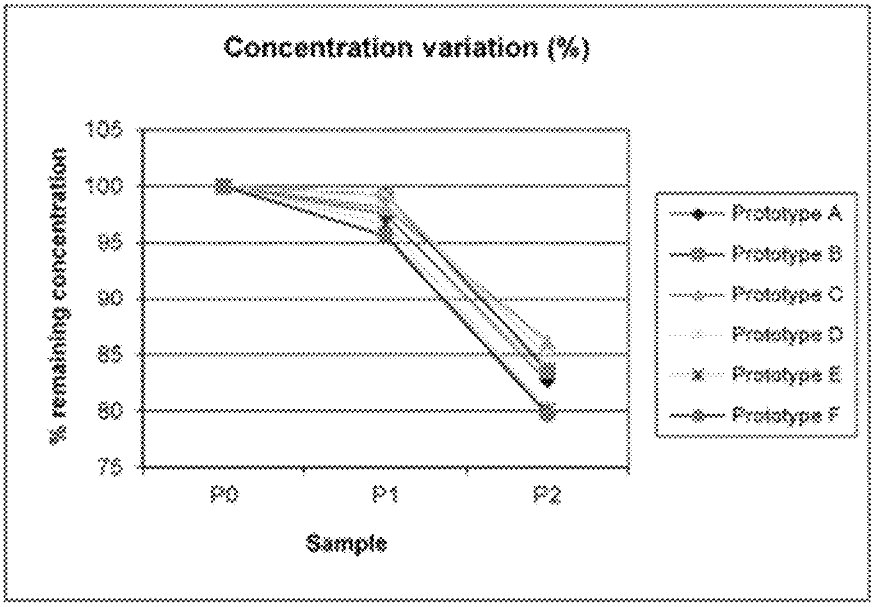
FIG. 19A is a graph depicting concentration variation % after in-use simulation.
Figure 19B:
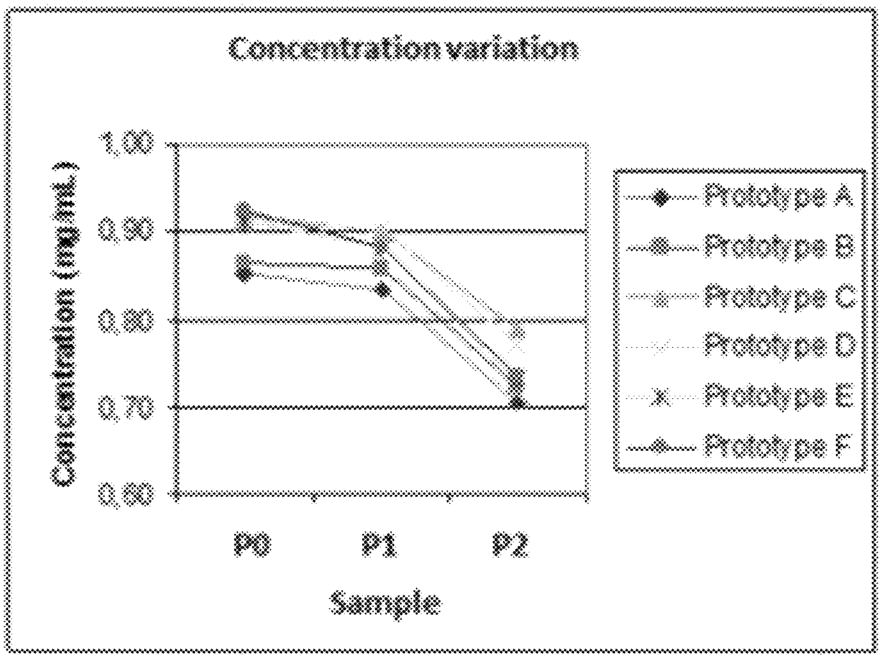
FIG. 19B is a graph depicting concentration variation after in-use simulation.
Figure 20A:
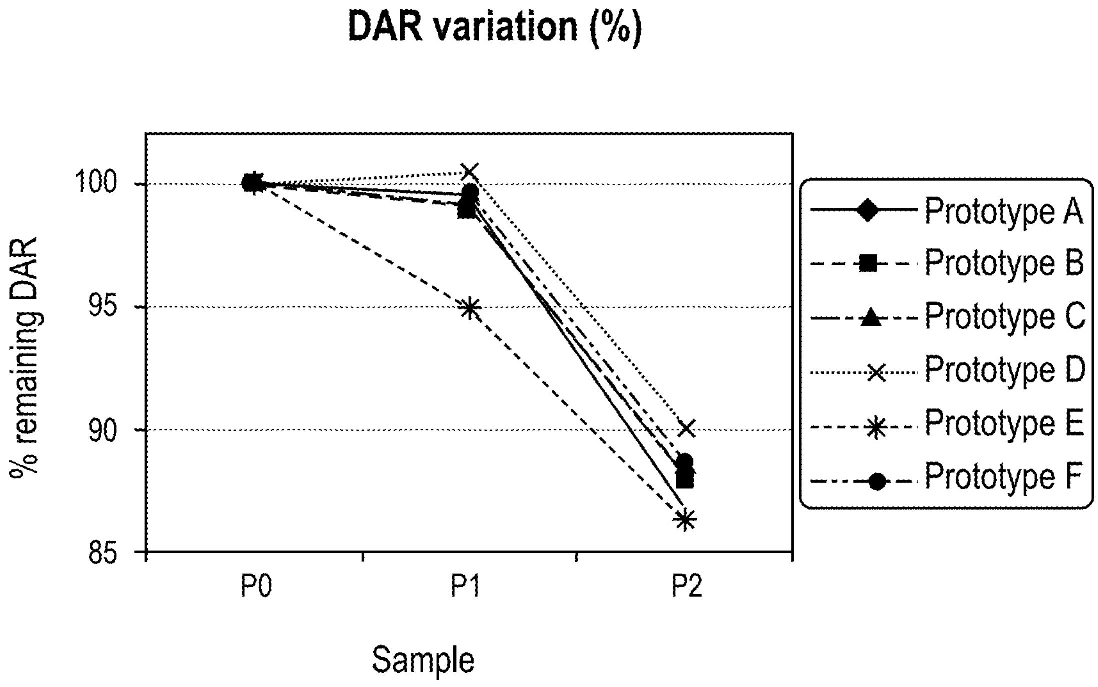
FIG. 20A is a graph depicting DAR variation (%) after in-use simulation.
Figure 20B:
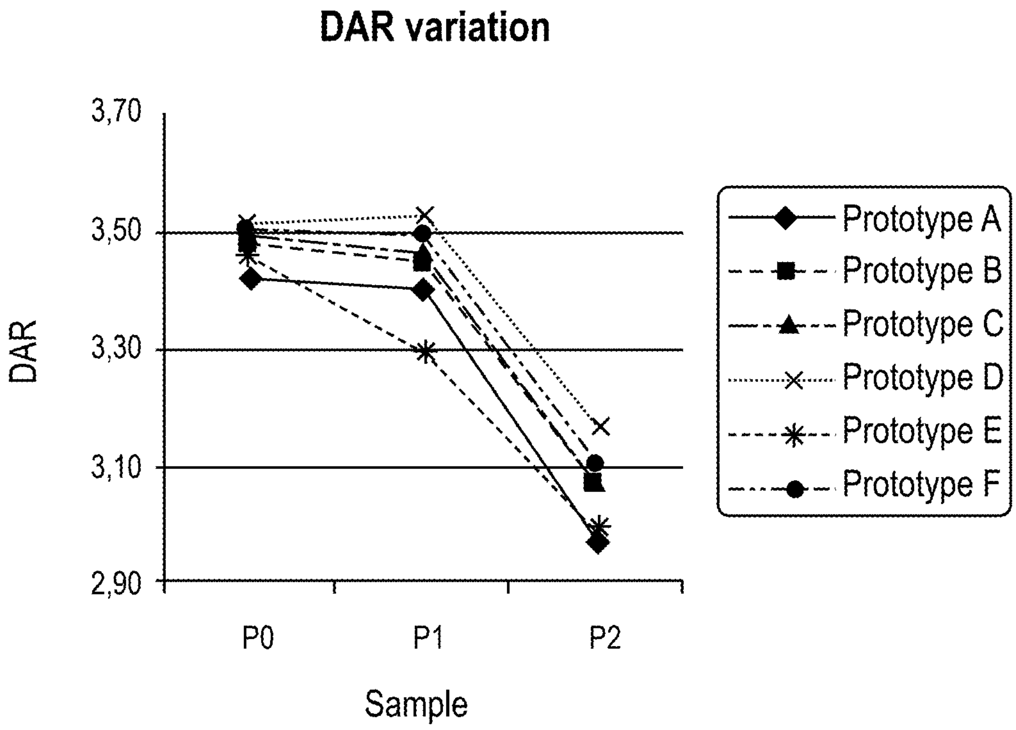
FIG. 20B is a graph depicting DAR variation (%) after in-use simulation.

FIG. 19 and FIG. 20 depict the results of protein concentration and DAR after in-use simulation. for all formulations, a decrease of concentration (−15 to −20%) and of DAR (−10 to −15%) was observed after in-use simulation of around 10 ml with usual infusion kit (0.2 μM pes in-line filter included). no difference could be highlighted between prototypes.

SEC-UPLC

Figure 21:
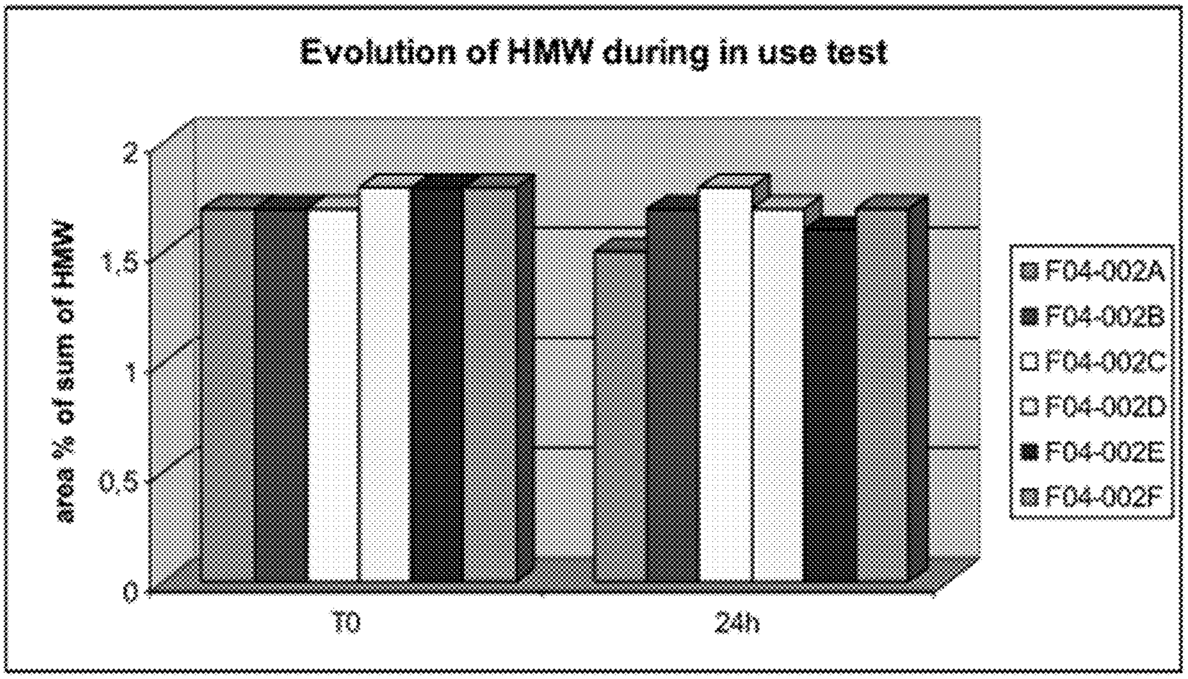
FIG. 21 is a graph depicting evolution of HMW during in-use simulation. For both timepoints, prototypes are represented from A to F.
Figure 22:
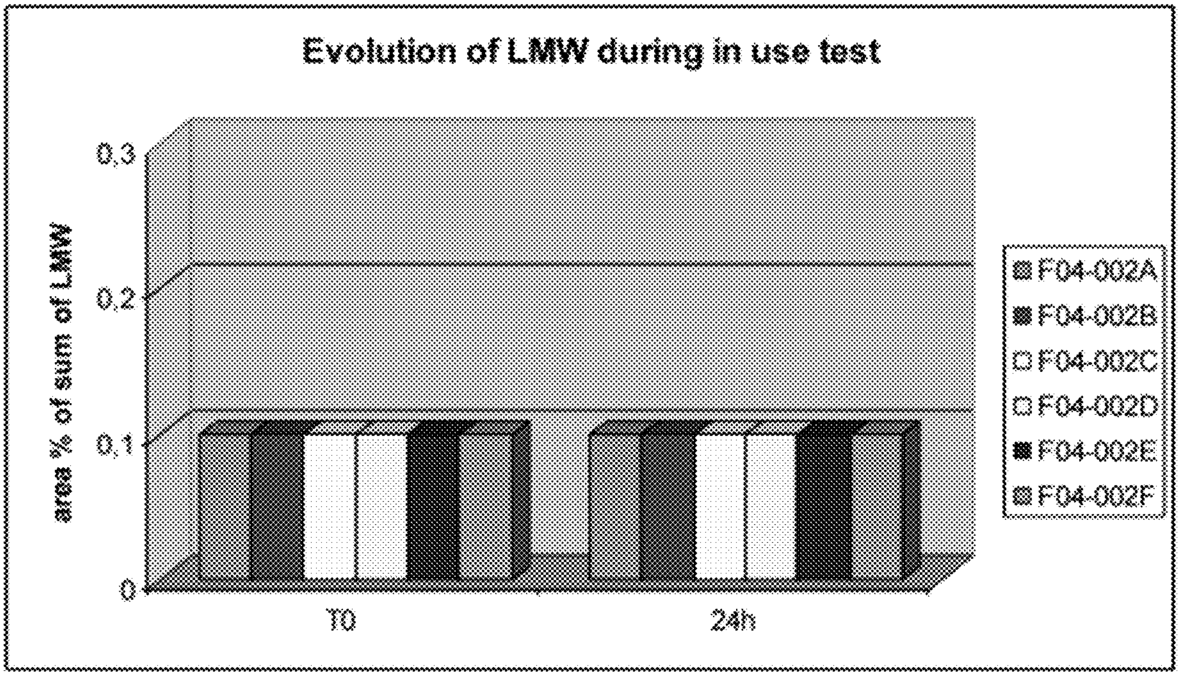
FIG. 22 is a graph depicting evolution of LMW during in-use simulation. For each timepoint, prototypes are represented from A to F.

FIG. 21 and FIG. 22 present the results of HMWs % and LMWs % after in-use simulation. During in-use simulation, no significant evolution was observed by SEC for all prototypes after dilution and storage 24 h at room temperature in bag.

Conclusion

Based on thermal stresses, sorbitol-based formulations (E & F) were better regarding Free Maytansinoids (T1M40° C.), fragmentation (T3M25° C. and T1M40° C.), and turbidity (T1M40° C.). All formulations were equivalent for other tested parameters.

Additionally, shaking stress followed by in-use simulation demonstrated that:

All formulations showed satisfactory results upon shaking stress and no significant difference between prototypes was highlighted.

Dilution in NaCl 0.9% at 0.8 mg/mL caused sub-visible particle formation, especially for formulations containing 100 ppm of PS80. Formulation E (Sorbitol 5%, PS80 100 ppm) did not pass the most strict pharmacopeia criteria by LO (HIAC).

Infusion of the diluted huMAb2-3-SPDB-DM4 at 0.8 mg/mL through the PE line+PES filter resulted in a significant decrease of protein concentration and DAR in the first milliliters.

Based on these results, an initial huMAb2-3-SPDB-DM4 formulation was selected: Na acetate 10 mM pH 5.5, sorbitol 5% (w/v), PS80 400 ppm (0.04%).

Example 3. Impact of Addition of EDTA to Formulation of huMAb2-3-SPDB-DM4

In presence of metal traces, accelerated degradation of polysorbate may be observed. Iron, along with other metals such as copper, is known to be involved in polysorbate 80 (PS80) degradation, even when present at very low concentration (ppb). Kranz et al., *J Pharm Sci* 2019 108(6):2022-2032. The addition of the chelating agent disodium EDTA was investigated to evaluate its ability to limit PS80 oxidation.

Study Design

The aim of this study was to assess the protective role of EDTA at three different concentrations (1, 10, and 50 μM) on huMAb2-3-SPDB-DM4 material that contains metal residues (representative of the reachable levels). A filling platform was used to mimic at laboratory scale the drug product (DP) filling step.

Samples were evaluated in terms of stability at 5° C., 25° C., and 40° C., up to 1 month. After formulation lock, additional analyses were performed up to 6 months on the selected EDTA concentration and comparative samples without EDTA.

TABLE 29

Test Formulations

| Name | Buffer | Target pH | Excipients | EDTA content | Target concentration (g/L) |
|---|---|---|---|---|---|
| w/o EDTA | Acetate 10 mM | 5.5 | Sorbitol 5% PS80 0.04% | 0 | 5.0 |
| EDTA 1 μM | Acetate 10 mM | 5.5 | Sorbitol 5% PS80 0.04% | 1 μM | 5.0 |
| EDTA 10 μM | Acetate 10 mM | 5.5 | Sorbitol 5% PS80 0.04% | 10 μM | 5.0 |
| EDTA 50 μM | Acetate 10 mM | 5.5 | Sorbitol 5% PS80 0.04% | 50 μM | 5.0 |

The four test formulations were stored at 5° C., 25° C., and 40° C. up to 1 month before formulation lock. Complementary analysis was performed up to 6 months at 25° C. (T6M25° C.) on a restricted number of prototypes and of analytical methods. Table 30 describes the time points, stress conditions, and analytical methods of the formulation study.

TABLE 30

Timepoints and analytical methods

| Timepoints | Purpose | Analytical Methods |
|---|---|---|
| Formulation Lock | | |
| T0 | Initial timepoint | Visual observation, pH, osmolality, protein concentration, DAR, SEC, DLS, MFI, EDTA content, CGE, iCIEF, Free drugs, PS80, PTMs |
| T1M5° C. | DP storage condition | Visual observation, pH, osmolality, protein concentration, DAR, SEC, DLS, MFI, CGE, iCIEF, Free drugs, PS80 |
| T1M25° C. | DP accelerated condition | Visual observation, pH, osmolality, protein concentration, DAR, SEC, DLS, MFI, CGE, iCIEF, Free drugs, PS80 |
| T2W40° C. | DP stress condition | Visual observation, pH, osmolality, protein concentration, DAR, SEC, DLS, MFI, CGE, iCIEF, Free drugs, PS80, PTMs |
| T1M40° C. | DP stress condition | Visual observation, pH, osmolality, protein concentration, DAR, SEC, DLS, MFI, CGE, iCIEF, Free drugs, PS80, PTMs |
| Complementary Analysis | | |
| T3M5° C. | Focus on selected formulation and without EDTA comparative sample | Visual observation, pH, osmolality, protein concentration, DAR, SEC, DLS, MFI, PS80 |
| T3M25° C. | Focus on selected formulation and without EDTA comparative sample | Visual observation, pH, osmolality, protein concentration, DAR, SEC, DLS, MFI, PS80 |

TABLE 30-continued

| Timepoints and analytical methods | | |
|---|---|---|
| Timepoints | Purpose | Analytical Methods |
| | Formulation Lock | |
| T6M25° C. | Focus on selected formulation and without EDTA comparative sample | PS80 |

The drug substance (DS) used for this study contained 24 ng/mL of Iron and 7 ng/mL of Ni. The DS as so provided was formulated in Acetate 10 mM, Sorbitol 5%, PS80 0.04%, pH 5.5, 5 g/L, and was stored at −20° C.

Methods

Preparation of Primary Packaging Materials

Glass vials were manually washed with water for injection (WFI) and depyrogenized in oven before filling. Stoppers were sterilized by autoclaving.

Formulations Preparation

Three EDTA stock solutions (50 μM, 500 μM, and 2500 μM) were prepared by dissolving disodium EDTA in WFI in graduated glass flasks. The obtained solutions were filtered using 0.22 μm sterilizing syringe filters.

The ADC DS was thawed, pooled in a 10 L polycarbonate (PC) bottle, and homogenized by manual inversion of the bottle. The ADC DS was then divided into six 2 L PC bottles filled at 1.5 L (1.527 kg) with a peristaltic pump.

EDTA stock solutions were then added to the ADC DS and homogenized by manual inversion of the bottles. Table 31 gathers the calculated volumes of EDTA stock solution to be added to the ADC DS, in order to obtain the following target concentration: no EDTA, 1 μM, 10 μM and 50 μM.

TABLE 31

| EDTA spiking volumes | | | |
|---|---|---|---|
| Targeted EDTA concentration | EDTA 50 μM | EDTA 500 μM | EDTA 2500 μM |
| 0 μM | 0 | 0 | 0 |
| 1 μM | 30.6 mL | 0 | 0 |
| 10 μM | 0 | 30.6 mL | 0 |
| 50 μM | 0 | 0 | 30.6 mL |

Once prepared, solutions were stored at 5° C. until the start of the DP filling. After EDTA spiking, the dilution factor of initial formulation was estimated at approximately 2%.

Vial Filling

After formulation, the product was filtered in a 10 L intermediate bag and then filled into 10 R vials on a dedicated filling platform mimicking the industrial drug product (DP) process. The filled vials were then manually stoppered and crimped.

Analytical Methods

Visual Observation

Samples were visually inspected under a pharmacopeia chamber and an optical fiber MLC-150C from MOTIC to analyze the presence of visible particles (scoring detailed in Table 32).

TABLE 32

| Ranking for visual observation | | | |
|---|---|---|---|
| Detection of particles | | Number of particles | |
| 0 | Not detected with cold light (optical fiber) | + | Countable (1 ≤ n ≤ 5) |
| 1 | Detected only with cold light (optical fiber) | ++ | Several (n > 5) |
| 2 | visible particle on visual inspection table (Eur. Ph. Conditions) | +++ | Numerous |

MicroFlow Imaging (MFI)

For MFI analysis, 1 mL of samples was needed, without any dilution. The method used was the following: sample flows at 0.1 mL/min into the cell, recording starts after 0.2 mL of purge. Measures were performed at room temperature. Hellmanex 3% and MilliQ filtered water flushing were performed before and after each measurement.

Dynamic Light Scattering

80 μL of solution was analyzed on Nanosizer (Zetasizer nano-S, Malvern) with following parameters: 3 measurements of 11 runs of 10 seconds, with an incidence angle of 173°. No dilution needed. Results are presented as average of the three measurements.

pH

Measurements were performed at room temperature, by dropping the pH probe in 2 mL of sample.

Osmolality

Osmolality measurements were performed using a freezing-point osmometer. Measures were repeated 3 times and results are presented as average. A volume of 20 μL was needed for each measure.

PS80 Content

PS80 content was measured by gas chromatography (GC).

Results and Discussion

Results discussed below are restricted to stress conditions 40° C. and 25° C. as no difference and no evolution between samples were observed on the 5° C. storage condition. Formulation lock was performed after T1M results and it was decided to only analyze the selected formulation of 10 μM and without EDTA comparison sample for later timepoints.

Visual Observation

Visual observation results are presented in Table 33.

According to the Eu. Ph. method, all formulations were considered essentially free from visible particles at all stress points except T2W40° C. The presence of visible particles was not confirmed at T1M40° C. and was therefore attributed to non-GMP environment preparation.

When using the optical fiber method (more sensitive than the Eu. Ph. method), some particles were observed in all formulations and at all timepoints, without trend.

No significant difference and evolution could be observed in presence or absence of EDTA.

pH and Osmolality pH and osmolality values are presented in Table 34.

For pH, no evolution was highlighted. Values remained constant and compliant with acceptance criteria (5.2-5.8). Osmolality values did not show any evolution over time for all samples, regardless EDTA concentration.

Protein Concentration and DAR (UV)

Protein concentration and DAR results are presented in Table 35.

Protein concentration values did not show a significant evolution over time for all samples, regardless of the EDTA concentration.

Figure 23:
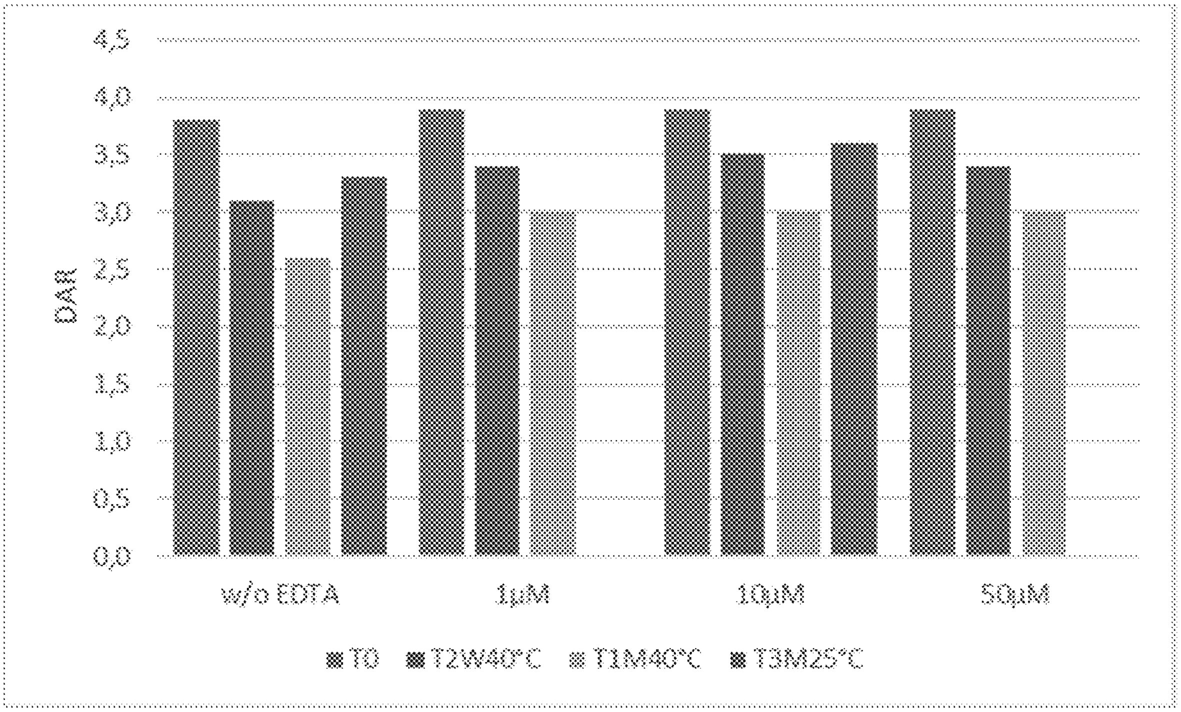
FIG. 23 is a graph depicting DAR evolution in filled vials for samples with indicated concentrations of EDTA following indicated thermal stress. T0, time zero; T2W40° C., two weeks at 40° C.; T1M T2W40° C., one month at 40° C.; T3M25° C., 3 months at 25° C. (Example 3). T3M25° C. timepoint analyzed only for the w/o EDTA and the 10 μM EDTA samples.

DAR values decreased over time for all samples after T2M40° C. and T1M40° C. (FIG. 23).

A higher decrease over time was observed for samples without EDTA (−1.2 at T1M40° C. w/o EDTA, versus −0.9 at T1M40° C. for the three EDTA concentrations). This trend was confirmed on the 3M25° C. timepoint, with a higher decrease on the w/o EDTA sample compared to the 10 μM EDTA sample.

TABLE 33

| Visual observation | | | | | | | | | | | | | | | | | | |
|---|---|---|---|---|---|---|---|---|---|---|---|---|---|---|---|---|---|---|
| | T0 | | | | T2W40° C. | | | | T1M40° C. | | | | T1M25° C. | | | | T3M25° C. | |
| EDTA μM | 0 | 1 | 10 | 50 | 0 | 1 | 10 | 50 | 0 | 1 | 10 | 50 | 0 | 1 | 10 | 50 | 0 | 50 |
| Vis. Obs. | 1++ | 1++ | 1++ | 1++ | 1+ | 2+++ | 2++ | 2++ | 1+ | 1+++ | 1++ | 1++ | 1++ | 1++ | 1+++ | 1+++ | 1++ | 1+ |

TABLE 34

| pH and osmolality | | | | | | | | | | | | | | | | | | |
|---|---|---|---|---|---|---|---|---|---|---|---|---|---|---|---|---|---|---|
| | T0 | | | | T2W40° C. | | | | T1M40° C. | | | | T1M25° C. | | | | T3M25° C. | |
| EDTA μM | 0 | 1 | 10 | 50 | 0 | 1 | 10 | 50 | 0 | 1 | 10 | 50 | 0 | 1 | 10 | 50 | 0 | 50 |
| pH Osm. | 5.5 | 5.5 | 5.5 | 5.5 | 5.5 | 5.5 | 5.5 | 5.5 | 5.5 | 5.5 | 5.5 | 5.5 | 5.5 | 5.5 | 5.5 | 5.5 | 5.5 | 5.5 |

TABLE 35

| Protein concentration and DAR | | | | | | | | | | | | | | | | | | |
|---|---|---|---|---|---|---|---|---|---|---|---|---|---|---|---|---|---|---|
| | T0 | | | | T2W40° C. | | | | T1M40° C. | | | | T1M25° C. | | | | T3M25° C. | |
| EDTA μM | 0 | 1 | 10 | 50 | 0 | 1 | 10 | 50 | 0 | 1 | 10 | 50 | 0 | 1 | 10 | 50 | 0 | 50 |
| Conc. mg/mL | 4.4 | 4.3 | 4.7 | 4.5 | 4.5 | 4.4 | 4.8 | 4.6 | 4.5 | 4.4 | 4.8 | 4.6 | 4.5 | 4.4 | 4.7 | 4.5 | 4.6 | 4.8 |
| DAR | 3.8 | 3.9 | 3.9 | 3.9 | 3.1 | 3.4 | 3.5 | 3.4 | 2.6 | 3.0 | 3.0 | 3.0 | 3.8 | 3.8 | 3.9 | 3.8 | 3.3 | 3.6 |

TABLE 36

| Z average and PDI % | | | | | | | | | | | | | | | | | | |
|---|---|---|---|---|---|---|---|---|---|---|---|---|---|---|---|---|---|---|
| | T0 | | | | T2W40° C. | | | | T1M40° C. | | | | T1M25° C. | | | | T3M25° C. | |
| EDTA μM | 0 | 1 | 10 | 50 | 0 | 1 | 10 | 50 | 0 | 1 | 10 | 50 | 0 | 1 | 10 | 50 | 0 | 50 |
| Zav (nm) | 11.2 | 11.2 | 11.2 | 11.3 | 11.3 | 11.2 | 11.3 | 11.4 | 11.3 | 11.2 | 11.2 | 11.2 | 11.1 | 11.0 | 11.2 | 11.0 | 11.4 | 11.2 |
| PDI % | 21.7 | 21.3 | 20.5 | 23.9 | 26.5 | 36.4 | 23.2 | 26.1 | 24.9 | 25.5 | 20.2 | 23.5 | 27.5 | 19.4 | 18.9 | 22.0 | 30.0 | 21.6 |

TABLE 37

| MFI results | | | | | | | | | | | | | | | | | | |
|---|---|---|---|---|---|---|---|---|---|---|---|---|---|---|---|---|---|---|
| | T0 | | | | T2W40° C. | | | | T1M40° C. | | | | T1M25° C. | | | | T3M25° C. | |
| EDTA μm | 0 | 1 | 10 | 50 | 0 | 1 | 10 | 50 | 0 | 1 | 10 | 50 | 0 | 1 | 10 | 50 | 0 | 50 |
| ≥2 μm | 329 | 367 | 406 | 292 | 229 | 719 | 1104 | 310 | 376 | 237 | 906 | 171 | 902 | 714 | 846 | 751 | 1381 | 1166 |
| ≥10 μm | 0 | 8 | 0 | 10 | 5 | 30 | 32 | 4 | 0 | 0 | 8 | 9 | 0 | 6 | 53 | 21 | 39 | 15 |
| ≥25 μm | 0 | 2 | 0 | 2 | 0 | 5 | 5 | 0 | 0 | 0 | 2 | 3 | 0 | 2 | 10 | 8 | 6 | 6 |

TABLE 38

Monomer and HMWs

| | T0 | | | | T2W40° C. | | | | T1M40° C. | | | | T1M25° C. | | | | T3M25° C. | |
|---|---|---|---|---|---|---|---|---|---|---|---|---|---|---|---|---|---|---|
| EDTA μM | 0 | 1 | 10 | 50 | 0 | 1 | 10 | 50 | 0 | 1 | 10 | 50 | 0 | 1 | 10 | 50 | 0 | 50 |
| Monomer % | 96.6 | 96.6 | 96.6 | 96.6 | 95.4 | 96.5 | 96.2 | 96.2 | 93.2 | 95.3 | 94.8 | 95.0 | 97.2 | 97.5 | 97.3 | 97.4 | 96.1 | 96.7 |
| HMWs % | 1.1 | 1.1 | 1.2 | 1.1 | 2.1 | 1.8 | 2.0 | 1.9 | 3.1 | 2.1 | 2.5 | 2.3 | 1.3 | 1.2 | 1.3 | 1.3 | 1.7 | 1.5 |

TABLE 39

Reduced cGE results

| | T0 | | | | T2W40° C. | | | | T1M40° C. | | | | T1M25° C. | | | |
|---|---|---|---|---|---|---|---|---|---|---|---|---|---|---|---|---|
| EDTA μM | 0 | 1 | 10 | 50 | 0 | 1 | 10 | 50 | 0 | 1 | 10 | 50 | 0 | 1 | 10 | 50 |
| Sum of light and heavy chains (corrected area %) | 98.2 | 97.8 | 98.1 | 98.3 | 97.8 | 98.0 | 97.8 | 97.9 | 95.6 | 97.5 | 98.2 | 97.3 | 98.2 | 98.1 | 98.1 | 97.9 |

TABLE 40

Non-reduced cGE results

| | T0 | | | | T2W40° C. | | | | T1M40° C. | | | | T1M25° C. | | | |
|---|---|---|---|---|---|---|---|---|---|---|---|---|---|---|---|---|
| EDTA μM | 0 | 1 | 10 | 50 | 0 | 1 | 10 | 50 | 0 | 1 | 10 | 50 | 0 | 1 | 10 | 50 |
| Purity (H2L2, corrected area %) | 87.1 | 87.1 | 87.3 | 87.2 | 85.2 | 86.9 | 86.9 | 86.6 | 84.8 | 87.2 | 86.7 | 87.0 | 85.0 | 86.1 | 86.2 | 86.0 |
| Main fragment (RMT 0.96, corrected area %) | 9.3 | 9.3 | 9.1 | 9.3 | 10.0 | 9.6 | 9.6 | 9.7 | 8.3 | 7.7 | 8.0 | 8.0 | 10.5 | 10.4 | 10.3 | 10.4 |
| Sum of other fragments (corrected area %) | 3.5 | 3.5 | 3.6 | 3.5 | 4.8 | 3.5 | 3.5 | 3.5 | 6.9 | 5.1 | 5.2 | 5.0 | 4.5 | 3.5 | 3.6 | 3.5 |

TABLE 41

PS80 content

| | T0 | | | | T2W40° C. | | | | T1M40° C. | | | | T1M25° C. | | | | T3M25° C. | | T6M25° C. | | | |
|---|---|---|---|---|---|---|---|---|---|---|---|---|---|---|---|---|---|---|---|---|---|---|
| EDTA μM | 0 | 1 | 10 | 50 | 0 | 1 | 10 | 50 | 0 | 1 | 10 | 50 | 0 | 1 | 10 | 50 | 0 | 50 | 0 | 1 | 10 | 50 |
| PS80 ppm | 310 | 323 | 332 | 317 | 282 | 298 | 329 | 315 | 241 | 311 | 333 | 319 | 300 | 309 | 331 | 331 | 233 | 390 | 103 | 317 | 333 | 317 |

TABLE 42

Low PI and main isoform by iCIEF

| | T0 | | | | T2W40° C. | | | | T1M40° C. | | | | T1M25° C. | | | |
|---|---|---|---|---|---|---|---|---|---|---|---|---|---|---|---|---|
| EDTA μM | 0 | 1 | 10 | 50 | 0 | 1 | 10 | 50 | 0 | 1 | 10 | 50 | 0 | 1 | 10 | 50 |
| Sum of high pI isoforms (area %) | 9 | 9 | 9 | 9 | 7 | 8 | 8 | 8 | 4 | 6 | 5 | 7 | 9 | 9 | 9 | 9 |

TABLE 42-continued

| Low PI and main isoform by iCIEF | | | | | | | | | | | | | | | | |
|---|---|---|---|---|---|---|---|---|---|---|---|---|---|---|---|---|
| | T0 | | | | T2W40° C. | | | | T1M40° C. | | | | T1M25° C. | | | |
| EDTA μM | 0 | 1 | 10 | 50 | 0 | 1 | 10 | 50 | 0 | 1 | 10 | 50 | 0 | 1 | 10 | 50 |
| Sum of main isoforms (area %) | 83 | 83 | 82 | 82 | 77 | 81 | 81 | 81 | 66 | 74 | 73 | 72 | 82 | 82 | 82 | 83 |
| Sum of low pI isoforms (area %) | 8 | 8 | 9 | 8 | 15 | 11 | 11 | 10 | 30 | 20 | 22 | 21 | 9 | 9 | 9 | 9 |

TABLE 43

| Total of free maytansinoids | | | | | | | | | | | | | | | | |
|---|---|---|---|---|---|---|---|---|---|---|---|---|---|---|---|---|
| | T0 | | | | T2W40° C. | | | | T1M40° C. | | | | T1M25° C. | | | |
| EDTA μM | 0 | 1 | 10 | 50 | 0 | 1 | 10 | 50 | 0 | 1 | 10 | 50 | 0 | 1 | 10 | 50 |
| Total free | 0.1 | 0.1 | 0.1 | 0.1 | 1.5 | 1.4 | 1.5 | 1.4 | 2.9 | 2.7 | 2.7 | 2.6 | 0.5 | 0.6 | 0.6 | 0.6 |
| Oxidized species | − | − | − | − | − | − | − | − | + | − | − | − | − | − | − | − |
| Impurity A | ND | ND | ND | ND | 0.25 | 0.07 | 0.10 | 0.09 | 0.69 | 0.41 | 0.43 | 0.41 | ND | ND | ND | ND |
| No. other maytansinoids impurities ≥ LOQ | 0 | 0 | 0 | 0 | 1 | 1 | 0 | 0 | 8 | 5 | 4 | 4 | 0 | 0 | 0 | 0 |

TABLE 44

| Met255 and Met431 oxidation | | | | | | | | | | | | |
|---|---|---|---|---|---|---|---|---|---|---|---|---|
| | T0 | | | | T2W40° C. | | | | T1M40° C. | | | |
| EDTA μM | 0 | 1 | 10 | 50 | 0 | 1 | 10 | 50 | 0 | 1 | 10 | 50 |
| Met255 oxidation (%) | 5 | 4 | 5 | 4 | 8 | 5 | 6 | 5 | 23 | 10 | 12 | 11 |
| Met431 oxidation (%) | 2 | 2 | 1 | 1 | 3 | 2 | 2 | 2 | 10 | 4 | 4 | 4 |

Submicronic Particles (DLS)

In Table 36 are presented the values of PdI % and Z average over time.

No trend was observed on Zav for all timepoints and all EDTA concentrations. Regarding PDI %, a slight increase was observed for most samples at 25° C. and at 40° C. timepoints. However, no clear trend could be highlighted with regards to EDTA content.

Subvisible Particles (MFI)

Subvisible particles results are presented in Table 37.

No difference between prototypes can be seen for all timepoints. A very slight increase of sub-visible particles was observed on the T3M25° C. timepoint; this increase was similar for w/o EDTA and 10 μM EDTA samples.

Purity and HMWs % by Size Exclusion Chromatography (SEC)

Table 38 presents results for SEC (Monomer % and HMWs %).

Figure 24:
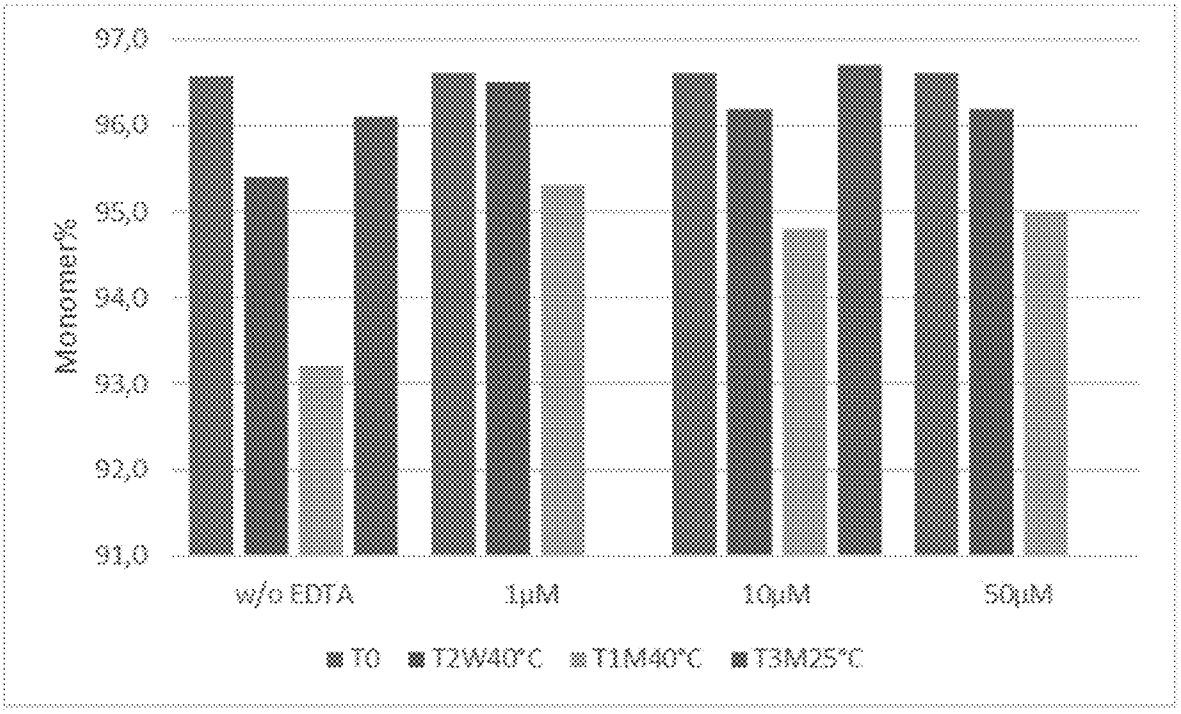
FIG. 24 is a graph depicting monomer % variation in filled vials for samples with indicated concentrations of EDTA following indicated thermal stress. T3M25° C. timepoint analyzed only for the w/o EDTA and the 10 μM EDTA samples.

Monomer % decreased after T1M40° C. for all samples, at a faster rate in absence of EDTA (−3.4% at T1M40° C. on the w/o EDTA sample, −1.3/−1.8% on the samples with EDTA, see FIG. 24).

Figure 25:
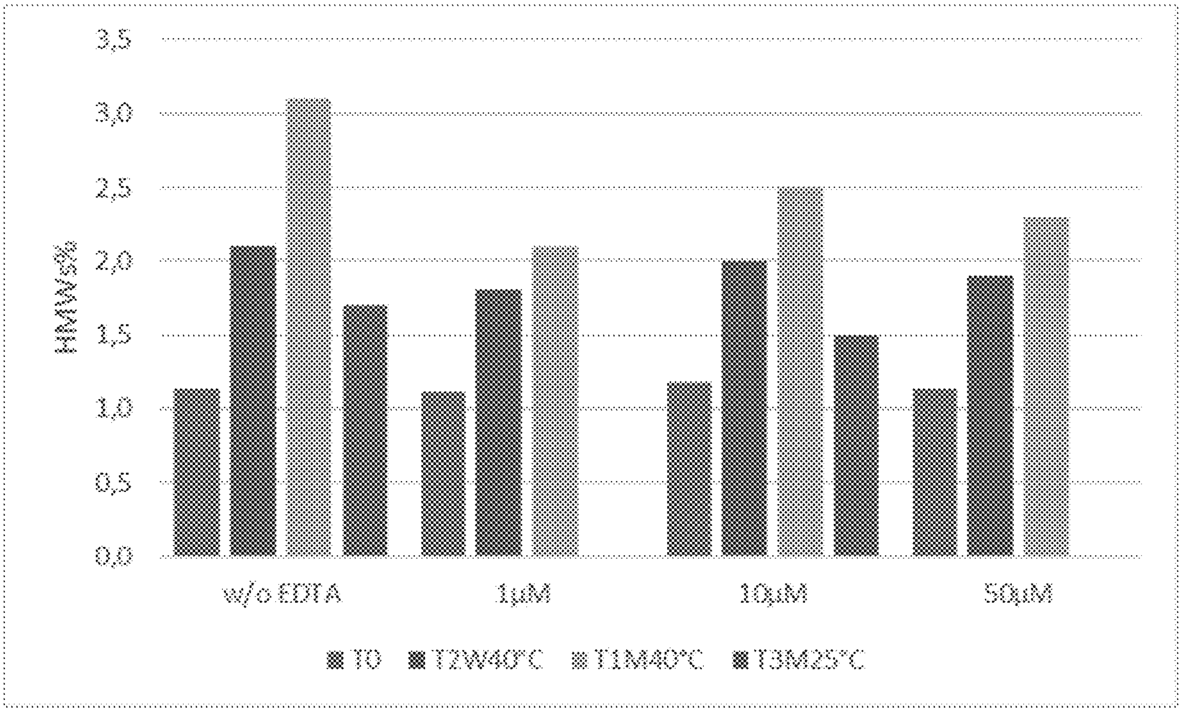
FIG. 25 is a graph depicting high molecular weight species (HMWs) % variation in filled vials for samples with indicated concentrations of EDTA following indicated thermal stress. T3M25° C. timepoint analyzed only for the w/o EDTA and the 10 μM EDTA samples.

This result was confirmed by the increase of HMWs %, which is higher for the w/o EDTA sample (+2.0% at T1M40° C. on the w/o EDTA sample, +1.0/+1.3% on the with EDTA samples, see FIG. 25).

No significant differentiation can be done between the three tested EDTA concentrations on both Monomer % and HMWs %.

Purity and Fragmentation by CGE

Table 39 and Table 40 present results of CGE in Reduced (Sum of light and heavy chains %) and Non-reduced conditions (purity %, main fragments % and Sum of other fragments %).

Figure 26:
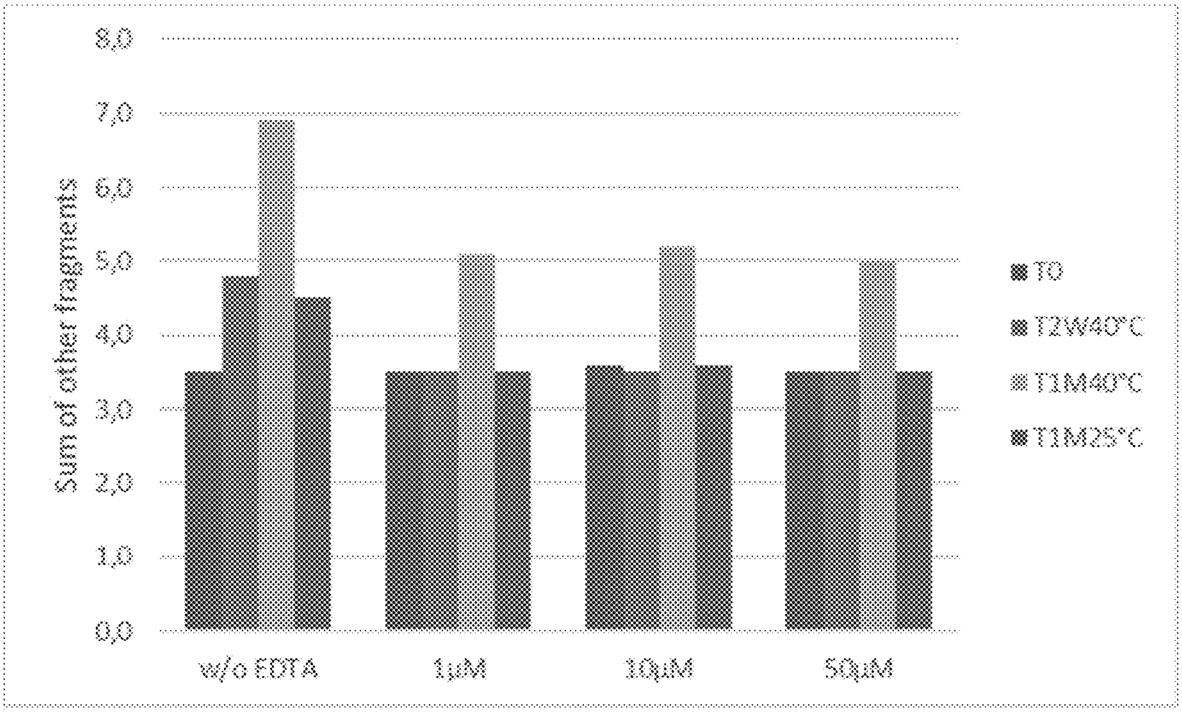
FIG. 26 is a graph depicting sum of other fragments evolution for samples with indicated concentrations of EDTA following indicated thermal stress.
Figure 27:
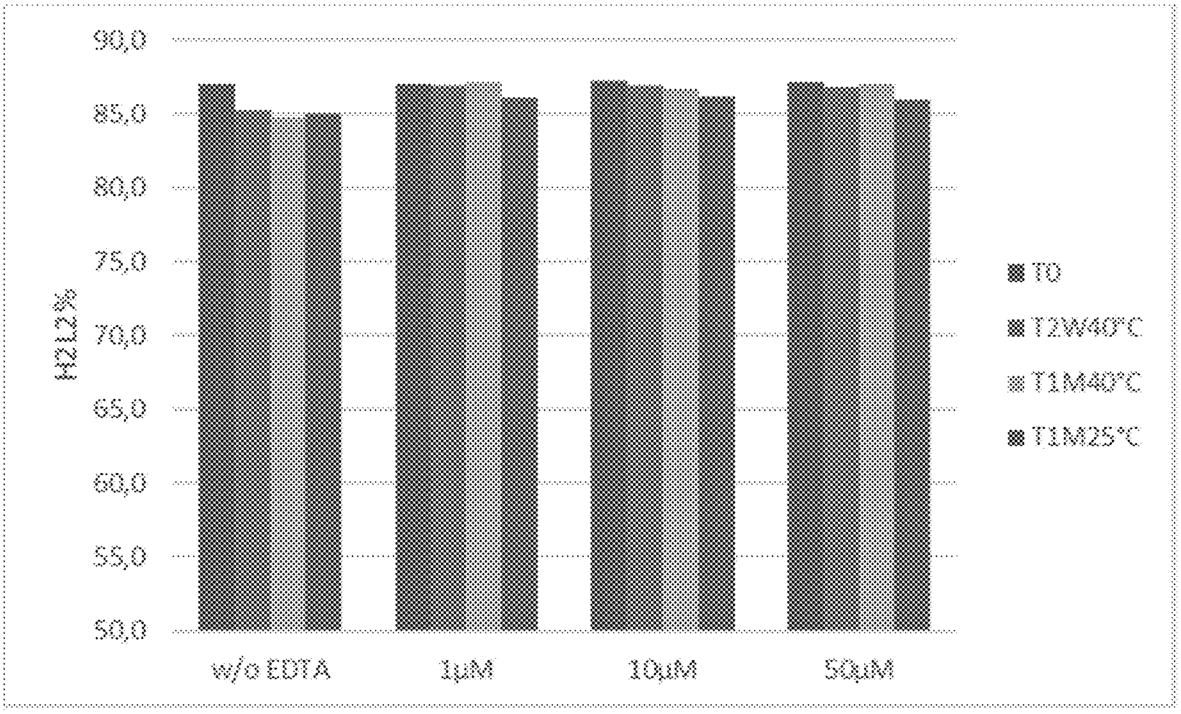
FIG. 27 is a graph depicting H2L2% variation for samples with indicated concentrations of EDTA following indicated thermal stress (non-reducing capillary gel electrophoresis).

In non-reduced cGE (Table 40, FIG. 26 and FIG. 27), a significant decrease in terms of purity occurred after 1M40° C. in absence of EDTA, confirmed by an increase of fragments (sum of all fragments). With the three EDTA concentrations, no significant evolution was observed at T2W40° C., T1M25° C. and T1M40° C.

Figure 28:
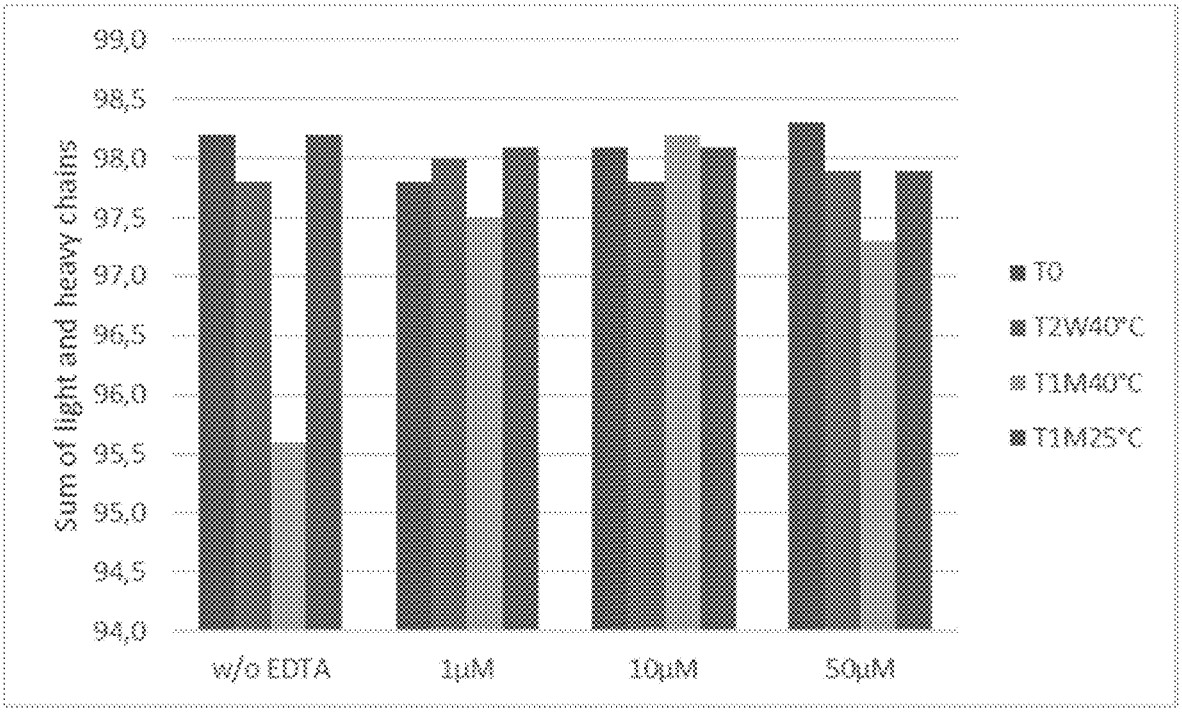
FIG. 28 is a graph of sum of light and heavy chains % for samples with indicated concentrations of EDTA following indicated thermal stress (reducing capillary gel electrophoresis).

In Reduced cGE (see Table 39 and FIG. 28), a significant decrease in terms of sum of light and heavy chains occurred after 1M40° C. in absence of EDTA. With the three EDTA concentrations, no significant variation was observed at T2W40° C., T1M25° C. and T1M40° C.

PS80 Content by Gas Chromatography (GC)

Table 41 presents results of PS80 content.

Figure 29:
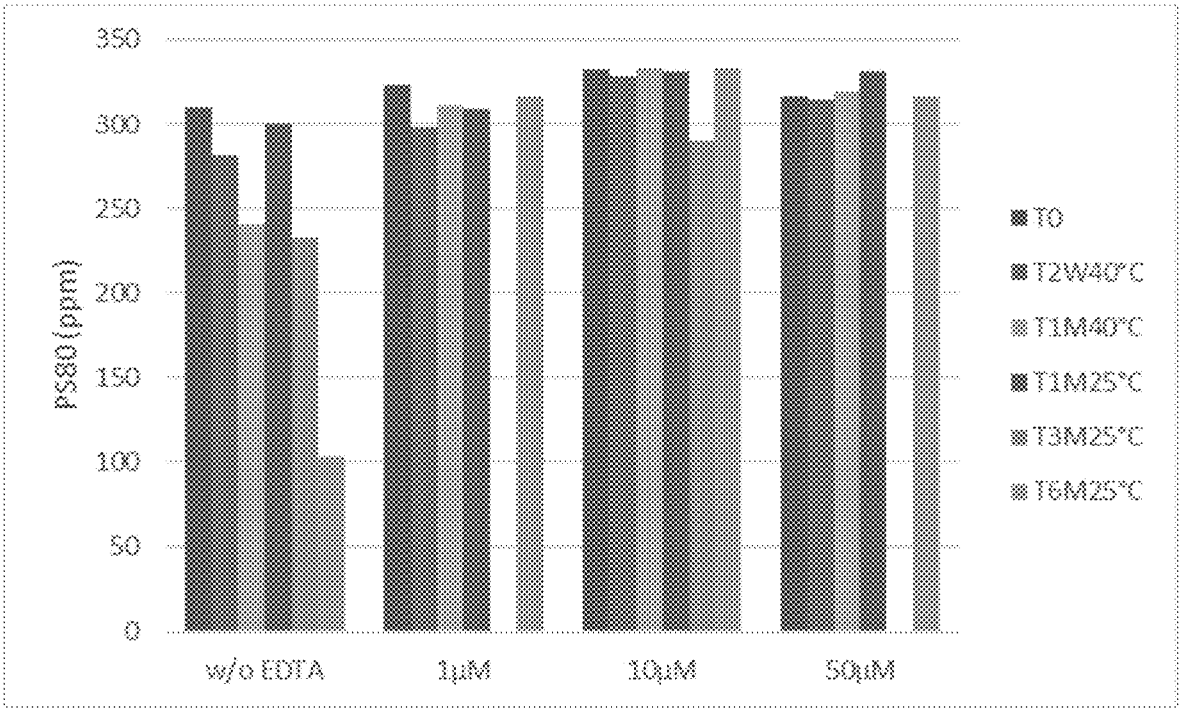
FIG. 29 is a graph depicting PS80 content for samples with indicated concentrations of EDTA following indicated thermal stress. T3M25° C. timepoint not analyzed for 1 μM and 50 μM EDTA samples.

For all EDTA concentrations, no significant decrease of PS80 content was recorded up to T6M25° C. A significant decrease of PS80 was observed after T1M40° C. and T6M25° C. in absence of EDTA (see also FIG. 29).

Charge Variants Analysis by Imaged Capillary Isoelectric Focusing (iCIEF)

Table 42 gathers iCIEF results (Sum of main isoforms %, sum of high pI isoforms % and sum of low PI isoforms %).

Figure 30:
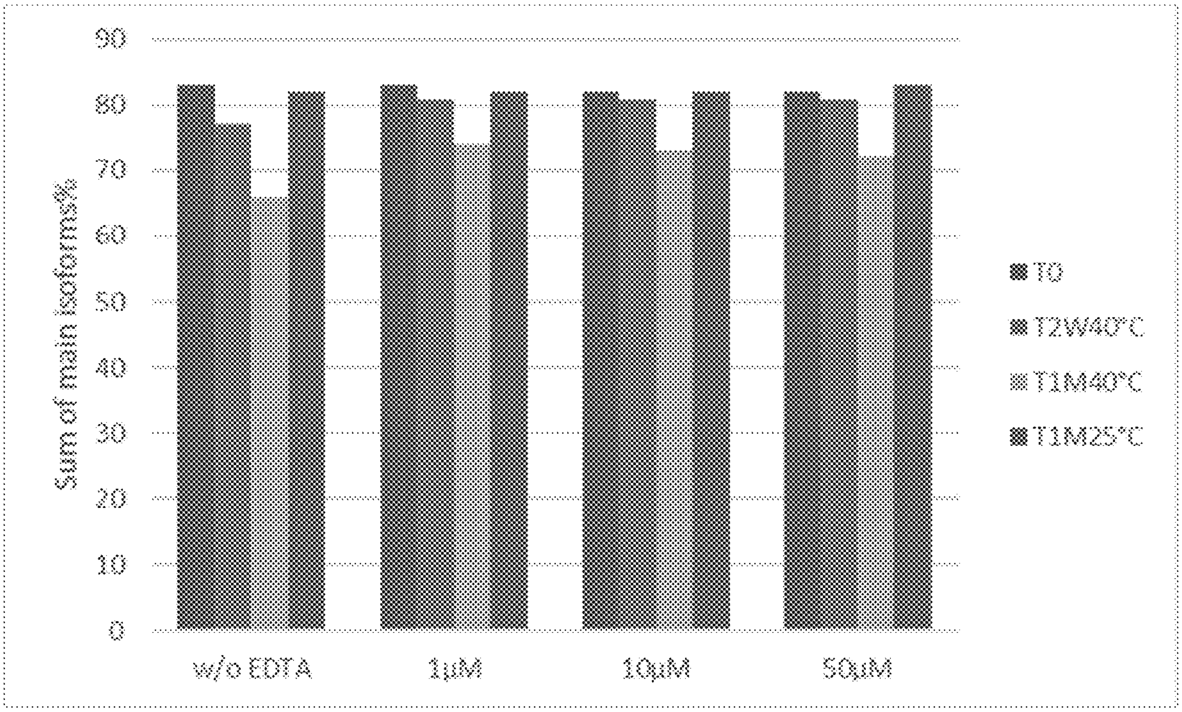
FIG. 30 is a graph depicting sum of main isoforms % in filled vials for samples with indicated concentrations of EDTA following indicated thermal stress
Figure 31:
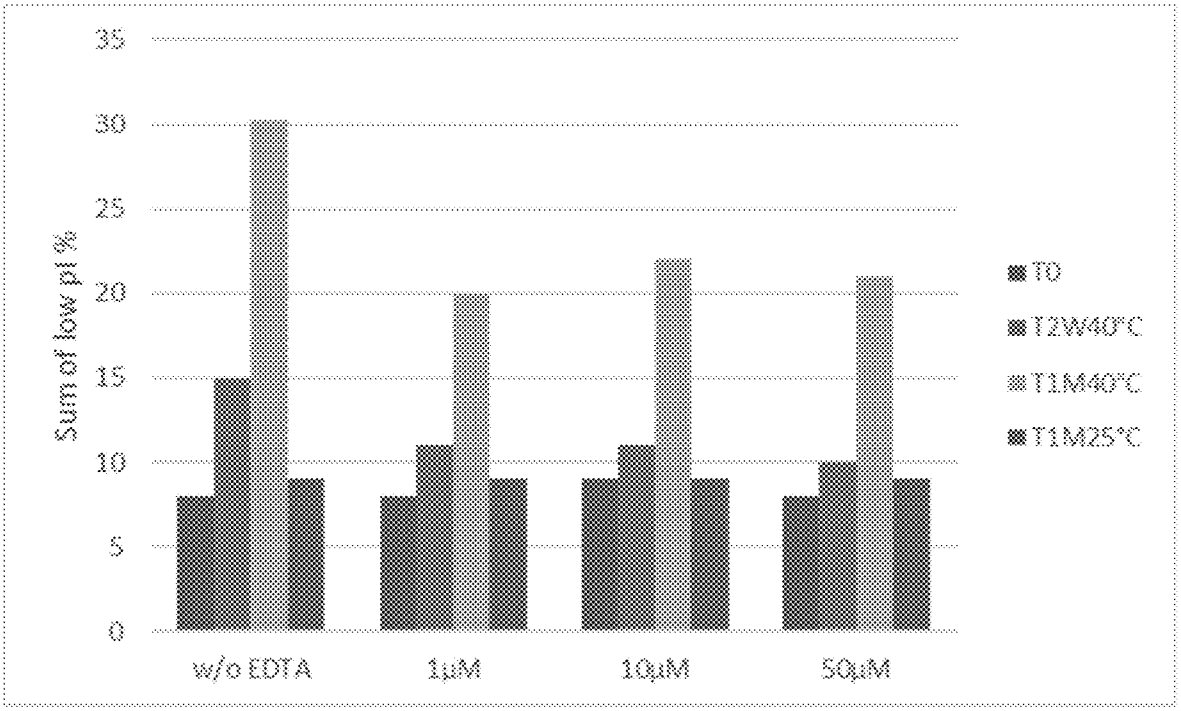
FIG. 31 is a graph depicting sum of low pI % in filled vials for samples with indicated concentrations of EDTA following indicated thermal stress.

Under 40° C. stress condition, samples with EDTA had an improved stability regarding charge isoforms. The increase of sum of low pI isoforms and the decrease of main isoforms was more pronounced without EDTA (Low pI: +22% at T1M40° C. w/o EDTA, +12-13% with EDTA. Main isoforms: −17% w/o EDTA, −9/−10% with EDTA, see also FIGS. 30 and 31). No significant difference is highlighted with regards to the EDTA concentration.

Free Maytansinoids Content

Table 43 presents the results of free drug analysis.

No significant difference can be highlighted in terms of total amount of Free drug for all samples, with and w/o EDTA. However, a difference can be seen in terms of percentage of impurity A: after 2 weeks and 1 month at 40° C., impurity A percentage was higher in absence of EDTA, in comparison with EDTA samples. The three EDTA concentrations cannot be differentiated. Also, without EDTA, oxidized species appeared after 1M40° C., while no oxidized species were detected in presence of EDTA.

Post Translation Modifications

Only Met255 and Met431 oxidation is discussed in this section, as no difference was noticed between formulations for other PTM.

PTM analyses showed that in presence of EDTA M255 and M431 positions oxidized in a lower extent in comparison with samples w/o EDTA. No significant difference between the three EDTA concentrations could be seen (see Table 44).

CONCLUSION

For all tested conditions, the three EDTA concentrations provided an efficient stabilization of PS80 content and of other quality attributes that may be impacted by oxidative processes (notably, PTMs, Free maytansinoids, cGE, iCIEF, and SEC).

The invention claimed is:

1. A liquid pharmaceutical formulation comprising:

an antibody-drug conjugate (ADC) comprising an anti-human carcinoembryonic antigen-related cell adhesion molecule 5 (hCEACAM5) antibody conjugated to a maytansinoid derivative 4 (DM4) by a N-succinimidyl-4-(2-pyridyldithio) butanoic acid (SPDB) linker conjugate; wherein the antibody comprises a variable heavy (VH) domain of amino acid sequence of SEQ ID NO:6 and a variable light (VL) domain of amino acid sequence of SEQ ID NO: 7, at a concentration of about 5 mg/mL;

the formulation consisting of the following excipients:

i) sodium acetate at a concentration of about 10 mM;

ii) sorbitol at a concentration of about 5% w/v, iii) polysorbate 80 at a concentration of about 0.04% w/v; and iv) disodium EDTA at a concentration of between about 1 μM and about 50 μM, wherein the formulation has a pH of about 5.5.

2. The pharmaceutical formulation of claim 1, wherein the disodium EDTA is at a concentration of about 1 μM, about 10 μM or about 50 μM.

3. The pharmaceutical formulation of claim 1, wherein the antibody-drug conjugate has a drug-to-conjugate ratio ranging from about 1 to about 10, from about 2 to about 5, or from about 3 to about 4.

4. A method of treating a cancer, comprising administering to a subject in need thereof an effective amount of a pharmaceutical formulation comprising:

an antibody-drug conjugate (ADC) comprising an anti-human carcinoembryonic antigen-related cell adhesion molecule 5 (hCEACAM5) antibody bound to a maytansinoid derivative 4 (DM4) by a N-succinimidyl-4-(2-pyridyldithio) butanoic acid (SPDB) linker; wherein the antibody comprises a variable heavy (VH) domain of amino acid sequence of SEQ ID NO: 6 and a variable light (VL) domain of amino acid sequence of SEQ ID NO:7;

the formulation consisting of the following excipients:

i) sodium acetate at a concentration of about 10 mM;

ii) sorbitol at a concentration of about 5% w/v;

iii) polysorbate 80 at a concentration of about 0.04% w/v; and iv) disodium EDTA at a concentration of between about 1 μM and about 50 μM;

wherein the formulation has a pH of about 5.5.

5. The method according to claim 4, wherein the cancer is a high carcinoembryonic antigen-related cell adhesion molecule 5 (CEACAM5) expressing cancer.

6. The method according to claim 4, wherein the cancer is selected from the group consisting of colorectal, gastric, lung, breast, prostate, ovarian, cervical, pancreatic and bladder cancer.

7. The method according to claim 4, wherein the cancer expresses carcinoembryonic antigen-related cell adhesion molecule 5 (CEACAM5).

8. The method according to claim 4, wherein the cancer is selected from the group consisting of pancreatic and prostate cancer.

9. A liquid pharmaceutical formulation consisting of:

i) 5 mg/mL anti-human carcinoembryonic antigen-related cell adhesion molecule 5 (hCEACAM5) antibody-drug conjugate (ADC);

ii) sodium acetate at a concentration of 10 mM;

iii) sorbitol at a concentration of 5% w/v;

iv) polysorbate 80 at a concentration of 0.04% w/v; and v) disodium EDTA at a concentration of 10 μM;

wherein the liquid dosage form has a pH of 5.5, and wherein the ADC consists of huMAb2-3-SPDB-DM4.

* * * * *

SEQUENCE LISTING

```
<160> NUMBER OF SEQ ID NOS: 9

<210> SEQ ID NO 1
<211> LENGTH: 8
<212> TYPE: PRT
<213> ORGANISM: Artificial sequence
<220> FEATURE:
<223> OTHER INFORMATION: Synthetic peptide

<400> SEQUENCE: 1

Gly Phe Val Phe Ser Ser Tyr Asp
1               5


<210> SEQ ID NO 2
<211> LENGTH: 8
<212> TYPE: PRT
<213> ORGANISM: Artificial sequence
<220> FEATURE:
<223> OTHER INFORMATION: Synthetic peptide

<400> SEQUENCE: 2

Ile Ser Ser Gly Gly Gly Ile Thr
1               5


<210> SEQ ID NO 3
<211> LENGTH: 13
<212> TYPE: PRT
<213> ORGANISM: Artificial sequence
<220> FEATURE:
<223> OTHER INFORMATION: Synthetic peptide

<400> SEQUENCE: 3

Ala Ala His Tyr Phe Gly Ser Ser Gly Pro Phe Ala Tyr
1               5                   10


<210> SEQ ID NO 4
<211> LENGTH: 6
<212> TYPE: PRT
<213> ORGANISM: Artificial sequence
<220> FEATURE:
<223> OTHER INFORMATION: Synthetic peptide

<400> SEQUENCE: 4

Glu Asn Ile Phe Ser Tyr
1               5


<210> SEQ ID NO 5
<211> LENGTH: 9
<212> TYPE: PRT
<213> ORGANISM: Artificial sequence
<220> FEATURE:
```

-continued

<223> OTHER INFORMATION: Synthetic peptide

<400> SEQUENCE: 5

```
Gln His His Tyr Gly Thr Pro Phe Thr
1               5
```

<210> SEQ ID NO 6
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 6

```
Glu Val Gln Leu Gln Glu Ser Gly Pro Gly Leu Val Lys Pro Gly Gly
1               5                   10                  15

Ser Leu Ser Leu Ser Cys Ala Ala Ser Gly Phe Val Phe Ser Ser Tyr
            20                  25                  30

Asp Met Ser Trp Val Arg Gln Thr Pro Glu Arg Gly Leu Glu Trp Val
        35                  40                  45

Ala Tyr Ile Ser Ser Gly Gly Gly Ile Thr Tyr Ala Pro Ser Thr Val
    50                  55                  60

Lys Gly Arg Phe Thr Val Ser Arg Asp Asn Ala Lys Asn Thr Leu Tyr
65                  70                  75                  80

Leu Gln Met Asn Ser Leu Thr Ser Glu Asp Thr Ala Val Tyr Tyr Cys
                85                  90                  95

Ala Ala His Tyr Phe Gly Ser Ser Gly Pro Phe Ala Tyr Trp Gly Gln
            100                 105                 110

Gly Thr Leu Val Thr Val Ser Ser
        115                 120
```

<210> SEQ ID NO 7
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 7

```
Asp Ile Gln Met Thr Gln Ser Pro Ala Ser Leu Ser Ala Ser Val Gly
1               5                   10                  15

Asp Arg Val Thr Ile Thr Cys Arg Ala Ser Glu Asn Ile Phe Ser Tyr
            20                  25                  30

Leu Ala Trp Tyr Gln Gln Lys Pro Gly Lys Ser Pro Lys Leu Leu Val
        35                  40                  45

Tyr Asn Thr Arg Thr Leu Ala Glu Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln His His Tyr Gly Thr Pro Phe
                85                  90                  95

Thr Phe Gly Ser Gly Thr Lys Leu Glu Ile Lys
            100                 105
```

<210> SEQ ID NO 8
<211> LENGTH: 449
<212> TYPE: PRT
<213> ORGANISM: Artificial sequence
<220> FEATURE:
<223> OTHER INFORMATION: Synthetic polypeptide -continued

<400> SEQUENCE: 8

Glu Val Gln Leu Gln Glu Ser Gly Pro Gly Leu Val Lys Pro Gly Gly
1               5                   10                  15

Ser Leu Ser Leu Ser Cys Ala Ala Ser Gly Phe Val Phe Ser Ser Tyr
            20                  25                  30

Asp Met Ser Trp Val Arg Gln Thr Pro Glu Arg Gly Leu Glu Trp Val
        35                  40                  45

Ala Tyr Ile Ser Ser Gly Gly Gly Ile Thr Tyr Ala Pro Ser Thr Val
    50                  55                  60

Lys Gly Arg Phe Thr Val Ser Arg Asp Asn Ala Lys Asn Thr Leu Tyr
65                  70                  75                  80

Leu Gln Met Asn Ser Leu Thr Ser Glu Asp Thr Ala Val Tyr Tyr Cys
                85                  90                  95

Ala Ala His Tyr Phe Gly Ser Ser Gly Pro Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

-continued

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 9
<211> LENGTH: 214
<212> TYPE: PRT
<213> ORGANISM: Artificial sequence
<220> FEATURE:
<223> OTHER INFORMATION: Synthetic polypeptide

<400> SEQUENCE: 9

Asp Ile Gln Met Thr Gln Ser Pro Ala Ser Leu Ser Ala Ser Val Gly
1               5                   10                  15

Asp Arg Val Thr Ile Thr Cys Arg Ala Ser Glu Asn Ile Phe Ser Tyr
            20                  25                  30

Leu Ala Trp Tyr Gln Gln Lys Pro Gly Lys Ser Pro Lys Leu Leu Val
        35                  40                  45

Tyr Asn Thr Arg Thr Leu Ala Glu Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln His His Tyr Gly Thr Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```